United States Patent
Cleveland et al.

(10) Patent No.: US 12,324,577 B1
(45) Date of Patent: Jun. 10, 2025

(54) METHOD OF AUGMENTING TISSUE

(71) Applicant: Ocean Orthopedics, Inc., Westport, MA (US)

(72) Inventors: Benjamin Cleveland, Westport, MA (US); Thomas Gamache, Westport, MA (US); Samuel Grossman, Westport, MA (US); Jonathan Moreno, Westport, MA (US); Thomas Piscatelli, Westport, MA (US)

(73) Assignee: Ocean Orthopedics, Inc., Westport, MA (US)

( * ) Notice: Subject to any disclaimer, the term of this patent is extended or adjusted under 35 U.S.C. 154(b) by 0 days.

(21) Appl. No.: 18/896,724

(22) Filed: Sep. 25, 2024

Related U.S. Application Data

(60) Provisional application No. 63/561,670, filed on Mar. 5, 2024.

(51) Int. Cl.
*A61B 17/04* (2006.01)
*A61B 17/00* (2006.01)

(52) U.S. Cl.
CPC ........ *A61B 17/0401* (2013.01); *A61B 2017/00557* (2013.01); *A61B 2017/0464* (2013.01)

(58) Field of Classification Search
CPC .......... A61B 17/0401; A61B 17/00234; A61B 17/00; A61B 17/0466; A61B 2017/0464; A61B 2017/0495; A61F 2/0811
See application file for complete search history.

(56) References Cited

U.S. PATENT DOCUMENTS

| | | |
|---|---|---|
| 8,585,773 B1 | 11/2013 | Kucklick |
| 8,753,390 B2 | 6/2014 | Shohat |
| 9,289,307 B2 | 3/2016 | Shohat |
| 9,757,132 B2 | 9/2017 | Laurencin et al. |
| 9,770,337 B2 | 9/2017 | Shohat |
| 10,568,622 B2 | 2/2020 | Euteneuer et al. |
| 10,617,787 B2 | 4/2020 | Francis et al. |
| 10,653,817 B2 | 5/2020 | Francis et al. |
| 10,806,565 B2 | 10/2020 | Euteneuer et al. |
| 10,835,639 B1 | 11/2020 | Francis et al. |
| 10,864,072 B2 | 12/2020 | Van Kampen et al. |
| 10,881,441 B2 | 1/2021 | Euteneuer et al. |
| 10,888,415 B2 | 1/2021 | Van Kampen |
| 10,966,815 B1 | 4/2021 | Kemper et al. |
| 11,020,111 B2 | 6/2021 | Euteneuer et al. |
| 11,020,509 B2 | 6/2021 | Francis et al. |
| 11,033,398 B2 | 6/2021 | Shohat |
| 11,051,808 B2 | 7/2021 | Euteneuer et al. |

(Continued)

*Primary Examiner* — Dianne Dornbusch
(74) *Attorney, Agent, or Firm* — Nutter, McClennen & Fish, LLP

(57) ABSTRACT

A method of repairing tissue of a patient secures at least two sutures to two initial points of the patient, and couples sutures to a repair matrix comprising a scaffold portion and an expandable portion. The scaffold portion is configured to integrate over time with the tissue being repaired. The method also expands the expandable portion to urge the repair matrix against the tissue to produce a securing surface, and then secures the at least two sutures to two additional points of the patient. The at least two sutures traverse the securing surface of the repair matrix between the two initial points and the two additional points to secure the repair matrix to the patient.

10 Claims, 43 Drawing Sheets

(56) References Cited

U.S. PATENT DOCUMENTS

| | | |
|---|---|---|
| 11,051,932 B2 | 7/2021 | Euteneuer et al. |
| 11,058,532 B2 | 7/2021 | Rocco et al. |
| 11,065,102 B2 | 7/2021 | Rocco et al. |
| 11,076,851 B2 | 8/2021 | Westling et al. |
| 11,096,776 B2 | 8/2021 | Rocco et al. |
| 11,116,622 B2 | 9/2021 | Rocco et al. |
| 11,116,870 B2 | 9/2021 | Francis et al. |
| 11,213,610 B2 | 1/2022 | Francis et al. |
| 11,273,026 B2 | 3/2022 | Rocco et al. |
| 11,331,180 B2 | 5/2022 | Zenz-Olson |
| 11,331,410 B2 | 5/2022 | Francis et al. |
| 11,338,056 B2 | 5/2022 | Francis et al. |
| 11,338,057 B2 | 5/2022 | Francis et al. |
| 11,357,613 B2 | 6/2022 | Rocco et al. |
| 11,413,032 B2 | 8/2022 | Running et al. |
| 11,413,133 B2 | 8/2022 | Euteneuer et al. |
| 11,457,916 B2 | 10/2022 | Westling et al. |
| 11,510,702 B2 | 11/2022 | Zenz-Olson et al. |
| 11,523,895 B2 | 12/2022 | Rocco et al. |
| 11,559,330 B2 | 1/2023 | Jones et al. |
| 11,607,305 B2 | 3/2023 | Van Kampen |
| 11,622,847 B2 | 4/2023 | Rocco et al. |
| 11,672,646 B2 | 6/2023 | Rocco et al. |
| 11,701,217 B2 | 7/2023 | Rocco et al. |
| 11,712,332 B2 | 8/2023 | Rocco et al. |
| 11,717,393 B2 | 8/2023 | Van Kampen et al. |
| 11,723,706 B2 | 8/2023 | Euteneuer et al. |
| 11,771,547 B2 | 10/2023 | Kemper et al. |
| 11,793,510 B2 | 10/2023 | Euteneuer et al. |
| 11,806,440 B2 | 11/2023 | Johnson et al. |
| 11,826,228 B2 | 11/2023 | Shohat |
| 2006/0029633 A1 | 2/2006 | Kaiser et al. |
| 2009/0156997 A1* | 6/2009 | Trenhaile ............... A61F 2/0063 604/99.01 |
| 2010/0023127 A1 | 1/2010 | Shohat |
| 2011/0125287 A1 | 5/2011 | Hotter et al. |
| 2011/0224702 A1 | 9/2011 | Van Kampen et al. |
| 2014/0296987 A1 | 10/2014 | Shohat |
| 2016/0199189 A1 | 7/2016 | Shohat |
| 2016/0256254 A1 | 9/2016 | Kucklick |
| 2016/0262780 A1 | 9/2016 | Kucklick |
| 2017/0216016 A1 | 8/2017 | Sengun et al. |
| 2017/0273680 A1* | 9/2017 | Sengun ................. A61L 31/044 |
| 2018/0000603 A1 | 1/2018 | Shohat |
| 2019/0282352 A1 | 9/2019 | Kucklick |
| 2020/0000573 A1 | 1/2020 | Whittaker et al. |
| 2020/0215228 A1 | 7/2020 | Coulombe et al. |
| 2022/0401627 A1 | 12/2022 | Barnes et al. |
| 2023/0019753 A1 | 1/2023 | Yue et al. |
| 2023/0023513 A1 | 1/2023 | Ji et al. |
| 2023/0035742 A1 | 2/2023 | Yue et al. |
| 2023/0338135 A1 | 10/2023 | Van Kampen et al. |

* cited by examiner

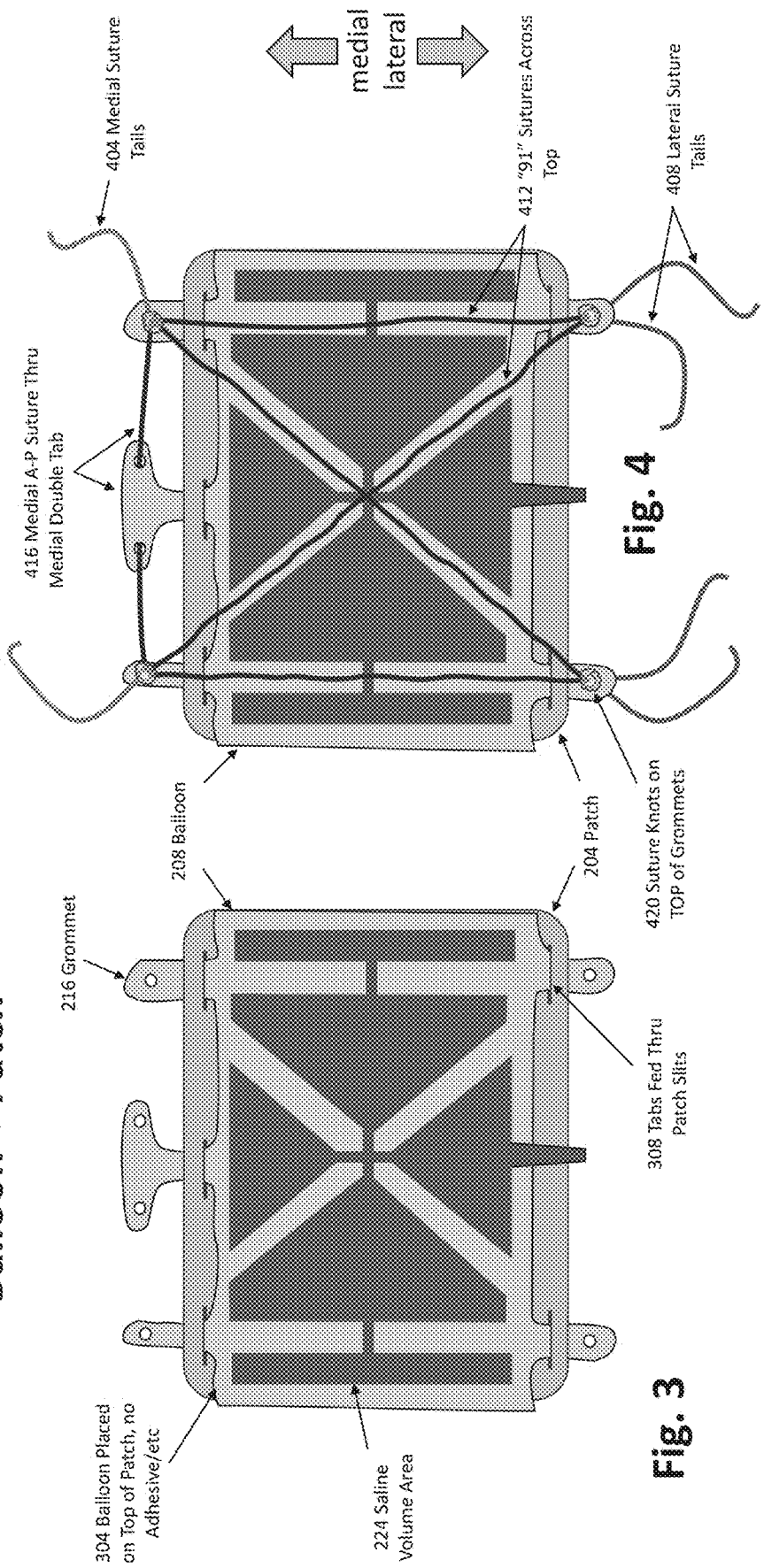

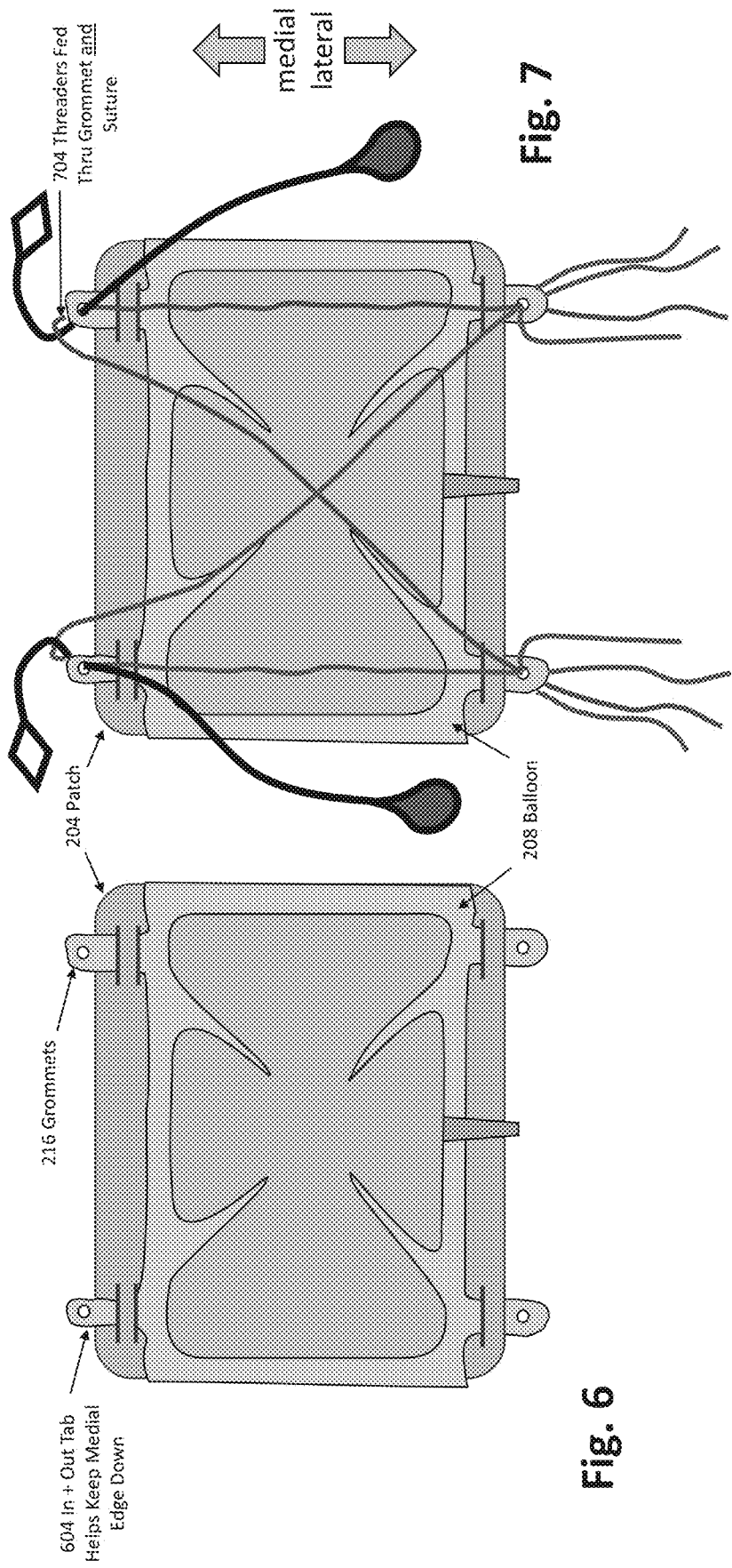

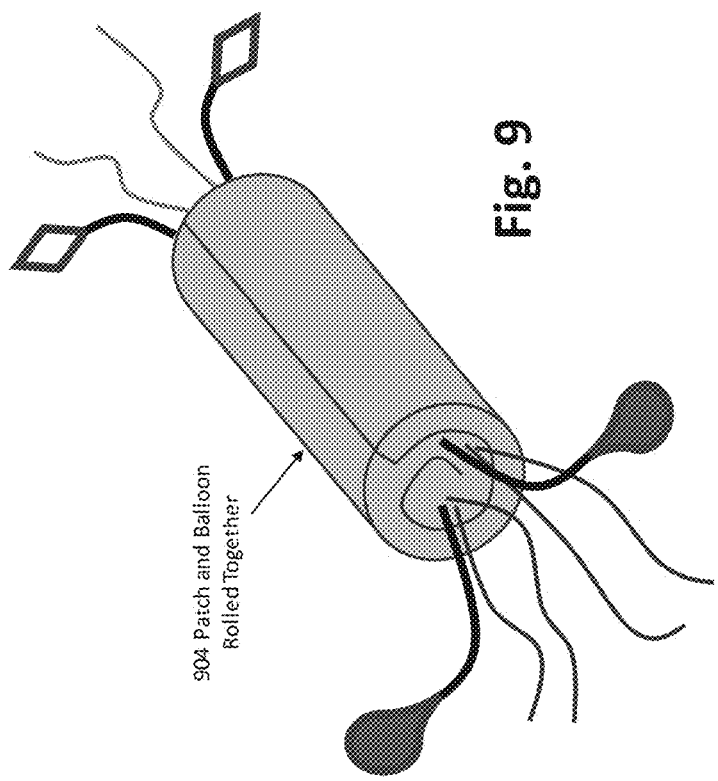
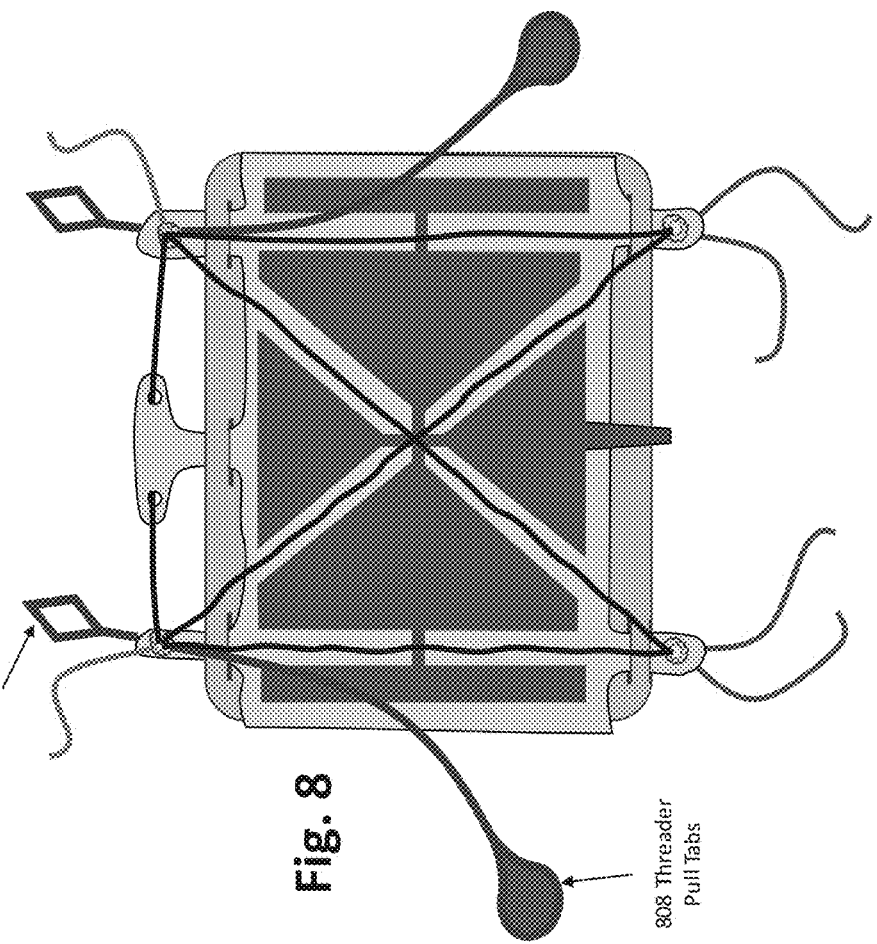

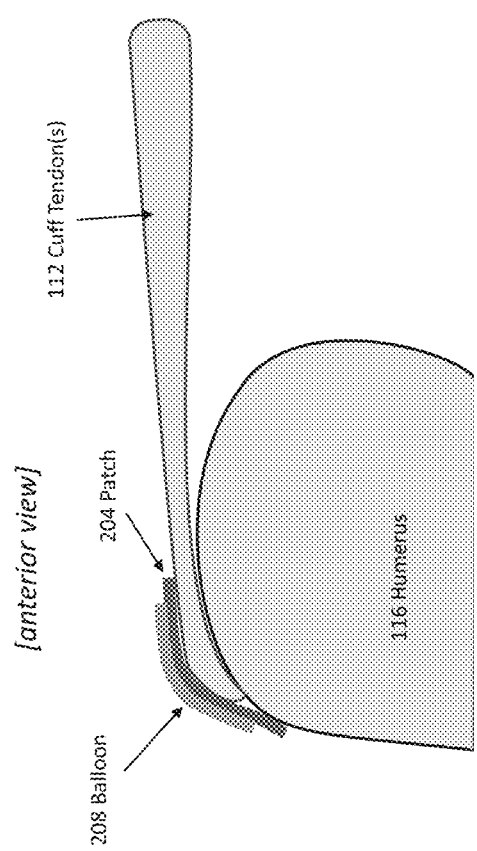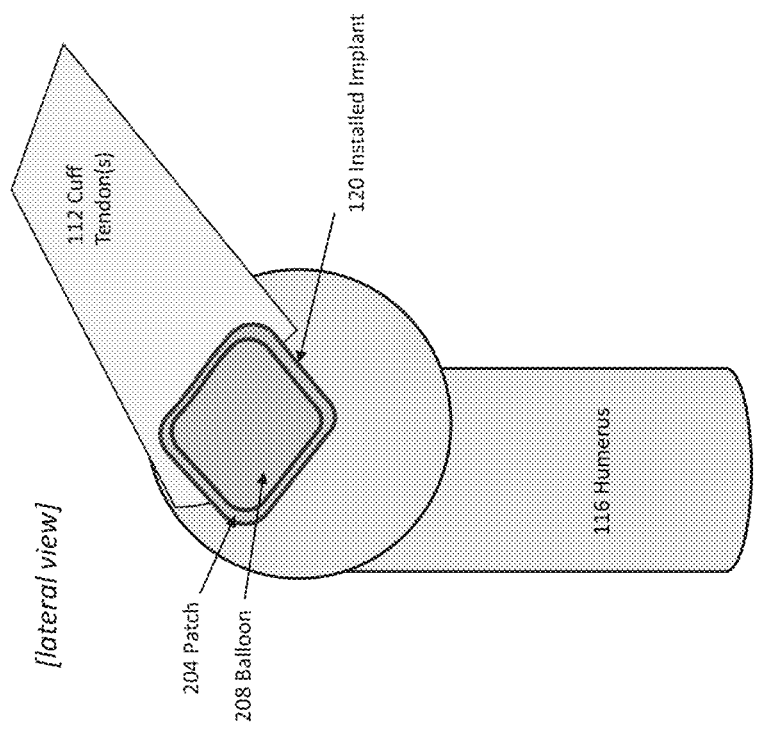
Fig. 21

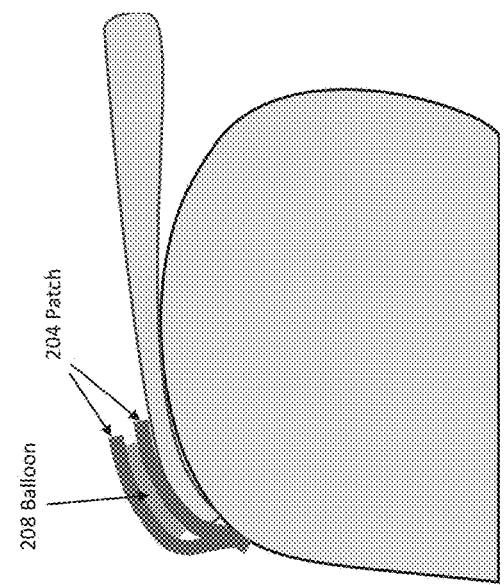
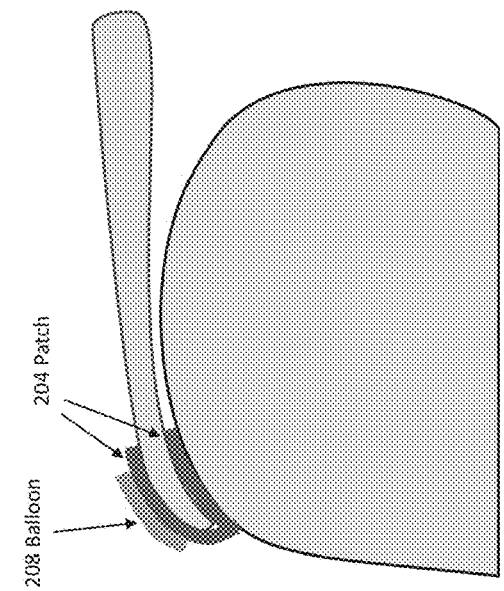
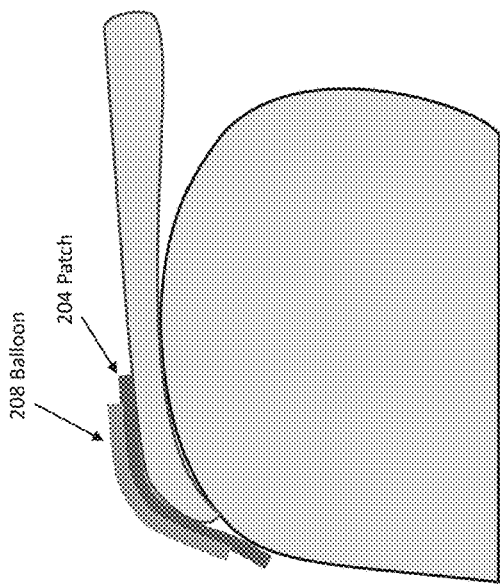
Fig. 22

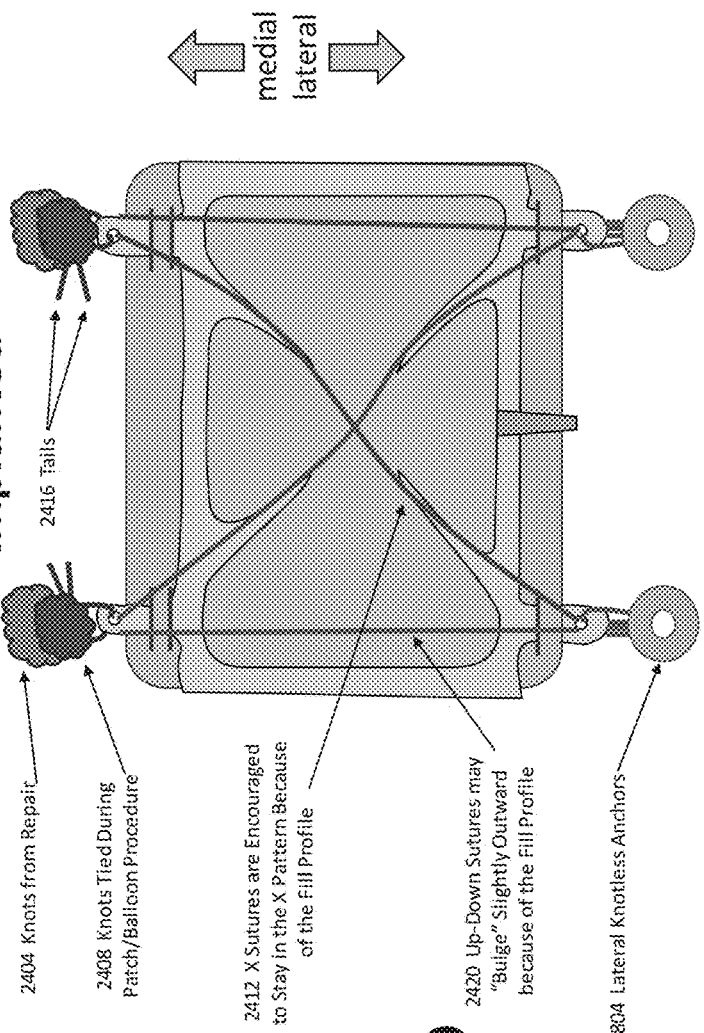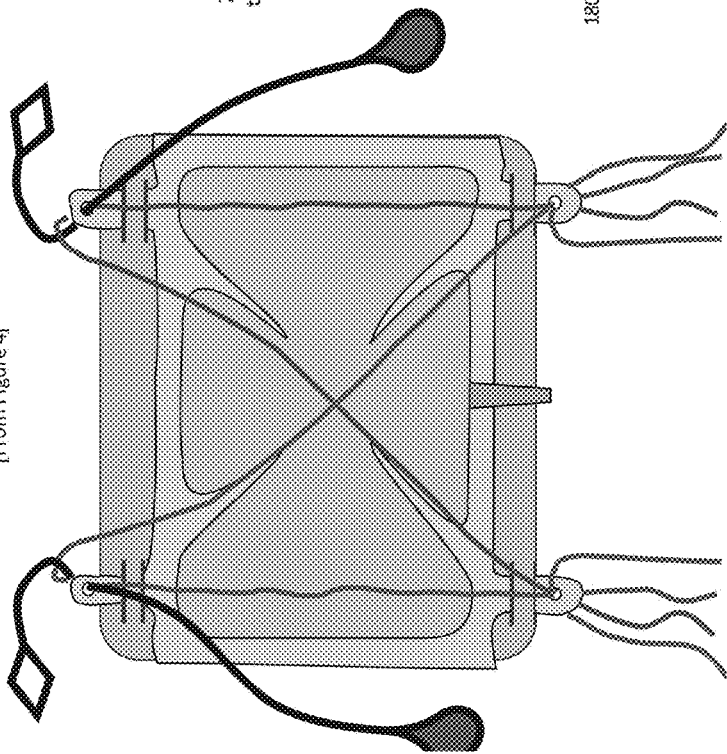
Concept 1.1:
Included IXI, Medial Tails Cut
Fig. 24

Concept 1.2:
Included IXI, Medial Tails Secured Laterally
Fig. 25
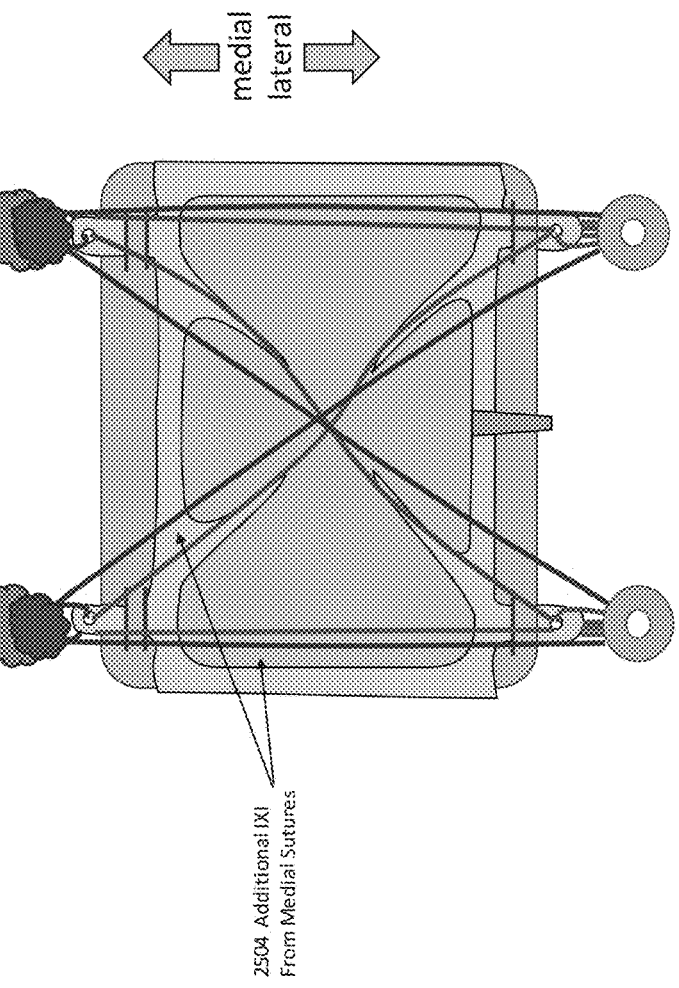
As Manufactured
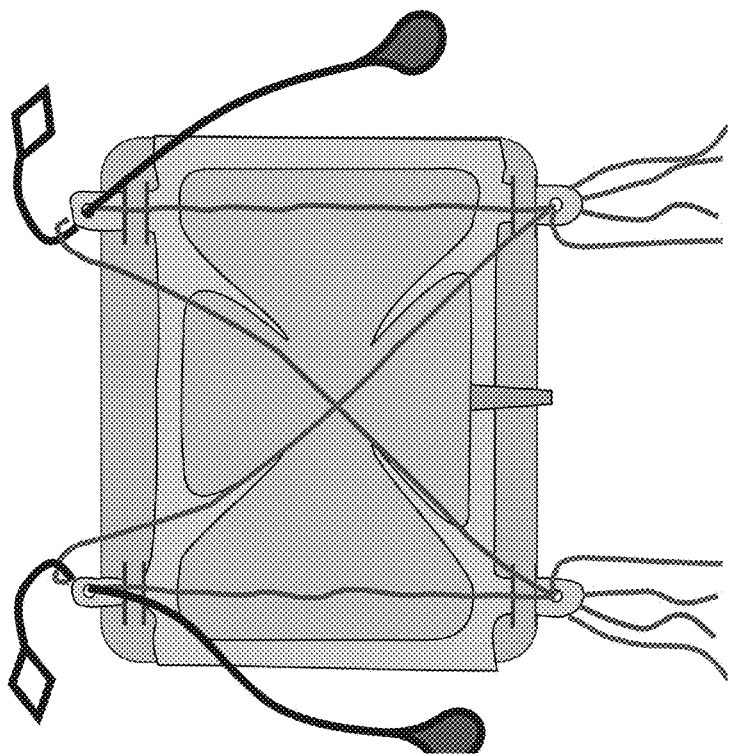
Implanted
2504 Additional IXI
From Medial Sutures

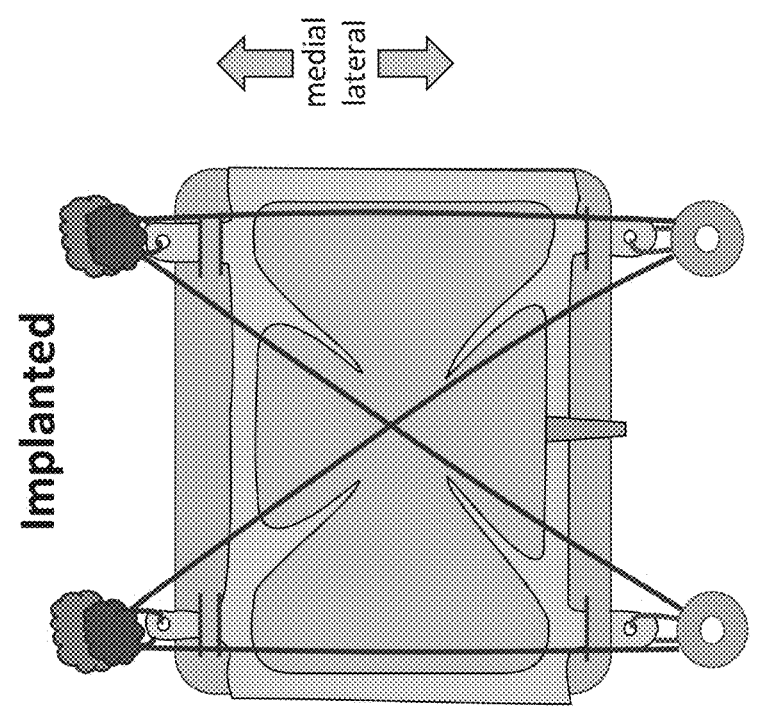
Concept 2.1:
No IXI, Medial Tails Secured Laterally
Fig. 26
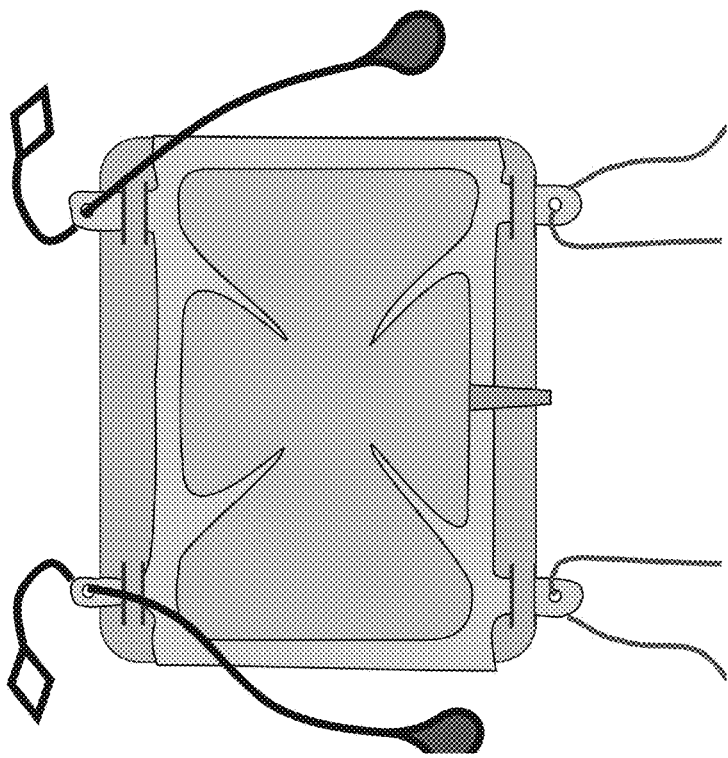

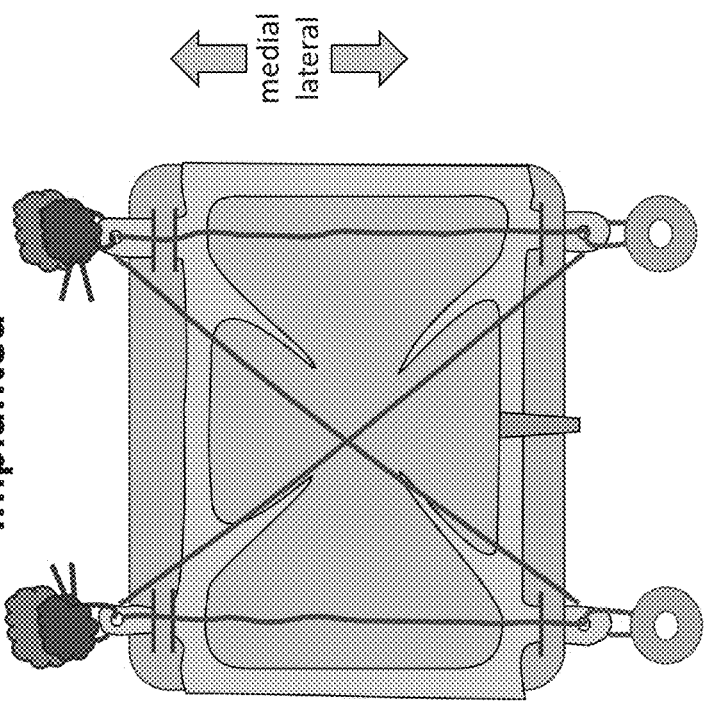
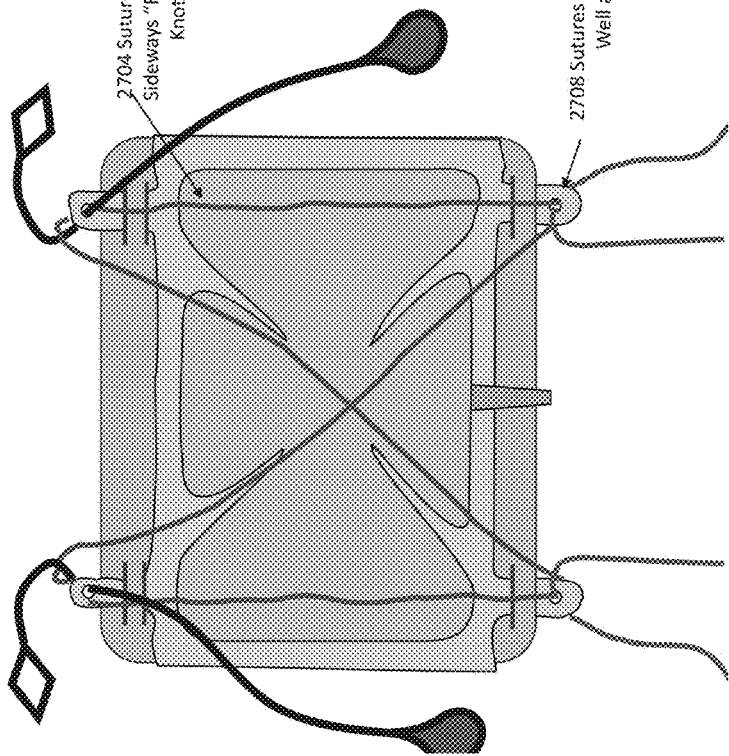
Concept 3.1:
Included ∞, Medial Tails Cut
Fig. 27

Concept 3.2:
Included ∞, Medial Tails Secured Laterally
Fig. 28
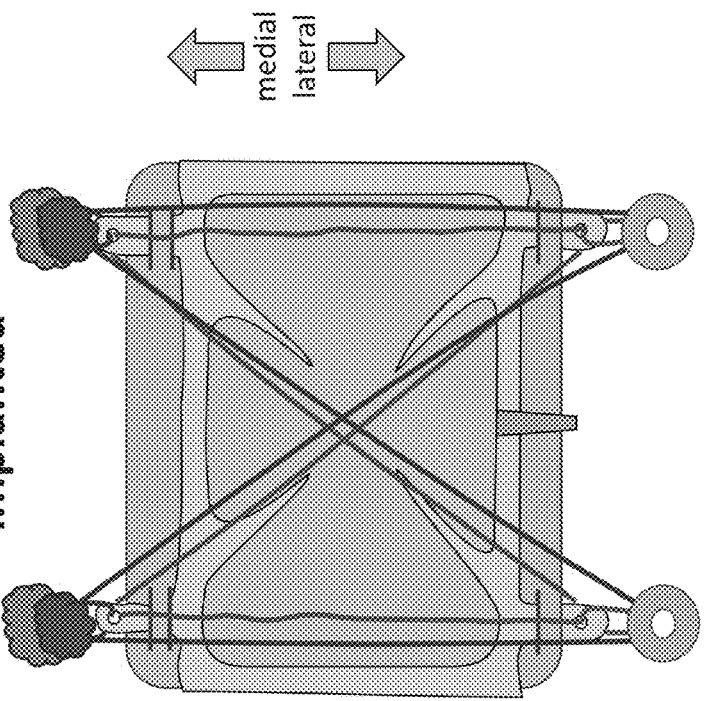
Implanted
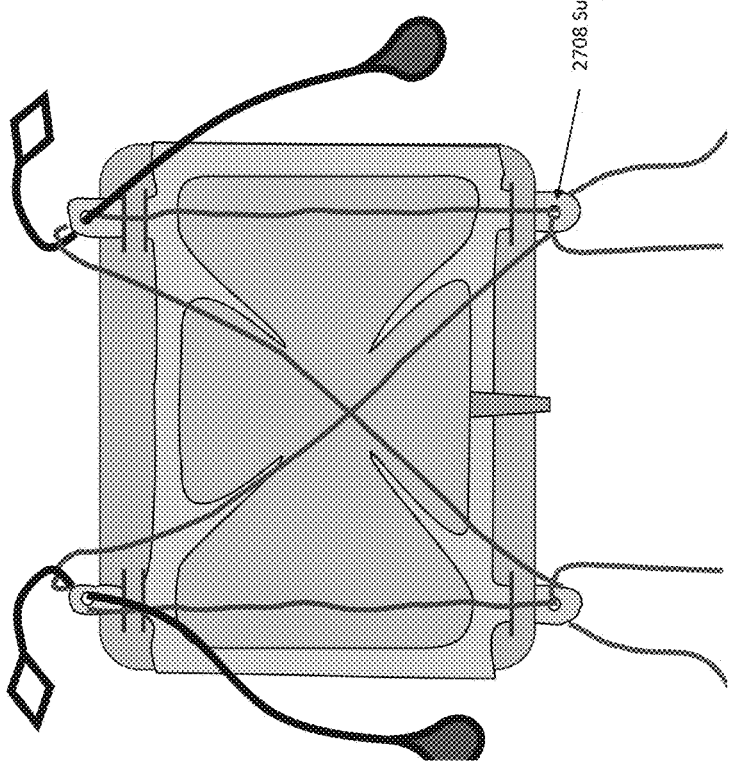
As Manufactured
2708 Sutures Interlock Each Other, as Well as the Grommet

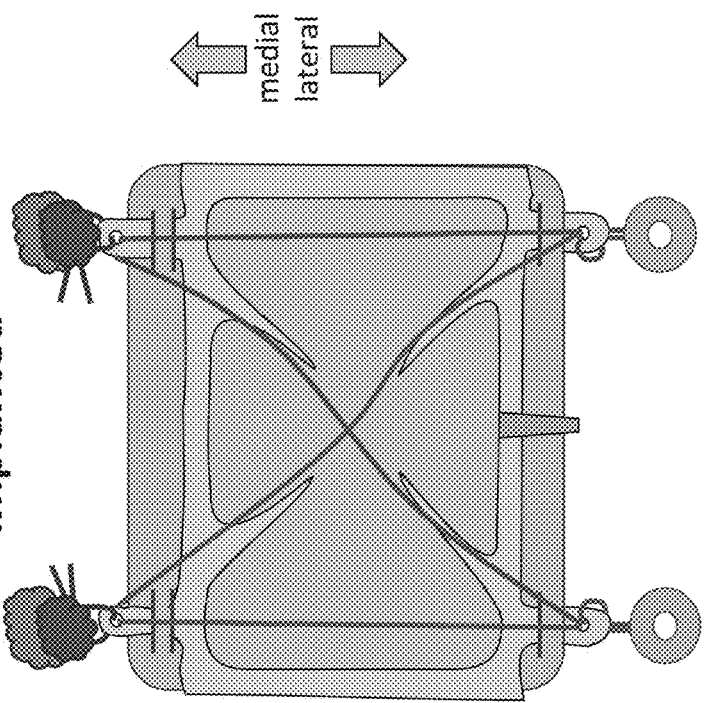
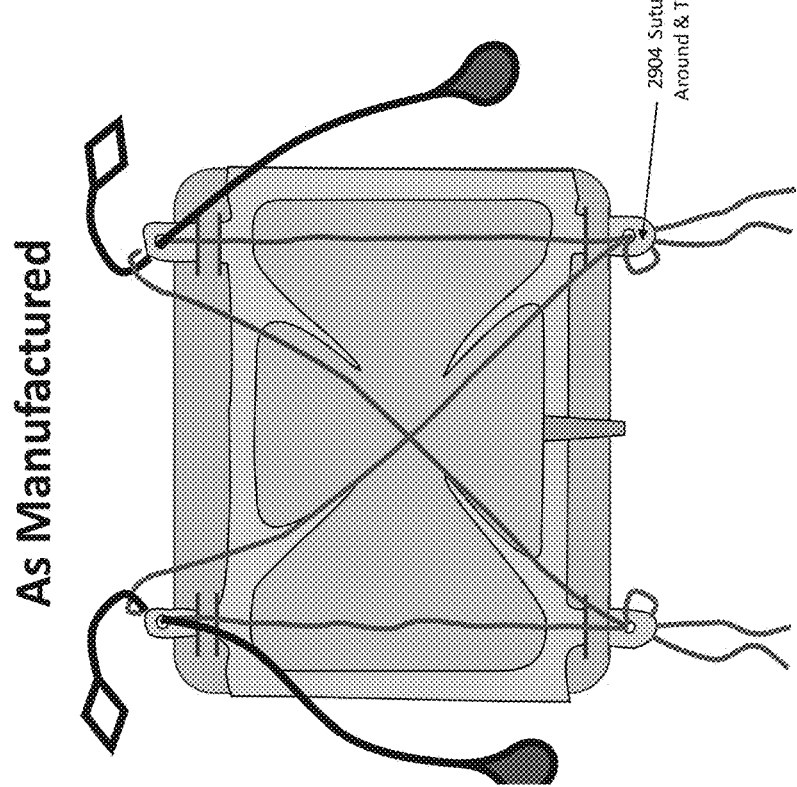
Concept 4.1:
Included IXI w/Loops, Medial Tails Cut
Fig. 29

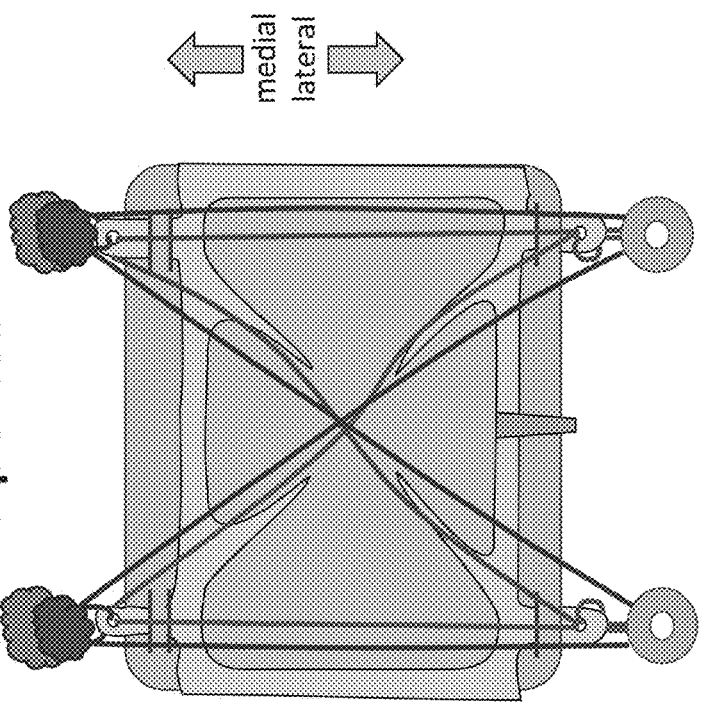
Concept 4.2:
Included IXI w/Loops, Medial Tails Secured Laterally
Fig. 30
As Manufactured
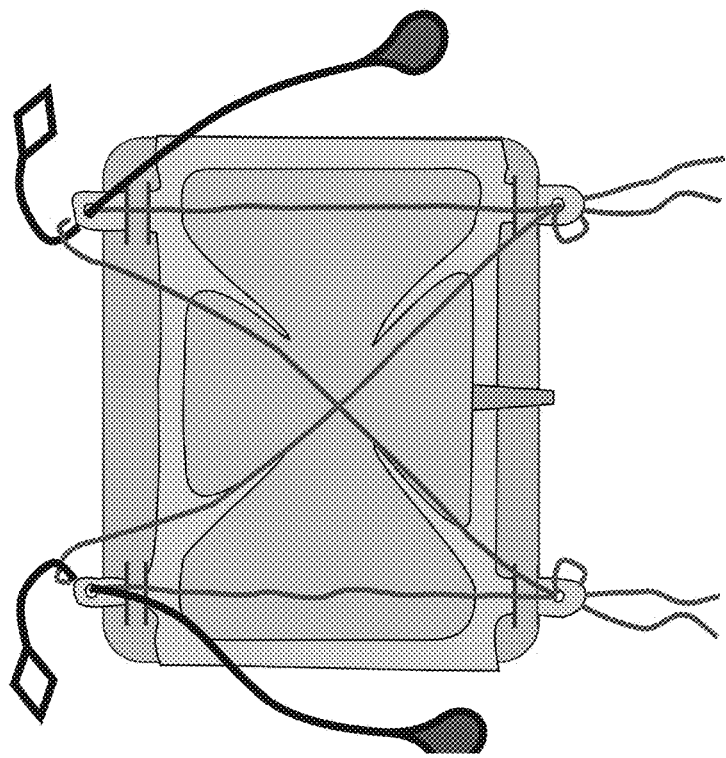
Implanted
medial ← → lateral

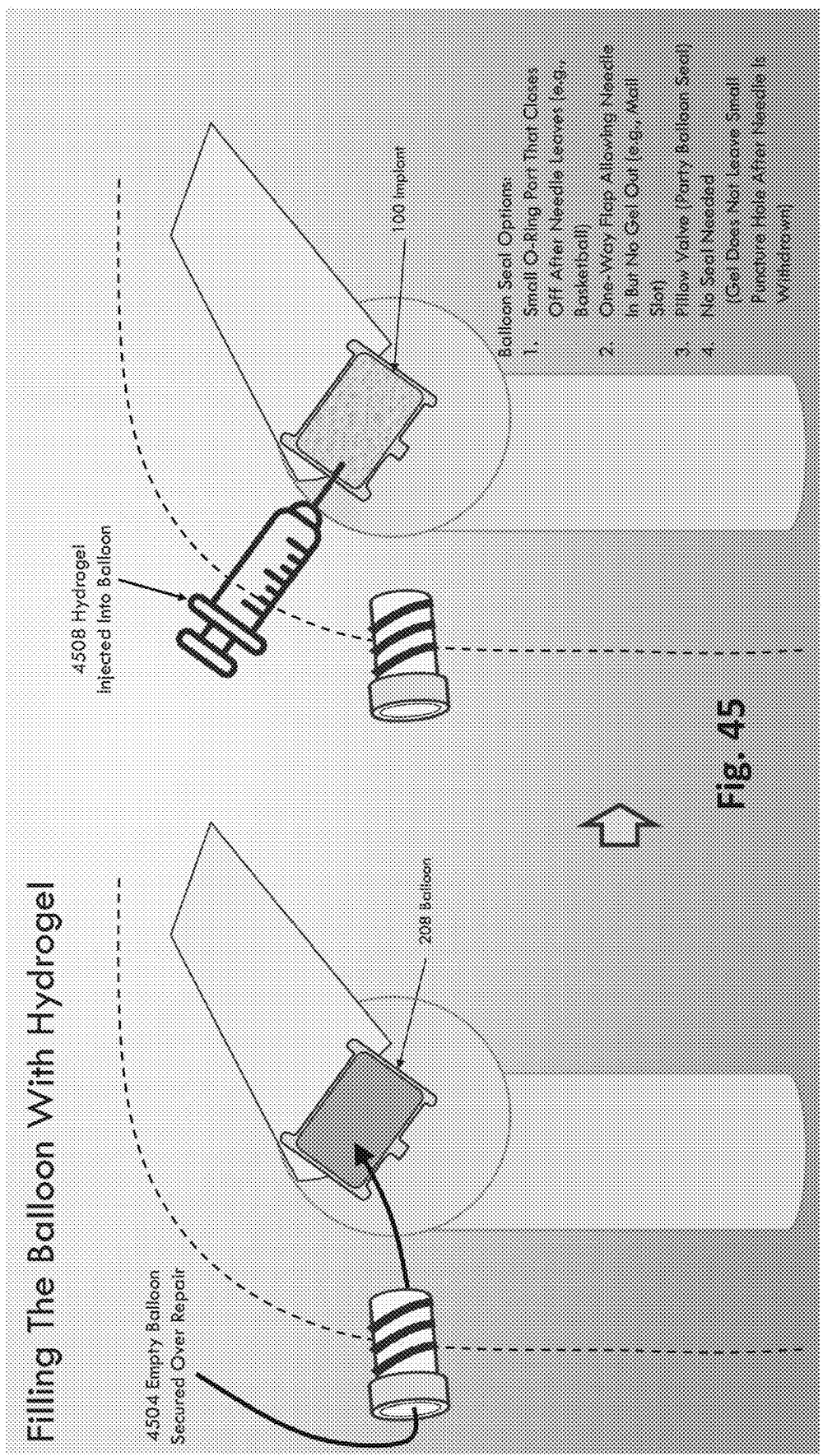

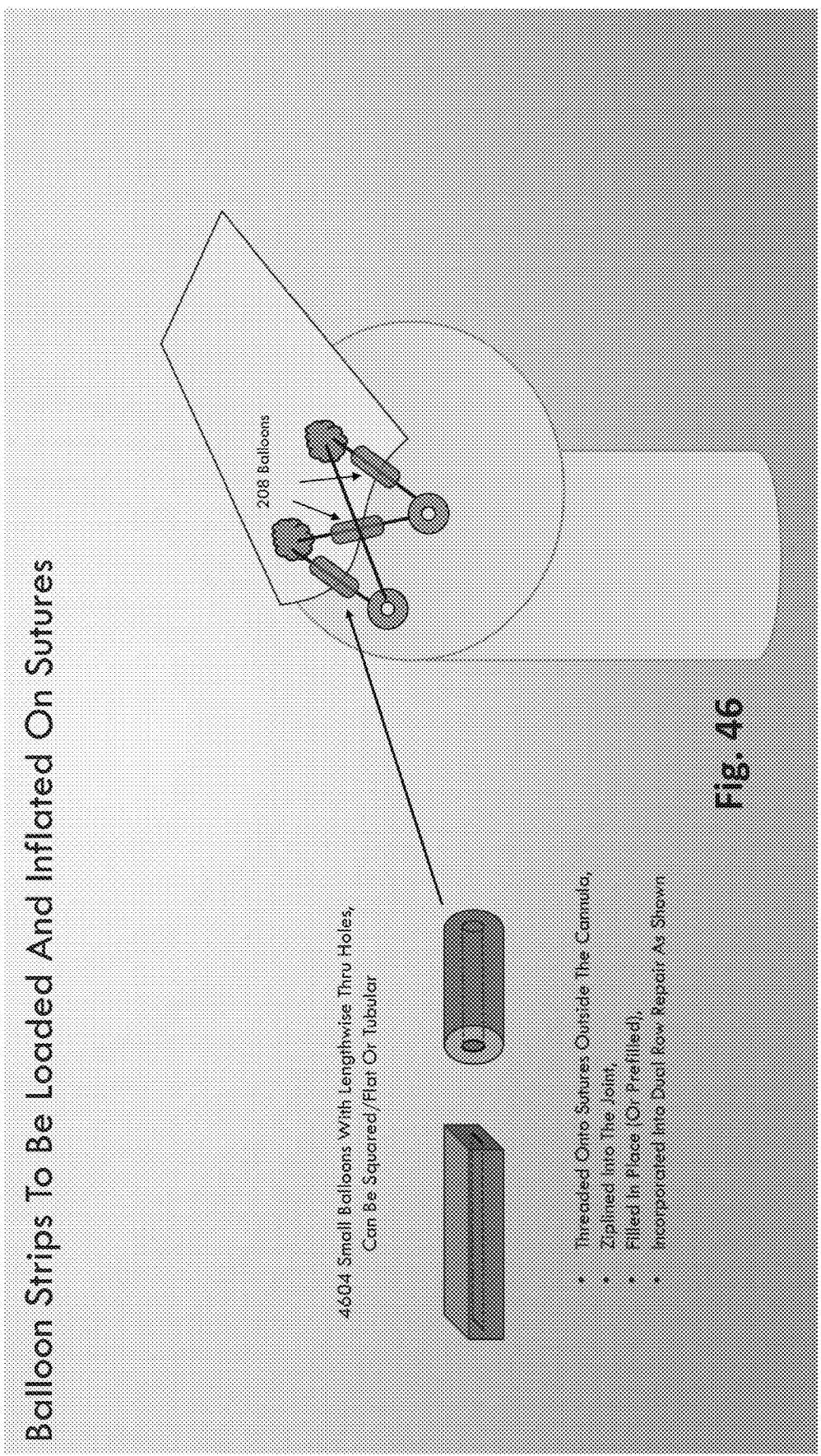

METHOD OF AUGMENTING TISSUE

PRIORITY

This patent application claims priority from provisional U.S. patent application No. 63/561,670, filed Mar. 5, 2024, entitled, "SYSTEM AND METHOD OF REPAIRING TISSUE USING PATCH AND BIASING MEMBER," and naming Benjamin Cleveland, Thomas Gamache, Samuel Grossman, Jonathan Moreno, Thomas Piscatelli as inventors, the disclosure of which is incorporated herein, in its entirety, by reference.

RELATED APPLICATIONS APPLICATION

This patent application is related to U.S. patent application Ser. No. 18/896,665, filed on even date herewith, entitled, EXPANDABLE MEMBER AND PATCH SYSTEM FOR AUGMENTING TISSUE, and naming Benjamin Cleveland, Thomas Gamache, Samuel Grossman, Jonathan Moreno, Thomas Piscatelli as inventors, the disclosure of which is incorporated herein, in its entirety, by reference.

This patent application also is related to U.S. patent application Ser. No. 18/896,670, filed on even date herewith, entitled, SYSTEM FOR SURGICALLY AUGMENTING TISSUE, and naming Benjamin Cleveland, Thomas Gamache, Samuel Grossman, Jonathan Moreno, Thomas Piscatelli as inventors, the disclosure of which is incorporated herein, in its entirety, by reference.

FIELD

Illustrative embodiments of the invention generally relate to soft tissue repair and, more particularly, various embodiments of the invention relate to collagen patches for soft tissue repair and related technologies.

BACKGROUND

Rotator cuff repairs can benefit from patch implants that protect and assist the repair site both mechanically and biologically. Mechanically, the patch acts as a barrier between the delicate soft tissue repair and the acromion, cushioning against loads from shoulder movements. By attaching the patch both medially to the rotator cuff tendon and laterally to the humerus, it helps distribute the tension, easing the stress on the repair site. Biologically, the patch, often made from bovine type I collagen, integrates with the body, serving as a scaffold for tissue regeneration. This promotes tendon healing by facilitating tenocyte and fibroblast infiltration and (initially) type III collagen formation, enhancing tendon thickness, strength, and healing speed.

Undesirably, collagen patches can introduce new complexities and sources of error to the repair process.

SUMMARY OF VARIOUS EMBODIMENTS

Example 1

In accordance with one embodiment of the invention, a system for surgically augmenting (e.g., repairing) tissue of a patient includes a patch configured to integrate with the tissue being repaired, and an expandable member associated with the patch. The patch includes a patch material that progressively integrates with tissue of the patient (e.g., at least in part via biological processes of the patient). In a similar manner, the expandable member is formed of a member material that progressively degrades within the patient at least in part via biological processes of the patient. The expandable member is configured to urge the patch toward the target tissue (e.g., generally inwardly toward the patient's body, such as toward a treated portion of tissue) after placement in or on the patient.

The expandable member and patch may be associated in a number of ways. For example, the expandable member may be integrated with the patch. As another example, expandable member may be separate and mechanically connected to the patch (e.g., via an adhesive or other connection mechanism). To urge the patch toward the tissue, the expandable member may be formed from a material that expands in response to receipt of a fluid (e.g., forming an inflatable balloon having the expandable interior).

One implementation of the expandable member therefore uses a pillow valve. The expandable member preferably has generally rectangular shape. The expanded thickness may have a longest dimension of about 5 to 80% of the width. Other ranges may be between 10% and 70%, 20% and 60%, or the like.

In some embodiments, the expandable member is configured to receive a securement component such as one or more of a suture, tack, staple, glue, and/or Velcro (e.g., hook and loop) to couple with the tissue. When implemented as one or more balloons or the like, the expandable member may be configured to contain a liquid, such as a hydrogel, sterile air, or a liquid collagen. In some embodiments, the liquid may include a saline solution of a sufficient salinity to permit osmotic inflow of water to the volume of the expandable member. In a similar manner, the interior volume of the expandable member may be configured to receive a drug for elution into the patient.

The patch material preferably comprises collagen. Typically, the patch material is configured to integrate with the tissue faster than the expandable member degrades within the patient. Moreover, rather than forming two layers, some embodiments of the system at least partly encapsulate the expandable member within the patch (e.g., the patch may form a receiving area containing the expandable member).

The system also may have a sensor associated with one or both the expandable member and/or the patch. This sensor is configured to collect patient data and/or device data (e.g., data relating to the expandable member, patch, and/or some other component in the system or matrix). Some embodiments also have a tube (e.g., a catheter) terminating at a luer. The tube is in fluid communication with the expandable member, and the luer is configured to receive a luer-standard pressure device.

In accordance with another embodiment, a system for surgically augmenting tissue of a patient has an expandable member formed of a member material that progressively degrades within the patient at least in part via hydrolysis or similar processes (e.g., as part of biological processes in the patient). The expandable member has a width dimension and a length dimension that together form a patch receiving area configured to receive and secure a collagen patch. The expandable member is configured to urge the collagen patch toward the tissue after the collagen patch is secured to the receiving area and placed in or on the patient.

In accordance with other embodiments, a method provides an expandable member formed of a member material that progressively degrades within the patient at least in part via biological processes in the patient. The expandable member has a width dimension and a length dimension that together form a patch receiving area. Next, the method secures a collagen patch to the patch receiving area of the expandable member. As such, the expandable member is configured to urge the collagen patch toward the tissue after the collagen patch is secured to the receiving area and placed in or on the patient.

In accordance with yet other embodiments, a surgical balloon system has an expandable body forming a fluid inlet to an interior volume configured to receive an inflation media. The expandable body defines an exterior to the interior volume and, as such, the interior volume has an internal pressure relative to the exterior pressure. The system also has a pillow valve configured to manage inflow of the inflation media to the interior volume via the fluid inlet. The pillow valve has a sealing area forming a two-dimensional seal to seal the interior volume of the expandable body. Additionally, the pillow valve is configured to seal when the interior pressure of the expandable body exceeds the exterior pressure.

Example 2

In accordance with one embodiment of the invention, a system for surgically augmenting tissue of a patient has a patch configured to integrate with the tissue being repaired and an expandable member defining a longitudinal axis. The patch includes patch material that progressively integrates with tissue of the patient at least in part via biological processes in the patient. The system also has a suture channel extending through the expandable portion in a direction generally parallel to the longitudinal axis of the expandable portion. The suture channel has a first end and a second end sized and configured to receive and pass a suture therethrough.

As with many members, the expandable member has a first edge and a second edge. The first end of the suture channel may be at the first edge of the expandable member, while the second end of the suture channel may be at the second edge of the expandable member.

One implementation of the expandable member therefore uses a pillow valve. Also, among other things, the expandable member may include an inflatable balloon having an expandable interior.

To enable a good connection, the suture channel may extend at least halfway across the longest dimension of the expandable member. For example, the suture channel may extend across the entire extent of the expandable member. In some embodiments, the suture channel is continuous or discontinuous (e.g., exposing the suture to the top or bottom of the balloon). Moreover, the patch may be considered to form a first footprint while the expandable member forms a second footprint. The first footprint preferably is greater than the second footprint. Other embodiments may be the opposite or generally equal.

Some implementations of the expandable member are configured to urge the patch toward the tissue after placement in or on the patient. Moreover, the patch material may be formed at least in part from collagen. In a similar manner, the expandable member may be formed to progressively degrade within the patient at least in part via biological processes in the patient. Preferably, the patch is configured to integrate with the tissue faster than the expandable portion degrades within the patient.

In a manner similar to the expandable member, the patch also may form a patch longitudinal axis and a second suture channel generally parallel to the patch longitudinal axis. The system also may have a sensor associated with one or both the expandable member and/or the patch. This sensor is configured to collect data (e.g., patient data, procedure data, or data relating to the implant). When implemented as a balloon or the like, the expandable member may be configured to contain a liquid, such as saline solution of a sufficient salinity to permit osmotic inflow of water to the volume of the expandable member. In a similar manner, the interior volume of the expandable member may be configured to receive a drug for elution into the patient. To that end, the expandable member configured to permit outflow of the drug for elution into the patient.

The expandable member and patch may be associated in a number of ways. For example, the expandable member may be integrated with the patch. As another example, expandable member may be separate and mechanically connected to the patch (e.g., via an adhesive or other connection mechanism). Moreover, rather than forming two layers, some embodiments of the system at least partly encapsulate the expandable member within the patch (e.g., the patch may form a receiving area containing the expandable member).

The expandable member also may be tufted in at least one location.

In accordance with another embodiment, a system for surgically augmenting tissue of a patient has a scaffold portion comprising scaffold material that progressively integrates with tissue of the patient at least in part via biological processes in the patient. The scaffold portion defines a first longitudinal axis. The system also has an expandable portion configured to urge the scaffold portion toward the tissue after placement in or on the patient. In a manner similar to the scaffold portion, the expandable portion defines a second longitudinal axis. The scaffold portion and expandable portion are associated to form repair matrix having an interior. At least one suture channel extends through the interior of the repair matrix in a direction generally parallel to one or both the first and second longitudinal axes. Each suture channel has two open ends sized and configured to receive and pass a suture.

In accordance with yet other embodiments, a system for surgically augmenting tissue of a patient has a scaffold portion comprised of scaffold material that progressively integrates with tissue of the patient at least in part via biological processes in the patient. The system also has an expandable portion configured to urge the scaffold portion toward the tissue after placement in or on the patient. The expandable portion defines a top surface, a bottom surface, and at least one side surface, and the top and bottom surfaces define a thickness of the expandable portion. Like other embodiments, the expandable portion also has two edges.

At least one suture channel extends through the interior of the expandable portion between the top and bottom surfaces of the expandable portion. The at least one suture channel is within the thickness of the expandable portion, terminating approximately at or between a) two edges or b) one of the edges and no more than one of the surfaces of the expandable portion. The at least one suture channel is generally straight and has two open ends sized and configured to receive and pass a suture.

Example 3

In accordance with one embodiment of the invention, a method of augmenting tissue of a patient secures at least two sutures to two initial points of the patient, and couples sutures to a repair matrix comprising a scaffold portion and an expandable portion. The scaffold portion is configured to integrate over time with the tissue being repaired. The method also expands the expandable portion to urge the repair matrix against the tissue to produce a securing surface, and then secures the at least two sutures to two additional points of the patient. The at least two sutures traverse the securing surface of the repair matrix between the two initial points and the two additional points to secure the repair matrix to the patient.

Expansion typically causes the repair matrix to change shape toward a flatter configuration (but not necessarily flat). The at least two sutures may form an X-pattern across the securing surface. Moreover, the at least two sutures may be secured to the two additional points with anchors.

The method may expand the expandable portion in any of a number of manners. To that end, the method may direct a fluid (e.g., saline or air) through a tube and into the expanding portion. In that case, the expandable portion may include an inflatable balloon. The expandable portion may include a pillow valve to receive fluid for expansion.

To provide its function, the scaffold portion may include a collagen patch. The scaffold portion and expandable portion may be either integrated together or mechanically coupled together. Preferably, the expandable portion is configured to degrade within the patient. In a similar manner, the scaffold portion may be configured to integrate with the tissue faster than the expandable portion degrades within the patient. Sometimes, the method may add a drug to the expandable portion. In that case, the expandable portion can be configured to elute the drug to the patient.

The repair matrix defines a longitudinal axis and may have a plurality of suture channels generally parallel with the longitudinal axis. Each suture passes through at least one of the suture channels.

To deploy, the method may eject the repair matrix from an applicator. After it is ejected, the repair matrix expands to facilitate application.

In accordance with another embodiment, a method of augmenting tissue of a patient secures sutures at two initial points of the patient, and couples sutures through suture channels within a repair matrix defining a longitudinal axis. The suture channels preferably are generally parallel with the longitudinal axis of the repair matrix, which in this implementation has a collagen patch and an expandable member. The method then applies a fluid to the expandable member to expand the expandable member, urging the collagen patch against the tissue. The method also secures the sutures passing through the suture channels to two additional points of the patient to traverse the securing surface of the repair matrix between the two initial points and the two additional points, effectively securing the repair matrix to the patient.

In accordance with yet another embodiment, a surgical expandable member has an expandable portion defining a top surface, a bottom surface, and at least one side surface. The top and bottom surfaces define a thickness of the expandable portion. The expandable portion also has two edges. The member also has at least one suture channel extending through the interior of the expandable portion between the top and bottom surfaces of the expandable portion. The at least one suture channel is at least in part within the thickness of the expandable portion. In addition, the at least one suture channel terminates approximately at or between a) two edges or b) one of the edges and no more than one of the surfaces of the expandable portion. Each suture channel has two open ends sized and configured to receive and pass a suture.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 3 schematically shows a balloon integrated with a patch, according to illustrative embodiments.

FIG. 4 schematically shows sutures integrated with a balloon and patch, according to illustrative embodiments.

FIG. 6 schematically shows an integrated balloon and patch prior to integration with sutures and threaders, according to illustrative embodiments.

FIG. 7 schematically shows an integrated balloon and patch following integration with sutures and threaders, according to illustrative embodiments.

FIG. 8 schematically shows an assembly of threader tabs through medial grommets prior to rolling the integrated balloon and patch, according to illustrative embodiments.

FIG. 9 schematically shows a rolled assembly of the integrated balloon and patch, according to illustrative embodiments.

FIG. 21 schematically shows the balloon over the patch with the combination implant over the tissue, according to illustrative embodiments.

FIG. 22 schematically shows side views of three different implant configurations, according to illustrative embodiments.

FIG. 24 schematically shows implant details for a concept 1.1 technique, according to illustrative embodiments.

FIG. 25 schematically shows implant details for a concept 1.2 technique, according to illustrative embodiments.

FIG. 26 schematically shows implant details for a concept 2.1 technique, according to illustrative embodiments.

FIG. 27 schematically shows implant details for a concept 3.1 technique, according to illustrative embodiments.

FIG. 28 schematically shows implant details for a concept 3.2 technique, according to illustrative embodiments.

FIG. 29 schematically shows implant details for a concept 4.1 technique, according to illustrative embodiments.

FIG. 30 schematically shows implant details for a concept 4.2 technique, according to illustrative embodiments.

FIG. 45 schematically shows filling the balloon with hydrogel, according to illustrative embodiments.

FIG. 46 schematically shows balloon strips to be loaded and inflated on sutures, according to illustrative embodiments.

DESCRIPTION OF ILLUSTRATIVE EMBODIMENTS

Illustrative embodiments relate to a surgical patch enhanced by an integrated or removably coupled expandable member (e.g., a balloon, balloon component, or other expandable item). This combination implant provides improved protection for soft tissue repairs, such as those in rotator cuff surgeries. Unlike traditional designs that occupy the subacromial space, this balloon component closely interfaces with the repair site, harmonizing with its movement across a wide range of motion. Consequently, it establishes a more effective protective environment for the repair site, significantly advancing beyond the capabilities of a standalone patch implant.

Beyond enhancing protection, the balloon component can play an important role in maintaining compression across the patch and tendon tissue at the repair site. Surgeons position sutures and anchors to evenly distribute compressive forces, a task that is significantly supported by the balloon's ability to provide supplemental compression or preload. This additional pressure is important in improving the repair's success, improving the integrity and functionality of the repaired tissue. As such, the pressure is considered to normally urge the patch toward the tissue being repaired, further improving surgical results.

The balloon can serve yet another purpose, functioning not only as protective and support function, but also as a key facilitator in the implant's delivery to the repair site. For efficient deployment, the patch and balloon are compactly compressed, such as being rolled or folded, for insertion via a specialized delivery tool. This balloon-patch assembly then elegantly unfurls or unrolls through controlled balloon inflation. The balloon may remain on site or be removed (i.e., just used in this latter design as a deployment mechanism). This design preferably streamlines the surgical procedure by simplifying device complexity, reducing the demands on the surgeon while leveraging inflation as an innovative means to precisely position the implant over the repair site. Details of illustrative embodiments are discussed below.

Figure 1:
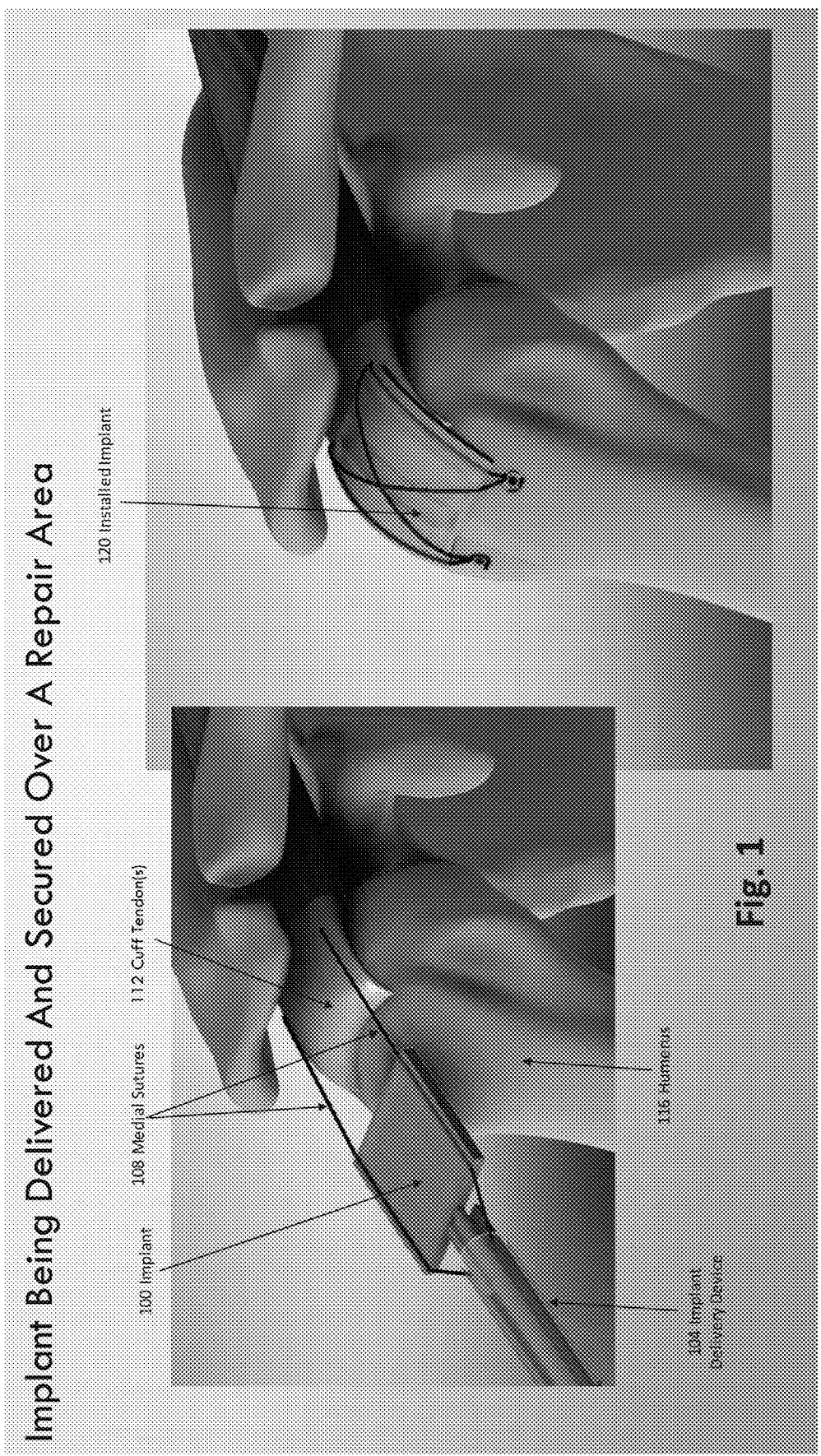
FIG. 1 schematically shows an implant being delivered and secured over a repair area, according to illustrative embodiments.

FIG. 1 schematically shows an implant or repair matrix 100 being delivered and secured over repair area, according to illustrative embodiments. A repair area of a patient may include various tissues, tendons, and bones that define a joint or other bodily area. FIG. 1 shows a shoulder joint, which includes one or more cuff tendons 112 and a humerus 116 (in additions to other tissues, tendons, and bones that may not be directly involved with a repair procedure).

An implant 100 is delivered to the repair area by an implant delivery device 104 used in the repair procedure. The implant 100 may be coupled to one or more medial sutures 108 that are anchored to the cuff tendon(s) 112. Other sutures may be involved with the repair procedure and are described herein.

As known by those in the art, a suture is a medical device used to close wounds or surgical incisions by stitching tissues together for healing. The primary goal of sutures is to hold tissues in place, allowing them to heal properly while minimizing the risk of infection or further injury. Sutures can be made from various materials, such as natural fibers like silk, or synthetic polymers such as nylon or polypropylene. Additionally, sutures are categorized as either absorbable, meaning they dissolve over time and are absorbed by the body, or non-absorbable, which require manual removal once the wound or tissue has healed.

Sutures are also available in different configurations, depending on the surgical needs. Monofilament sutures, for example, are made from a single strand of material, providing a smooth and non-porous surface that minimizes infection risks, often used in cardiovascular surgeries. Braided sutures, such as those made from polyester, are composed of multiple filaments twisted or braided together to offer greater strength and are commonly applied in orthopedic surgeries. Absorbable sutures, such as polyglycolic acid (PGA), are ideal for internal tissue repair, as they naturally break down and are absorbed by the body once healing is complete. Non-absorbable sutures, such as those made from nylon or polypropylene, are used in scenarios requiring long-term support and are typically removed after a set period.

In addition to traditional sutures, there are tape sutures or suture tapes, which are becoming more prevalent in certain surgical applications. Tape sutures often can be ribbon-like, flat materials designed to distribute pressure more evenly across tissues, reducing the risk of tissue damage or cut-through that can occur with narrower, traditional sutures. For instance, suture tape is commonly used in orthopedic procedures, such as ligament repair, minimizing trauma.

FIG. 1 shows an illustration of an installed implant 120 (i.e., a repair matrix 120 having a collagen patch and an expandable member, discussed below) at the completion of the repair procedure (but not necessarily the complete surgical procedure) in accordance with various embodiments. This shows the classic suture cross connection along with sutures traversing through suture channels that are generally/substantially parallel to the longitudinal axis defined by the implant 120 (details below).

Figure 2:
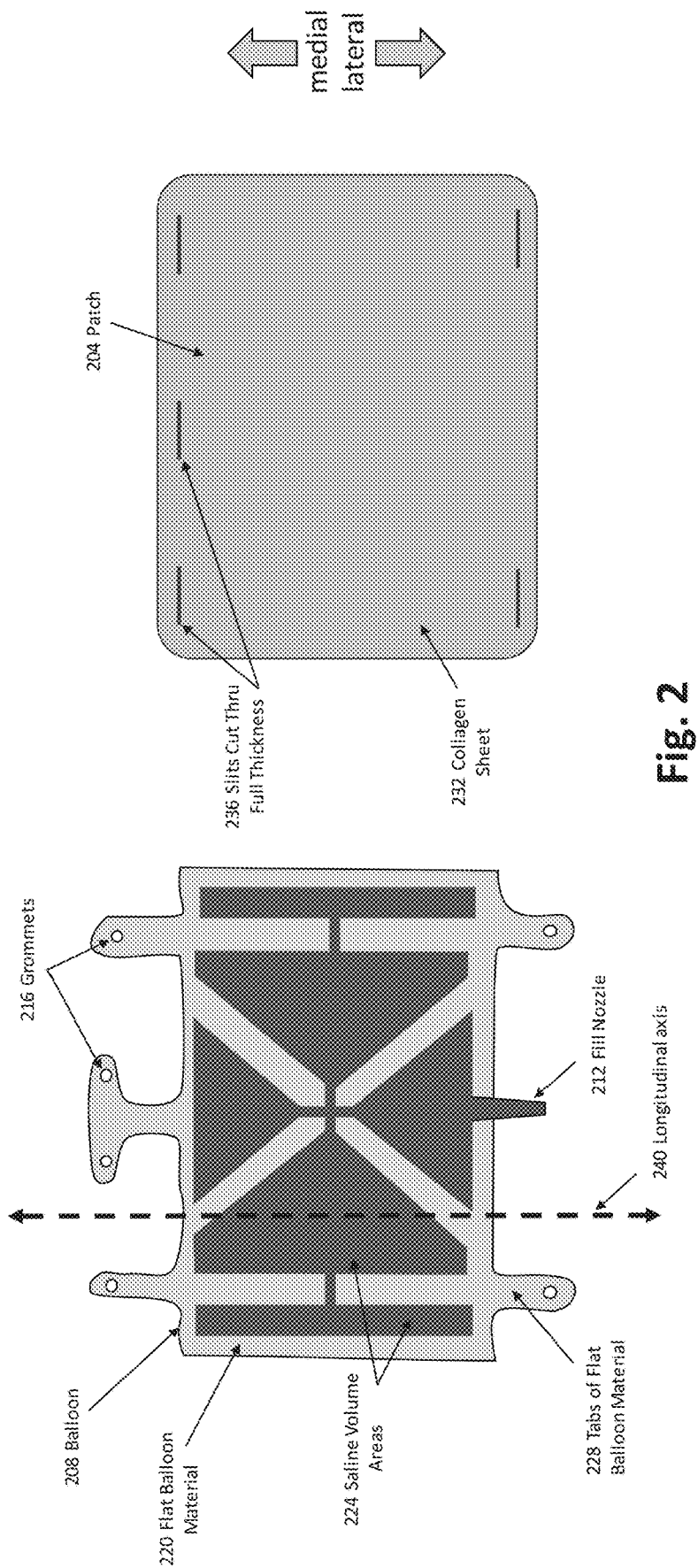
FIG. 2 schematically shows a patch that may be used as a scaffold to facilitate tissue repair or regrowth, according to illustrative embodiments.

FIG. 2 schematically shows a patch that may be used as a scaffold to facilitate tissue repair or regrowth (e.g., rotator cuff repair). It should be noted that although discussion of various embodiments is with regard to rotator cuff repair, other embodiments relate to repair of other tissue in the body. Accordingly, discussion of rotator cuff repair is for exemplary purposes only and not intended to limit all embodiments.

In illustrative embodiments, the patch 204 is a collagen patch formed from a collagen sheet 232. The collagen sheet 232 may include type I collagen fibers having a pore size to facilitate tenocyte infiltration and ECM (extracellular matrix) production. As known by those in the art, a collagen patch 232, in the context of medical applications, may be used in a biocompatible and bioresorbable implant 100 designed to facilitate tissue regeneration and repair. Composed primarily of collagen, an abundant protein in the mammalian body, these patches 204 serve as a scaffold that supports cell migration and proliferation, essential for the healing process. As such, the patch may be considered to be a "scaffold portion" of the implant 120. The collagen matrix of the patch 204 not only provides a structure for new tissue growth but also can be engineered to deliver therapeutic agents such as growth factors, further enhancing the healing process. This approach to tissue repair is particularly beneficial in applications requiring the restoration of complex tissues, such as tendons and ligaments, which have relatively poor intrinsic healing capacities.

In the case of rotator cuff repair, a collagen patch 204 can play a pivotal role in enhancing the surgical outcome, especially in large or complex tears that are challenging to treat with traditional surgical techniques alone. The rotator cuff, a group of muscles and tendons that stabilize the shoulder, is prone to injuries that can lead to pain, weakness, and decreased range of motion. During the surgical repair of a rotator cuff tear, the collagen patch 204 is typically applied over the tendon repair site. It acts as a reinforcing layer that not only mechanically supports the sutured tendon, but also promotes cellular infiltration and tissue integration. Over time, as the body's natural healing processes take over, the collagen patch 204 is gradually absorbed, leaving behind new, healthy tissue. The use of such a patch 204 can potentially reduce recovery time, decrease the likelihood of re-tear, and improve the functional outcomes for patients, making it a valuable tool in the arsenal of orthopedic and sports medicine.

The patch 204 may be formed from a plurality of materials; primarily collagen, e.g., Type I collagen from a bovine source. Additionally, in some embodiments, the patch 204 material can be supplemented with an interwoven or otherwise involved polymer or other biologic material. These polymers have an ability to increase the T=0 and repair duration strength of the patch 204. The patch/scaffold material is configured to progressively integrate (i.e., integrate over time) with the tissue. In similar embodiments, the expandable member is configured to progressively degrade within the body. In preferred embodiments, the patch is configured to integrate faster than an expandable member or expandable portion (see balloon 208 described below) degrades within a patient.

This integration/degradation may be in response to biologic processes within the body after implantation, or other ways. Specifically, as known by those in the art, integration of the collagen patch 204 into tissue occurs through a series of biological processes that promote healing and regeneration. Upon application, the patch 204 adheres to the repair site and initiates the hemostatic process, where platelets form a clot, stabilizing the patch 204 and triggering the inflammatory phase. Immune cells, such as macrophages, clear debris and release signals that recruit tissue-repairing cells like fibroblasts. These fibroblasts and other cells migrate into the collagen scaffold, promoting tissue growth and collagen deposition, while new blood vessels form through angiogenesis to supply the healing site with oxygen and nutrients.

As healing progresses, the collagen patch 204 is gradually degraded by natural enzymes, such as collagenases, while simultaneously being replaced by the body's own extracellular matrix. This matrix remodeling ensures that the patch 204 is progressively integrated into the tissue. Over time, the new tissue strengthens, aligns, and remodels itself, adapting to mechanical stresses and becoming fully functional. The collagen patch 204, therefore, acts as both a structural scaffold and a guide for the body's healing processes, allowing for seamless tissue regeneration. Similar biological processes may degrade the balloon 208 embodiments that degrade.

The supplemental materials could include one or more of the following:
PLA Polylactic cid
PLLA Poly-L-lactic acid.
PLGA Poly Lactic-co-Glycolic Acid
PDLA Poly D-lactic acid
PDLLA Poly-DL-lactic acid
PLDLA Poly (L-co-D, L-lactic acid)
PLCL Poly (L-lactide-co-E-caprolactone)
PDO Polydioxanone
PP Polypropylene
Nylon
UHMWPE Ultra High Molecular Weight Polyethylene In lieu of, or in addition to Type I collagen, the patch 204 may be comprised of the following biologic materials:
Type III collagen
Fibrin
Hyaluronic acid
Allograft or xenograft dermal tissue The patch 204 in this embodiment cooperates with the expandable member 208 to either or both deliver the patch 204 and enhance healing. In illustrative embodiments, the expandable member 208 includes a balloon. For convenience, much of this description refers to the expandable member 208 as a balloon as its modality. However, the expandable member 208 may take on any of a number of different modalities, such as an expandable sponge-like modality, viscoelastic modality, hydrogel, or rigid modalities with individual members that deflect under load. Other examples include semi-rigid frameworks (e.g., analogous to a stent) that establish a macro structure of the expandable member 208 and convert from a collapsed to expanded configuration. Accordingly, discussion of the expandable member 208 as a balloon is not intended to limit all embodiments. In fact, the embodiments using a balloon may be used with other expandable member modalities, including those described above.

As shown, the expandable member 208 has a body. When implemented as a balloon, the body has an inlet for receiving an inflation fluid. This inlet leads to an interior configured to receive the inflation fluid. The volume of fluid in the interior drives the three-dimensional size of the expandable member 208—when fluid exits, the body deflates and gets smaller. When fluid enters, the body inflates and gets larger.

The patch 204 may have a number of slits 236 cut through a full thickness of the collagen sheet 232. In the illustrated embodiment, the slits 236 allow tabs of flattened balloon material 220 to pass through, as will be discussed herein. Alternatively, in another embodiment, the balloon 208 may be at least partially encapsulated within the patch 204. Other embodiments may at least partially encapsulate the balloon 208 within the patch 204.

The balloon 208, designed for use in various medical procedures including orthopedic surgeries (e.g., shoulder repairs), is formed from materials that meet stringent requirements for biocompatibility, durability, and flexibility. Biocompatibility is paramount, as the materials must not elicit any adverse reactions from the body, such as inflammation or rejection. This is typically achieved through the use of medical-grade polymers, such as silicone or polyurethane, which are known for their inert properties and compatibility with bodily tissues and fluids. These materials are carefully selected to ensure they can be safely introduced into the human body for the duration required for the surgery and any necessary post-operative period. In one embodiment, the balloon 208 may degrade within a patient. Preferably, the balloon 208 degrades at a slower rate than that of the patch 204.

Some embodiments use a single balloon or other type of expandable member 208 in the overall system. Other embodiments, however, may use two or more balloons or other types of expandable members 208 in the system. For example, the system may have three elongated balloons side-by-side on their long sides.

The balloon 208, or expandable member, has a length, width, and expanded thickness, the length and width forming a generally rectangular shape. For example, the expanded thickness may have a longest dimension of about 5 to 80% of the width. Typically, the longest dimension, or the length, has a medial end and a lateral end.

Those skilled in the art may form the balloon 208 or other expandable member to be in other shapes and form factors depending on the use. Specifically, when deflated, the balloon 208 may be considered to be somewhat of a two-dimensional shape (e.g., length and width with a much smaller thickness). The balloon 208 may have a three-dimensional shape, however, when deflated and/or when inflated. To that end, one embodiment may shape the balloon 208 to match that of the area of the body being augmented and/or repaired. For example, if the shoulder is being repaired or augmented, the balloon may be shaped in a manner corresponding to the shoulder shape, such as with a concavity for placement on the shoulder. Other examples for shapes include circular, oval, square, irregular, etc., whether as two-dimensional or three-dimensional shapes.

The balloon 208 may be made with specific types of medical-grade polymers due to their strength, flexibility, and compatibility with the human body. In fact, the expandable member 208 may comprise one or more of the materials noted above for the balloon, in whole or in part. Some embodiments of the balloon may contain a PVD or CVD layer or infusion/impregnation of anti-inflammatory or anti-infection agents.

Other balloon materials include one or more of the following:
  Poly (I-lactide-co-E-caprolactone) (PLCL): The copolymer of Lactic Acid and ε-caprolactone—this material may be chosen for implants due to its mechanical strength, degradation profile, and biocompatibility.
  Silicone: Known for its exceptional biocompatibility, silicone is a common choice for surgical balloons. It is flexible, durable, and can be easily sterilized, making it suitable for various medical applications. Silicone's elasticity allows the balloon to be inflated to the desired size without losing its shape or integrity.
  Polyurethane: This material is chosen for its excellent mechanical properties, including strength, flexibility, and abrasion resistance. Polyurethane balloons can withstand higher pressures than those made from other materials, making them ideal for applications where robust performance is required.
  Nylon: Used for its high strength and flexibility, nylon can be manufactured in very thin layers, allowing for compact deflated sizes and precise control over the inflated shape and size of the balloon.
  Pebax® (Polyether block amide): This is a range of polymers known for their flexibility, toughness, and good processing characteristics. Pebax® is particularly valued for its ability to be fine-tuned in terms of flexibility and mechanical resistance, making it suitable for balloons that require specific inflation characteristics.

As noted, these materials are selected for their ability to meet the rigorous demands of surgery, including minimal reaction with tissues, resistance to bodily fluids, and the ability to undergo sterilization processes without degrading. The choice of material often depends on the specific requirements of the surgical procedure, including the need for radiopacity (visibility under imaging), the required pressure and volume of inflation, and the chemical and physical compatibility with the surgical environment and any medications or treatments administered through the balloon 208. For clarity, the medial and lateral sides of the patch 204 and balloon 208 are shown throughout the figures. The medial side faces the interior side of the patient's body, and the lateral side faces the opposite direction.

In addition to biocompatibility, the materials used in surgical balloons 208 possess certain mechanical properties to ensure they perform their intended function effectively. They need to be flexible enough to navigate through tight or complex anatomical structures without causing damage, yet durable enough to withstand the pressures of inflation and the stresses imposed during the surgical procedure. Furthermore, the material should be able to form a hermetic seal when inflated to prevent leakage of air or fluids. The balloon 208 may have one or more surface treatments or coatings that can minimize friction, making insertion and removal smoother and safer. Additionally, although not necessary in many applications, the balloon 208 may be designed to be radiopaque and thus, they would be visible under imaging techniques such as X-Ray or MRI, allowing for precise placement and monitoring during the procedure. These material characteristics collectively ensure that the surgical balloon 208 serves as an effective, safe, and reliable tool in an operating room.

The balloon 208 may be formed as a simple single volume. The balloon 208 may have outside areas of flat balloon material 220 when deflated, inflated, or both. The flat balloon material 220 may include one or more tabs 228 that pass through the slits 236 to facilitate assembly as an integrated unit. The tabs 228 may include grommets 216 that allow suture(s) to pass therethrough to secure the integrated patch 204 and balloon 208 to other bodily structures.

The balloon 208 may also have one or more fluid volume areas, referred to as "saline volume areas 224" (e.g., like camping mattresses, in any number of configurations) coupled to a fill nozzle 212 to facilitate partial or complete inflation of the balloon 208. In one embodiment, the balloon 208 may be configured to contain a saline solution of a sufficient salinity to permit osmotic inflow of water to the volume of the balloon 208. For a balloon 208 having a single saline volume area 224, the balloon 208 may "bulge" in the center although preferred embodiments are more uniform in inflated thickness.

In some embodiments, the balloon 208 structure may be specially configured to inflate to a size and shape that creates a desired profile to perform the desired function (e.g., rectangular). As shown in the figures, sutures secure the balloon 208 in a shoulder or other space of a patient in illustrative embodiments. As such, some or all of the sutures preferably lay over the top of the balloon 208—above cavities with non-filled pathways strategically positioned to create "valleys" for the suture to pass through. This preferably keeps the suture positioning relatively stable.

The balloon 208 and patch 204 preferably cooperate as a single unit. Specifically, in one embodiment, the balloon 208 and patch 204 are integrated together (e.g., fused together or otherwise formed together as a unitary component). Specifically, as known by those in the art, in this context, "integrated" components may be two components that are combined or fused together to form a single, unified member that functions cohesively within the human body. This integration ensures that both materials cooperate to enhance therapeutic outcomes. Among other ways, this may be achieved through various methods like:

Layering or Lamination: Stacking the materials and binding them through adhesives or heat to create a multi-layered structure.

Co-molding or Co-extrusion: Forming both materials simultaneously into a single shape so they interlock at the molecular level.

Chemical Cross-linking: Using chemical agents to create bonds between the molecules of the two materials, resulting in a unified network.

In other embodiments, the balloon 208 and patch 204 are mechanically connected-they are not integral. Specifically, the two members 208 and 204 may be physically joined by various methods but remain distinct components. The balloon 208 may be considered to form a "securing surface" for receiving the patch 204, or vice versa. Examples of various non-integral connections include:

Gluing or Bonding: Medical-grade adhesives can be used to attach the components, creating a secure connection while allowing them to function as a unit.

Mechanical Fastening: Components may be stitched or sutured together, ensuring they remain in place while working together in the body.

Interlocking Design: One component may have features, such as hooks or grooves, that mechanically interlock with the other, providing a stable connection without chemical bonding.

Encapsulation: One material can be wrapped or encapsulated within the other, ensuring the components remain connected while maintaining their structural integrity.

These methods allow the two materials to work together as a unit, where their distinct properties preferably complement one another, such as providing structural support and promoting tissue regeneration, while still being connected through these physical means.

The balloon 208 is configured to receive a securement component such as one or more of a suture, tack, staple, glue, and/or Velcro to couple with the tissue being repaired. One or more of the balloon 208, patch 204, integrated implant 100, and installed implant 120 may define a longitudinal axis 240 proceeding between the lateral and medial sides of the balloon 208, patch 204, integrated implant 100, and/or installed implant 120, respectively. This axis preferably extends along the longest dimension of the balloon 208 or repair matrix 120. However, other embodiments may be considered to form a longitudinal axis along the width when the width is defined by medial and lateral edges. In preferred embodiments, the longitudinal axis extends between the lateral and medial edges of the apparatus, regardless of the sizes of the length and width.

FIGS. 3 and 4 schematically show one embodiment of such an integration. In one embodiment, the patch 204 forms a first footprint and the balloon 208 or expandable member forms a second footprint. As shown in this embodiment, the first footprint preferably is greater than the second footprint.

As assembled, the balloon 208 may be placed on top of the patch 204 without adhesive 304 and the balloon 208 has tabs passed through patch slits 308. This mechanical connection arrangement is shown assembled in FIG. 4, where a suture and grommets 216 are used to arrange the suture in the "traditional" |X| pattern across the top surface of the implant 100. Adhesive optionally may be used to make the connection, whether or not the embodiment has the patch slits.

FIG. 4 shows a medial A-P suture through a medial double tab 416, medial suture tails 404, "91" sutures 412 across a top surface, lateral suture tails, and suture knots 420 on a top surface of the grommets 216.

With the sutures in place and tensioned after being secured at the repair site, the balloon 208 may be configured to allow suture tension to close off and compartmentalize the various segments or volumes 224 of the balloon 208. This may be beneficial over the course of balloon material resorption, as one volume 224 may leak and deflate, while other adjacent volumes 224 remain intact. In this embodiment of the balloon 208 fill configuration, the outer border (two layers of polymer flattened and sealed together) includes four "peninsulas" into the central volume of the balloon 208, designed to create suture valleys once inflated.

Figure 5:
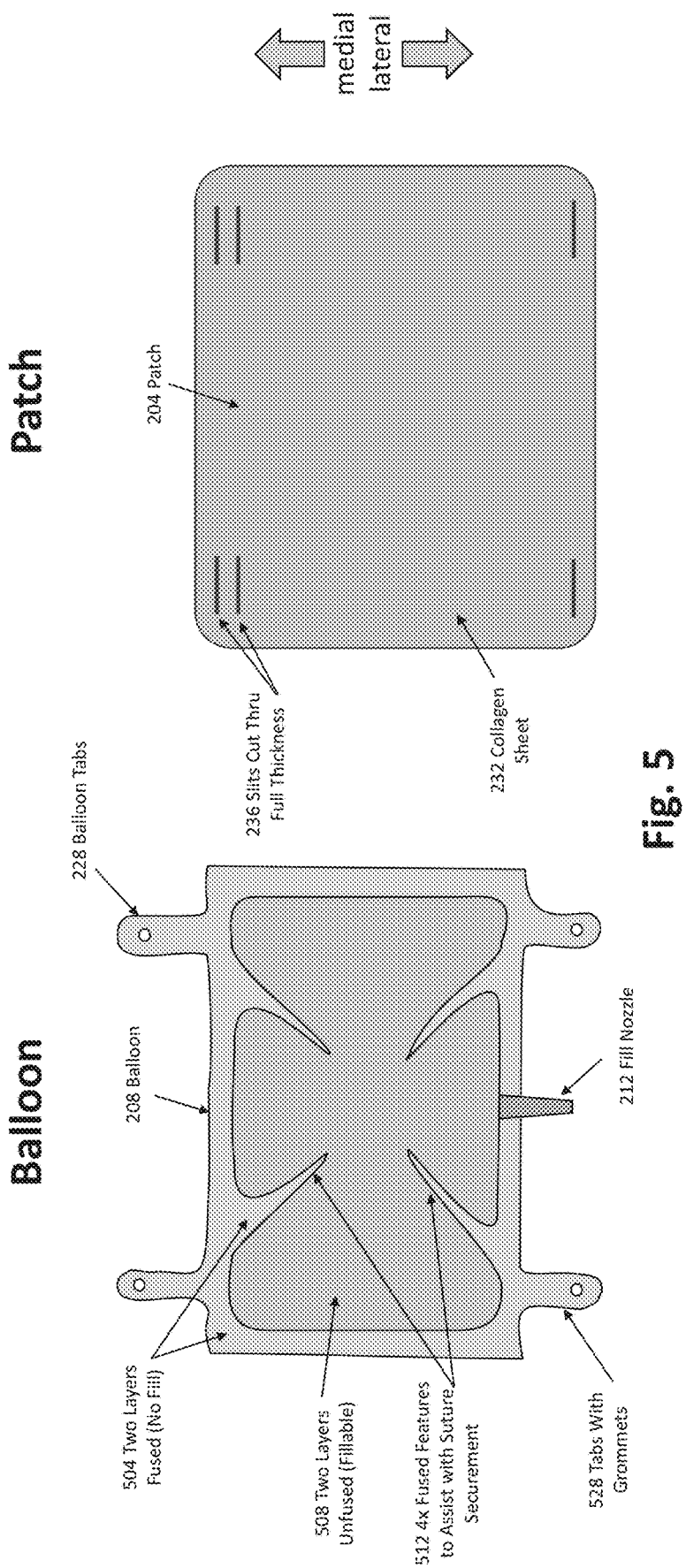
FIG. 5 schematically shows a patch with medially positioned double slits, according to illustrative embodiments.

FIG. 5 shows a patch embodiment with medially positioned double slits 236. This enables (longer) balloon tabs 228 that can be advanced first down through the thickness, then up again before passing over the medial edge. Among other benefits, this arrangement may keep the medial edge of the patch 204 securely (down) against the underlying tissue. As the patient's arm moves through range of motion (e.g., abduction), the medial edge is susceptible to rubbing against the underside of the acromion, pulling on the repair. This exemplary embodiment preferably minimizes the negative effects of these occurrences. Shown in FIG. 5 are the two layers fused 504, the two layers unfused 508, 4× fused features to assist with suture securement 512, and tabs with grommets 528.

FIG. 6 schematically shows an integrated balloon and patch prior to integration with sutures and threaders. As described with reference to FIG. 5, FIG. 6 shows an in and out tab 604 that helps keep the medial edge of the implant down. FIG. 7 schematically shows an embodiment in which the sutures and threaders are loaded onto the implant. Two threaders 704 are fed through grommets 216. Here, the |X| suture pattern is maintained, and the lateral edge of the implant is tensionable with laterally directed sutures (e.g., generally parallel with the length or width of the patch 204 and/or the balloon 208.

FIGS. 8 and 9 schematically show the assembly of threader pull tabs 808 through medial grommets, designed for intraoperative use to facilitate the loading of medial sutures into the implant. Each threader pull tab 808 terminates in a threader kite 804, which provides a loop to capture loose ends of sutures, as described herein. Referring to FIG. 9, prior to the implantation process in a patient, the assembly is prepared for deployment by being either rolled folded in an accordion-like manner, or otherwise generally rolled and collapsed 904. This compact configuration allows it to be easily accommodated within an insertion device, streamlining the implantation procedure.

Figure 10:
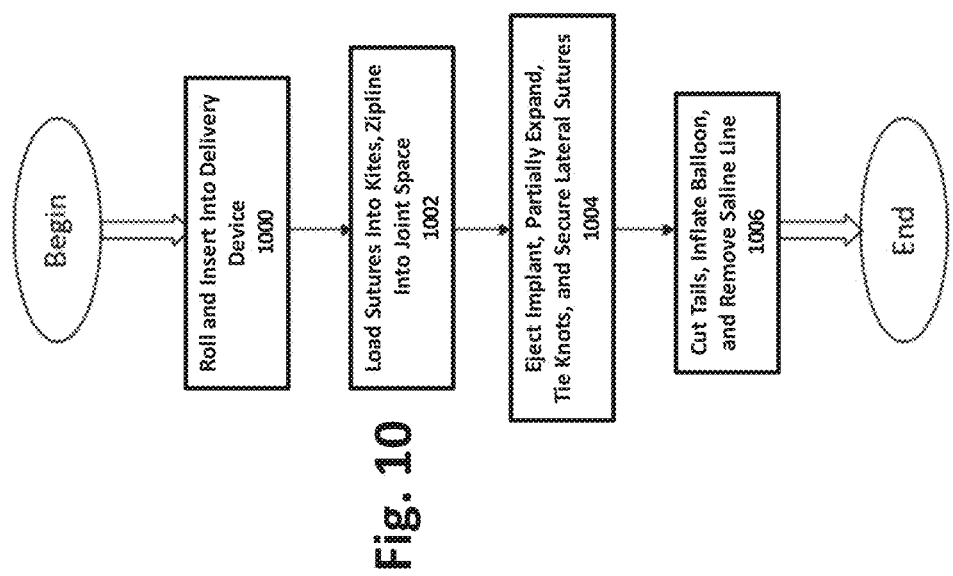
FIG. 10 schematically shows a flowchart of a process of deploying the patch and balloon system, according to illustrative embodiments.

FIG. 10 shows a process of deploying the patch and balloon system in accordance with one embodiment. It should be noted that this process is simplified from a longer process that normally would be used to deploy the patch and balloon system. Accordingly, the process may have additional steps that those skilled in the art likely would use. In addition, some of the steps may be performed in a different order than that shown, or at the same time. Those skilled in the art therefore can modify the process as appropriate. Moreover, as noted above and below, certain materials and structures noted are but one of a wide variety of different materials and structures that may be used. Those skilled in the art can select the appropriate materials and structures depending upon the application and other constraints. Accordingly, discussion of specific materials and structures is not intended to limit all embodiments.

Figure 11:
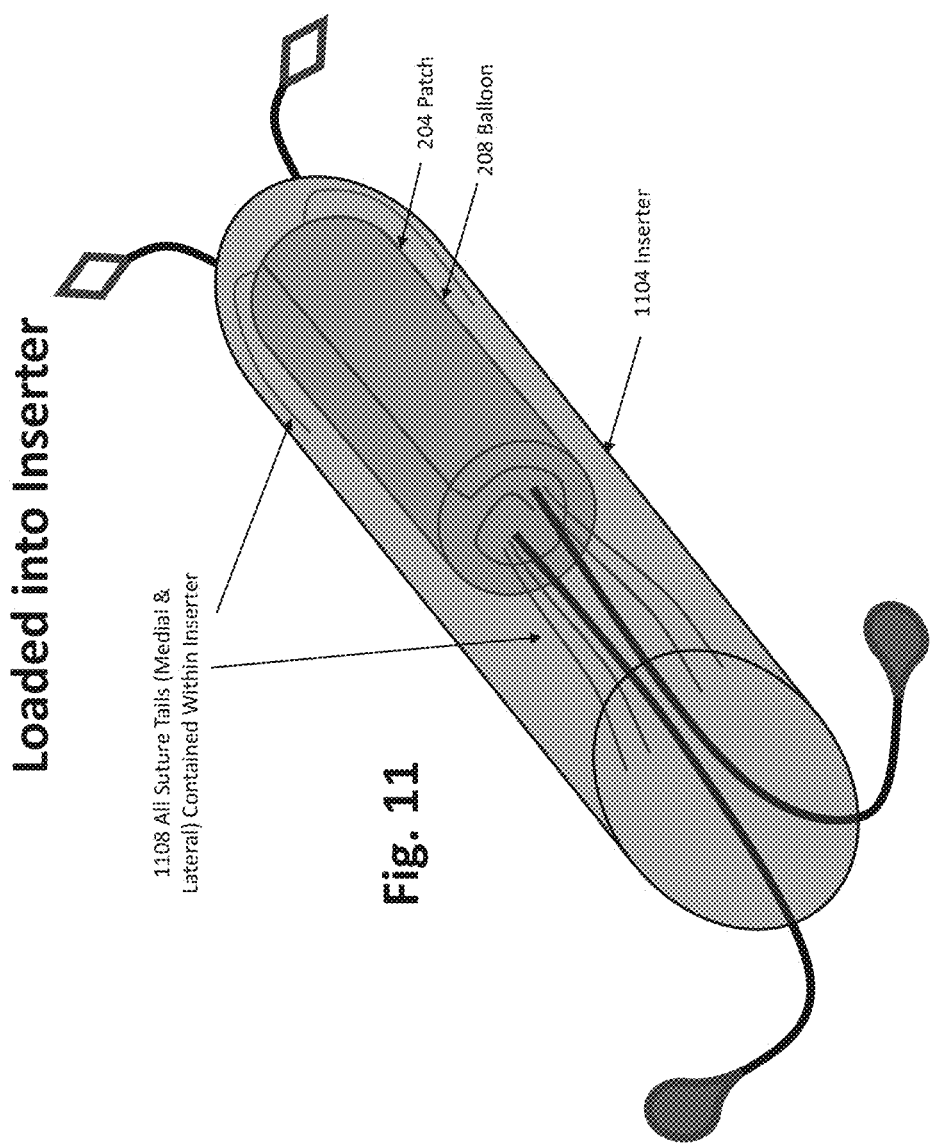
FIG. 11 schematically shows a rolled assembly of the balloon and patch loaded into an inserter, according to illustrative embodiments.
Figure 12:
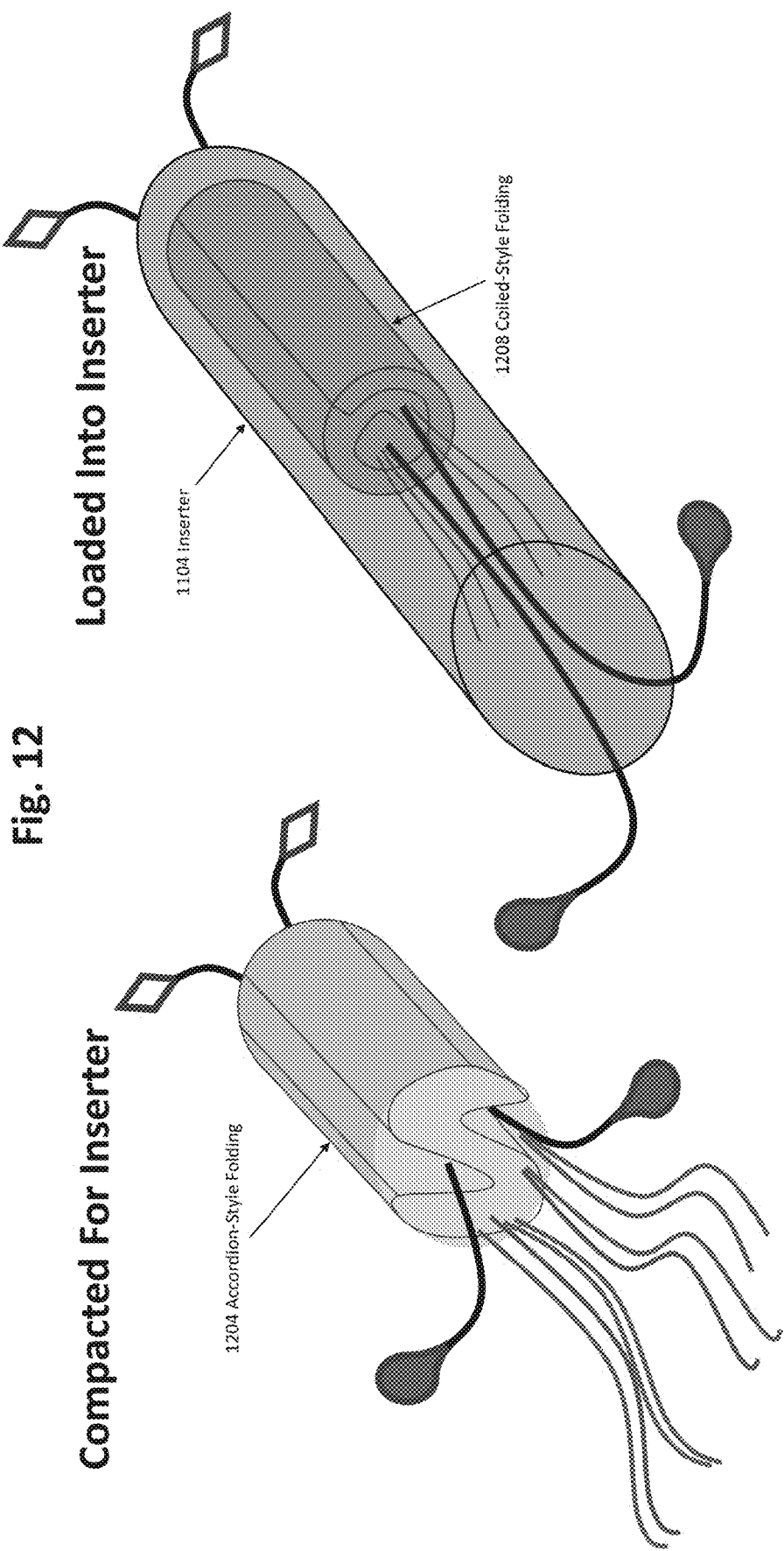
FIG. 12 schematically shows compaction options for the integrated balloon and patch loaded into an inserter, according to illustrative embodiments.

Before starting, one or more sutures are secured to two initial points of the patient. For example, those sutures may be secured to the cuff tendon of a shoulder in a rotator cuff repair. The process begins at step 1000, which collapses and inserts the patch and balloon system into the noted delivery device. FIG. 11 schematically a rolled assembly of the balloon and patch loaded into an inserter 1104. In illustrative embodiments, the assembly (patch 204 coupled to balloon 208) is rolled, with suture ends extending axially outward. The assembly is placed within the inserter 1104, and all suture tails (medial and lateral) are contained within the inserter 1108. FIG. 12 schematically shows compaction options for the integrated balloon and patch loaded into an inserter 1104. For example, the assembly may be folded using accordion-style folding 1204 or rolled using coil-style folding 1208.

Figure 13:
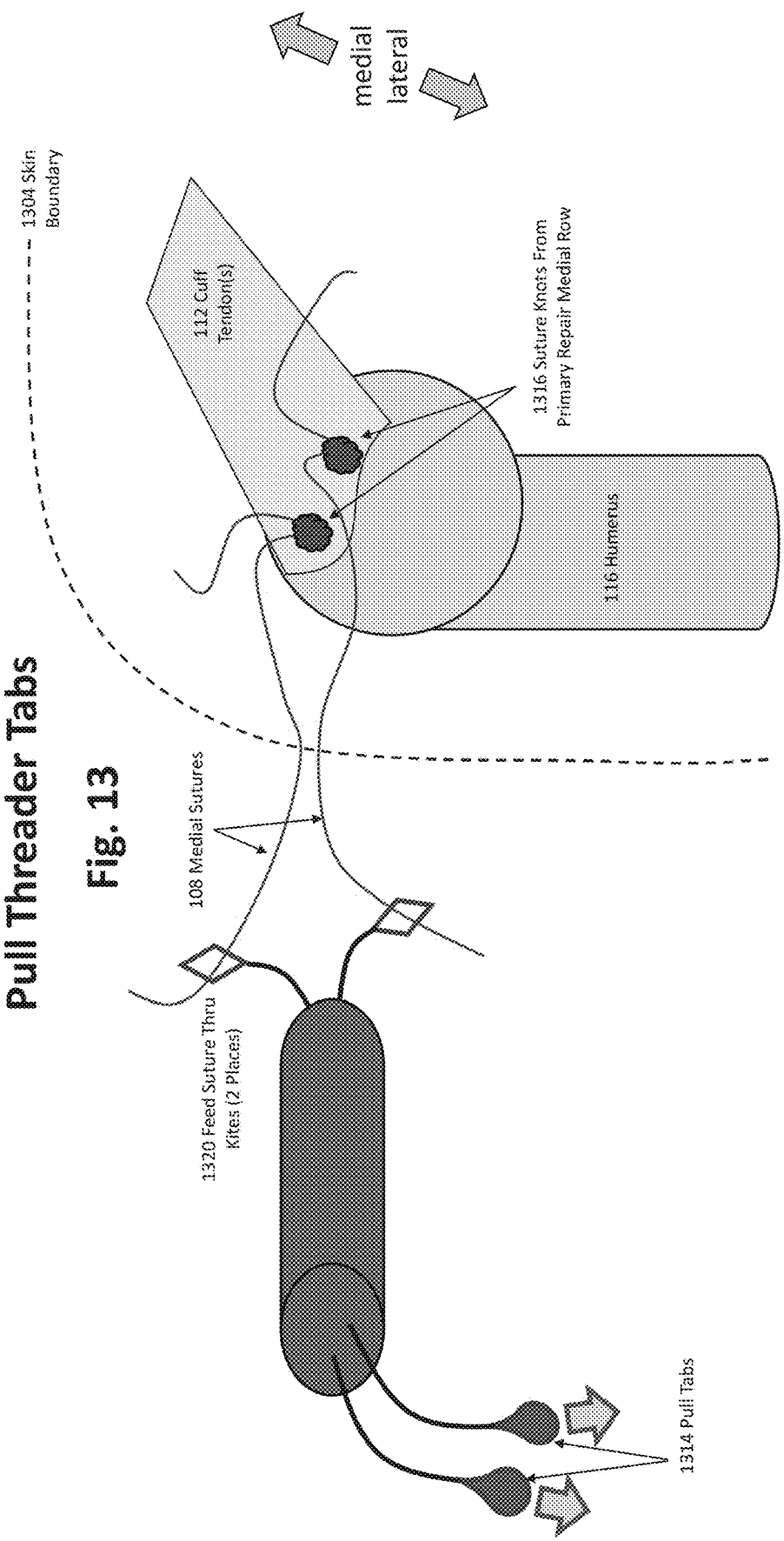
FIG. 13 schematically shows medial sutures loaded into kites and secured with pulled threader tabs, according to illustrative embodiments.
Figure 14:
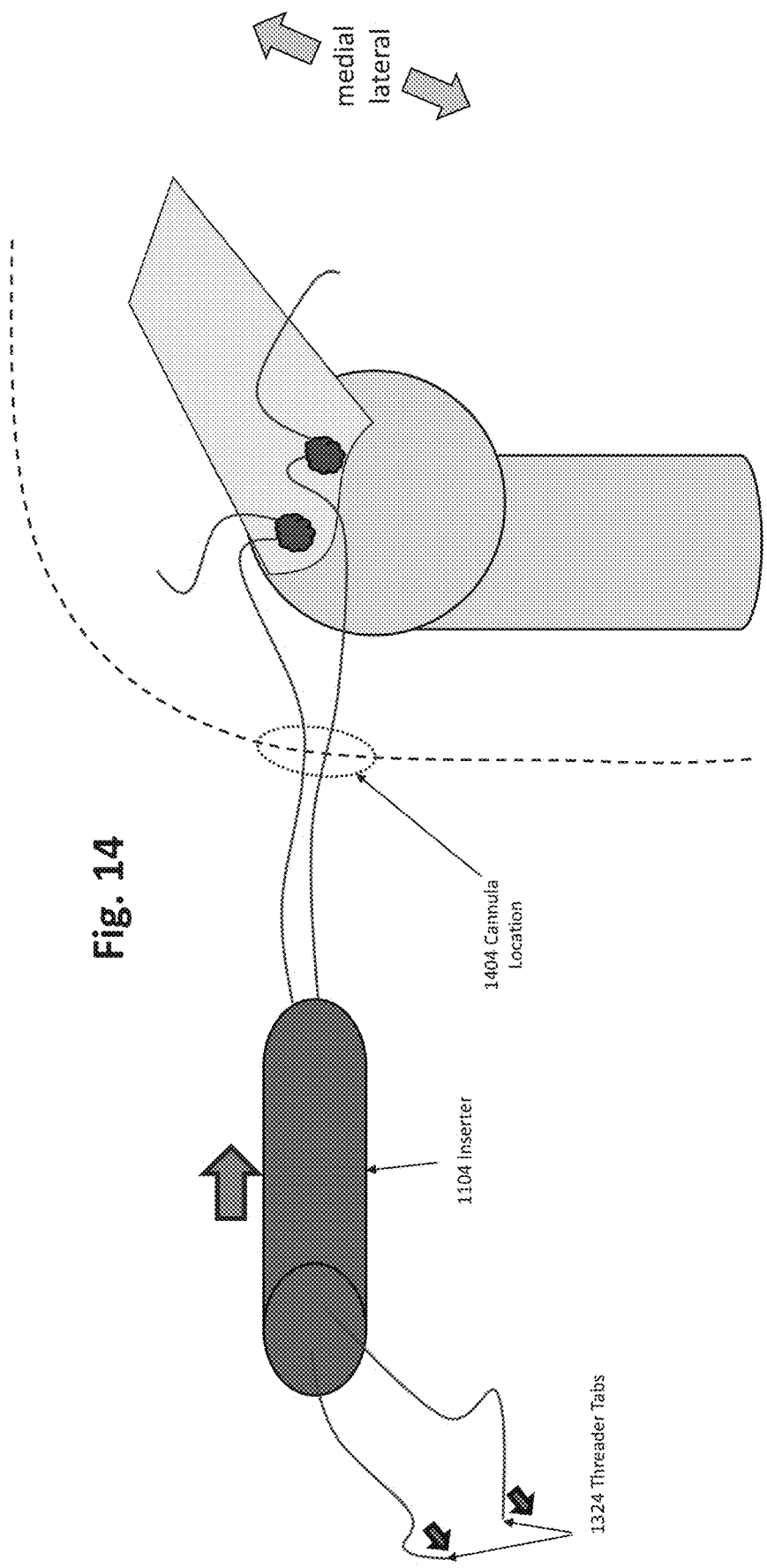
FIG. 14 schematically shows a zipline inserted within a joint space, according to illustrative embodiments.

Next, step 1002 feeds sutures already coupled with two initial locations on the patient into threading kites 1320 at two locations. Specifically, prior to this step, the surgeon secures at least two sutures to the two initial locations on the patient-in this example, in the tendon. The surgeon then ziplines the system into the joint space by pulling on the pull tabs 1324. FIGS. 13 and 14 demonstrate one embodiment of this step. FIG. 13 schematically shows medial sutures loaded into kites 1320 and secured with pulled threader tabs 1314.

As shown, a cuff repair to cuff tendon(s) 112 to the humerus 116 beneath a skin boundary 1304 has already taken place, leaving medial suture tails available for incorporation into the balloon and patch system. The suture shown in red includes suture knots from the primary repair medial row 1316.

Other options, not shown, may include:
Repair complete, additional free sutures passed through cuff medially,
Repair not needed (partial tear laterally, no tear at all), free sutures passed through cuff medially, and/or
Repair not completed, cuff cannot reapproximate to humeral head, free sutures passed through edge of cuff.

FIG. 14 schematically shows a zipline inserted within a joint space. The surgeon may pull the threader tabs 1324 to load the operative sutures into the implant 100. Also, as known by those in the art, "ziplining" in arthroscopic rotator cuff repair typically is referred to as the act of holding tension on suture(s) and advancing something (loaded onto said suture(s)) into the repair site on the tensioned suture(s). Not shown in FIG. 14 is a cannula (see cannula location 1404) used to facilitate this arthroscopic procedure. Moreover, the inserter 1104 may be designed to function in conjunction with a custom cannula. This could facilitate positioning, suture management, tensioning, balloon inflation, etc.

After it is ziplined, step 1004 ejects the implant (i.e., the repair matrix 120), at least partially expands the balloon 208, ties knots to secure the repair matrix 120 to the region around the rotator cuff, and secures lateral sutures to two additional locations on the patient (e.g., using surgical anchors). More specifically, the deployment of a balloon and collagen patch system represents a sophisticated method of deploying the patch 204 and enhancing the repair and healing of damaged shoulder tissues. Step 1004, a critical phase in this process, involves the ejection of the implant 100 into the targeted area. At this juncture, the balloon 208 is at least partially expanded—and at least partly applying a force to the patch 206, which urges it toward the tissue to be repaired. Following the strategic placement and partial expansion of the balloon 208, the system is secured within the shoulder's complex anatomy. Knots are tied to ensure that the balloon and collagen patch system is firmly anchored to the region around the rotator cuff. This securing process is important for maintaining the integrity of the repair site, particularly in the dynamic and mechanically demanding environment of the shoulder. Additionally, lateral sutures are placed, further stabilizing the system. These sutures not only reinforce the attachment of the balloon 208 and patch 204, but also facilitate the integration of the collagen patch 204 with the native tissue by applying a more consistent bias/urging against the tissue being repaired.

FIGS. 15-18 schematically show one example of step 1004. In these examples, the deployment device (aka "inserter 1104") may be designed with a "plunger" (not shown) that pushes forward (arrow direction), or, said differently, the outer sheath of the inserter could retract, exposing the implant 100 in its coiled/compact state. Moreover, as suggested above, the balloon 208 may be semi or fully inflated to unfurl it from its compact state.

Figure 15:
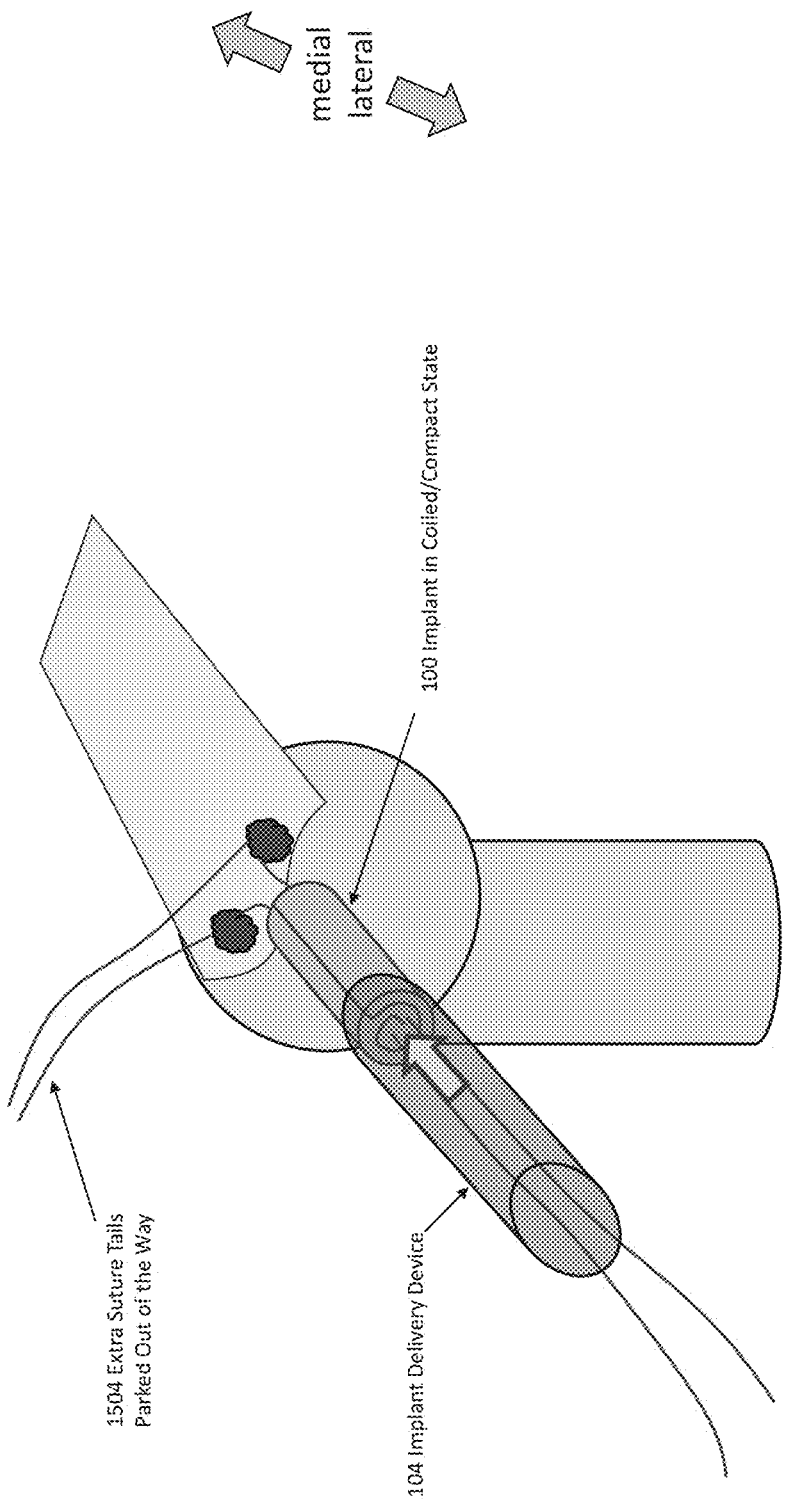
FIG. 15 schematically shows an implant ejected from an inserter, according to illustrative embodiments.
Figure 16:
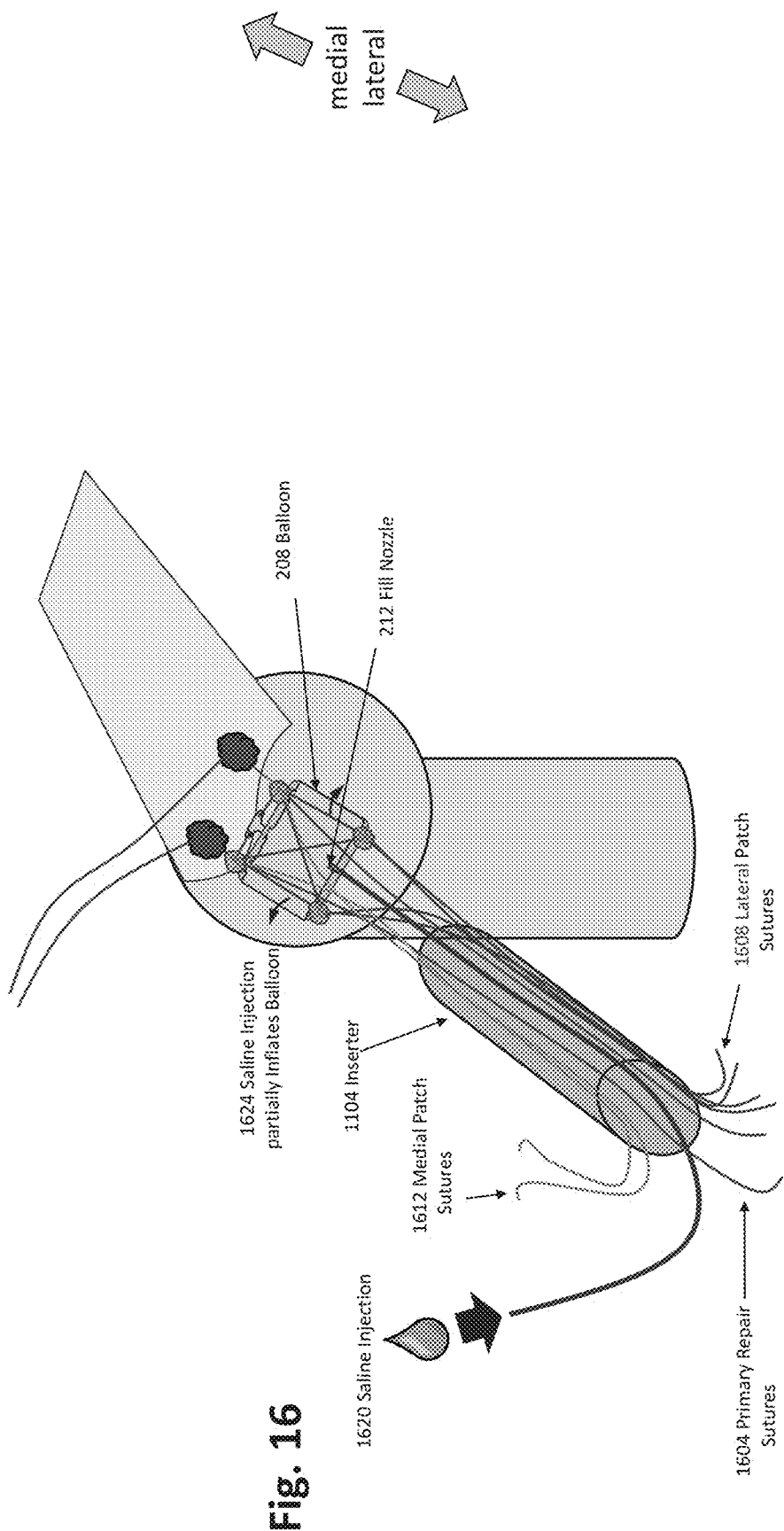
FIG. 16 schematically shows partial inflation of the balloon to unfurl the integrated balloon and patch, according to illustrative embodiments.

FIG. 15 schematically shows an implant ejected from an inserter 1104. Extra suture tails 1504 are parked out of the way. FIG. 16 schematically shows partial inflation of the balloon 208 to unfurl the integrated balloon 208 and patch 204—making it more flat configuration than when initially ejected from the deployment device/inserter 1104. The sutures (in this embodiment) may be, at this point (e.g., FIG.

16), available to the surgeon for incorporation into the repair. This relative complexity could be mitigated by combining subsets of the suture limbs in small flexible tubes (e.g., by analogy, like a coffee stirrer). In this way, the exposed sutures would be instead minimized to only a small number of "straws". FIG. 16 shows the primary repair sutures 1604, the lateral patch sutures 1608, the medial patch sutures 1612, saline injection 1620, and saline injection to partially inflate the balloon 1624. Saline enters the balloon 208 through the fill nozzle 212 and is prevented from exiting the fill nozzle 212 by an integrated low-profile backfill preventer feature that does not use plugs for saline retention.

In one embodiment, the saline line has a connection to a syringe that provides saline to the balloon 208 to inflate the balloon 208. In one embodiment, the connection between the saline line and syringe and/or the saline line and the fill nozzle 212 may be an interference fit. In one embodiment, a system may include a tube terminating at a luer fitting or luer lock. The tube may be in fluid communication with the balloon 208 and the luer may be configured to receive a luer-standard pressure device. In one embodiment, a luer lock may provide a secure connection between the syringe and the saline line and/or between the saline line and the fill nozzle 212. In one embodiment, the 1104 inserter may be sized with an inner cannula to allow a standard luer lock to pass therethrough.

Figure 17:
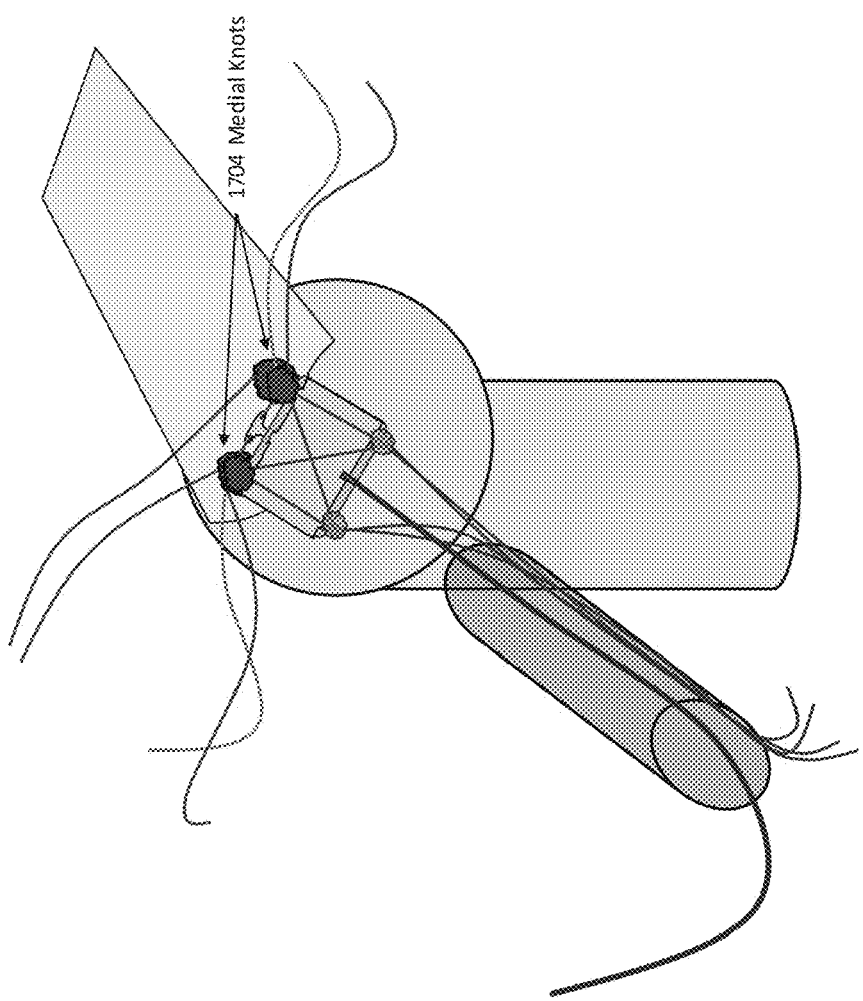
FIG. 17 schematically shows medial knots tied to secure a medial edge of an implant, according to illustrative embodiments.
Figure 18:
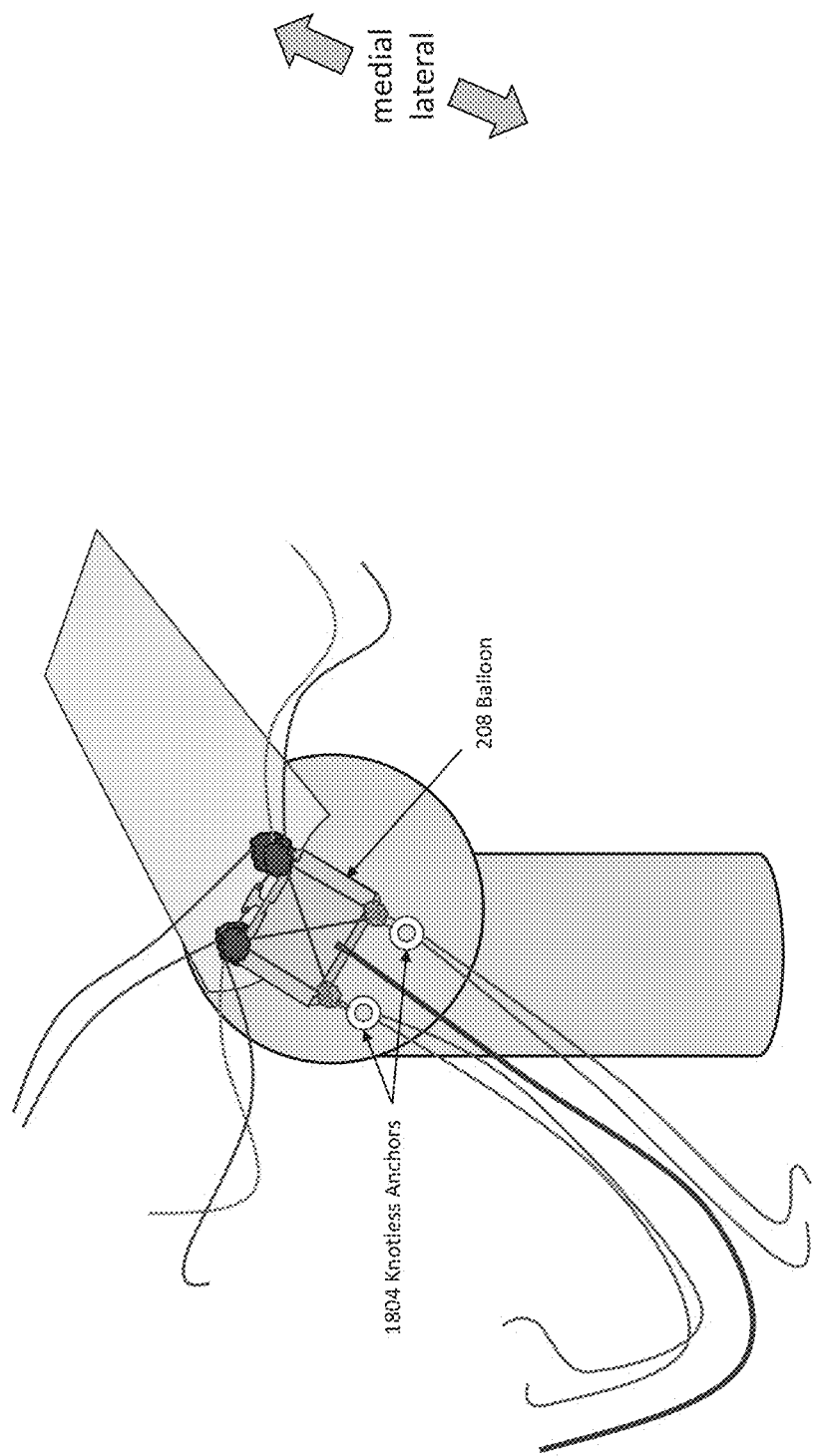
FIG. 18 schematically shows lateral sutures secured with knotless anchors, according to illustrative embodiments.

As shown in FIG. 17, expanding on the securement noted above, the implant securement may tie the medial corners to the underlying tissue 1704. FIG. 18 shows the lateral edge may be secured by incorporating the lateral suture limbs (and any sutures passed over the top of the balloon 208) into lateral knotless anchors 1804.

Figure 19:
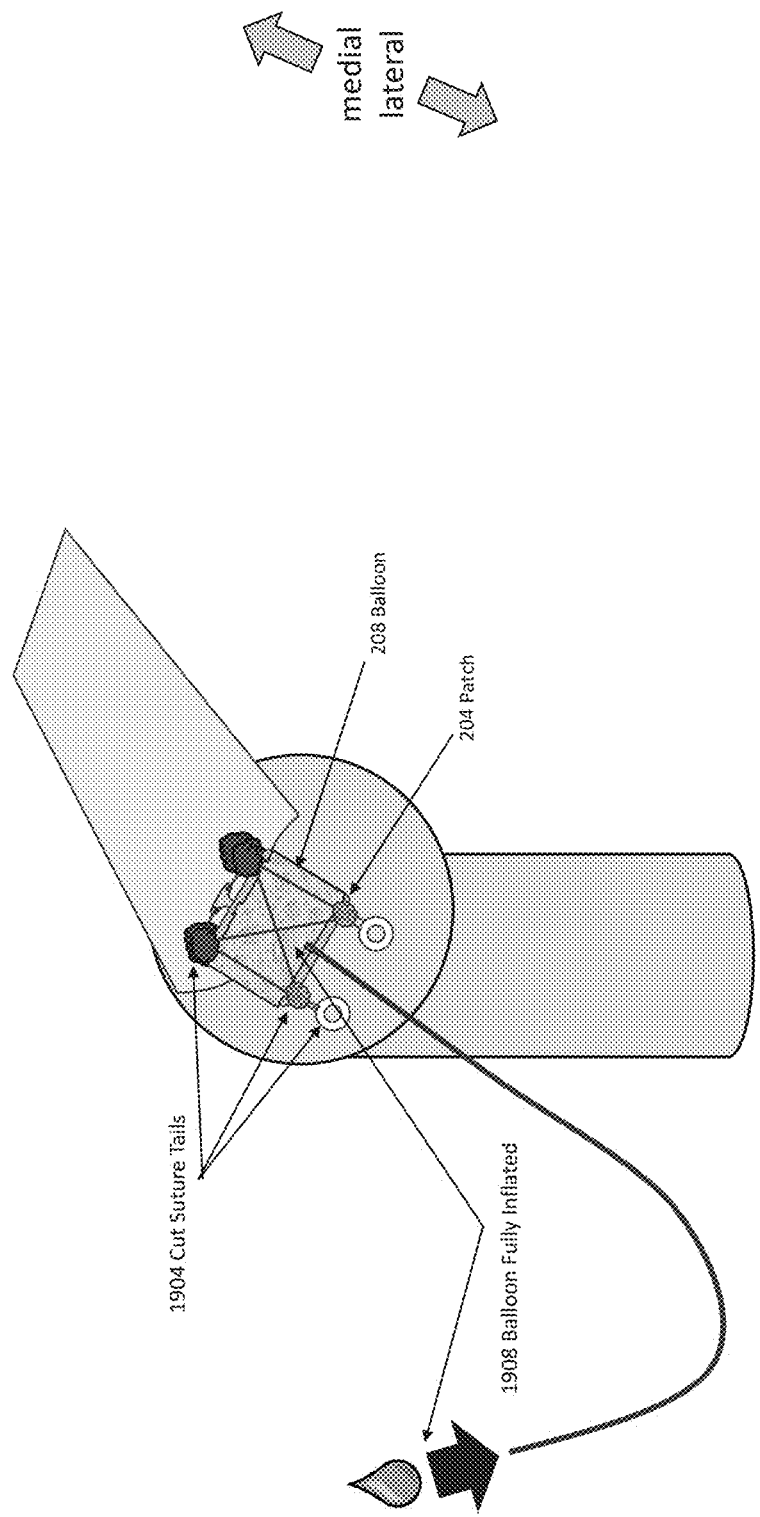
FIG. 19 schematically shows the sutures cut and the balloon inflated for an installed implant, according to illustrative embodiments.

The culmination of the exemplary intricate rotator cuff repair process is marked by step 1006, executing a sequence of actions designed to finalize the implantation and ensure the stability of the repair. This step begins as shown in FIG. 19 with the careful cutting of the suture tails 1904, a task performed with precision to prevent any loose ends that could potentially irritate or damage the surrounding tissue. Cutting the suture tails 1904 signifies the completion of the securing phase, where the balloon 208 and collagen patch 204 have been successfully anchored to the rotator cuff region.

With the structural components now firmly in place, attention turns to the final adjustments of the balloon implant to optimize the surgical outcome. Following the trimming of the suture tails 1904, the balloon is fully inflated 1908. This inflation 1908 is an important step, as it expands the balloon 208 to its predetermined size. The full inflation of the balloon 208 ensures that the collagen patch 204 remains in optimal contact with the tissue, providing a scaffold for new tissue growth. In illustrative embodiments, the balloon 208 acts as a bias for normally urging the collagen patch 204 against the repaired tissue. The inflation process is carefully monitored to achieve the correct pressure and volume, ensuring that the balloon 208 provides adequate support without causing undue stress on the tissues.

Figure 20:
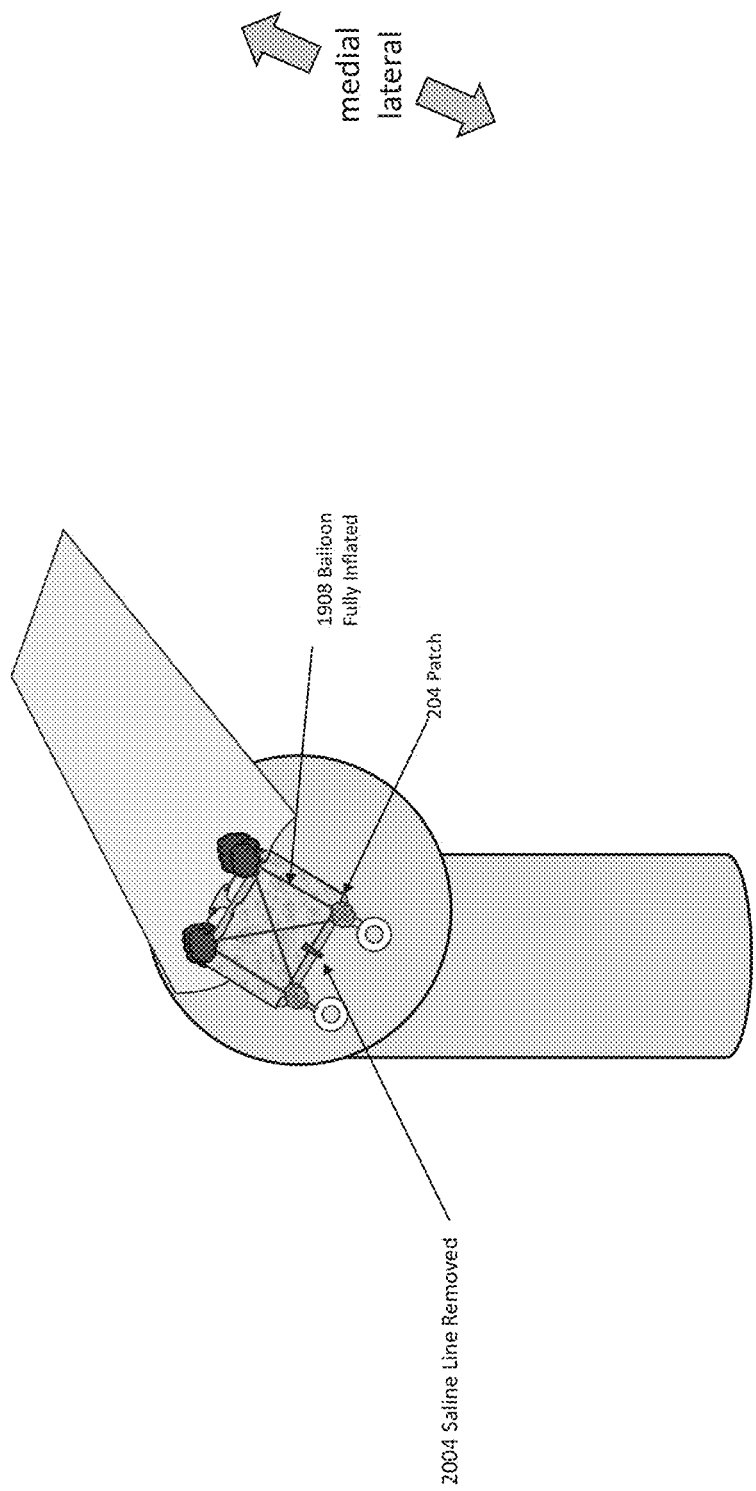
FIG. 20 schematically shows a saline line removed from the installed implant, according to illustrative embodiments.

As shown in FIG. 20, after the balloon is fully inflated 1908, the saline lines, which are used for the inflation process, are carefully removed 2004. This removal marks the end of the surgical intervention, leaving the balloon 208 and collagen patch 204 in place to support the healing of the rotator cuff. The combination of these advanced materials and techniques represents a forward-thinking approach to orthopedic surgery, aiming to improve healing rates, reduce recovery times, and ultimately enhance patient outcomes in rotator cuff repairs.

Both the patch 204 and the balloon 208 preferably are absorbed into the body as they are left in place. However, some embodiments may secure the patch 204 and remove the balloon 208—only using the balloon 208 as a patch deployment device. FIGS. 20-23 schematically show the balloon 208 and patch 204 at this stage.

FIG. 21, for example, shows the balloon 208 over the patch 204, with the combination installed implant 120 over the tissue. FIG. 22 shows three different embodiments from a side view. The embodiment described in FIG. 21 is shown as embodiment 1 in this Figure. Embodiment 2 of this Figure shows two layers of patch 204 material closed/connected laterally. This embodiment also can be formed as separate components. In this case, there may be one patch 204 below the tissue and the balloon-patch implant (itself the same as embodiment 1) may be secured over the top of the tissue. For the third embodiment in FIG. 22, two layers of patch material 204 can be closed/connected laterally (as shown), or they can be separate components. In this case, there may be one patch 204 below the tissue, and in a separate insertion/implantation, the balloon-patch implant (itself the same as embodiment 1) may be secured over the top of the tissue. Embodiment 3 also may be considered to form a receiving region to receive the balloon and therefore at least partially encapsulate the balloon.

Figure 23:
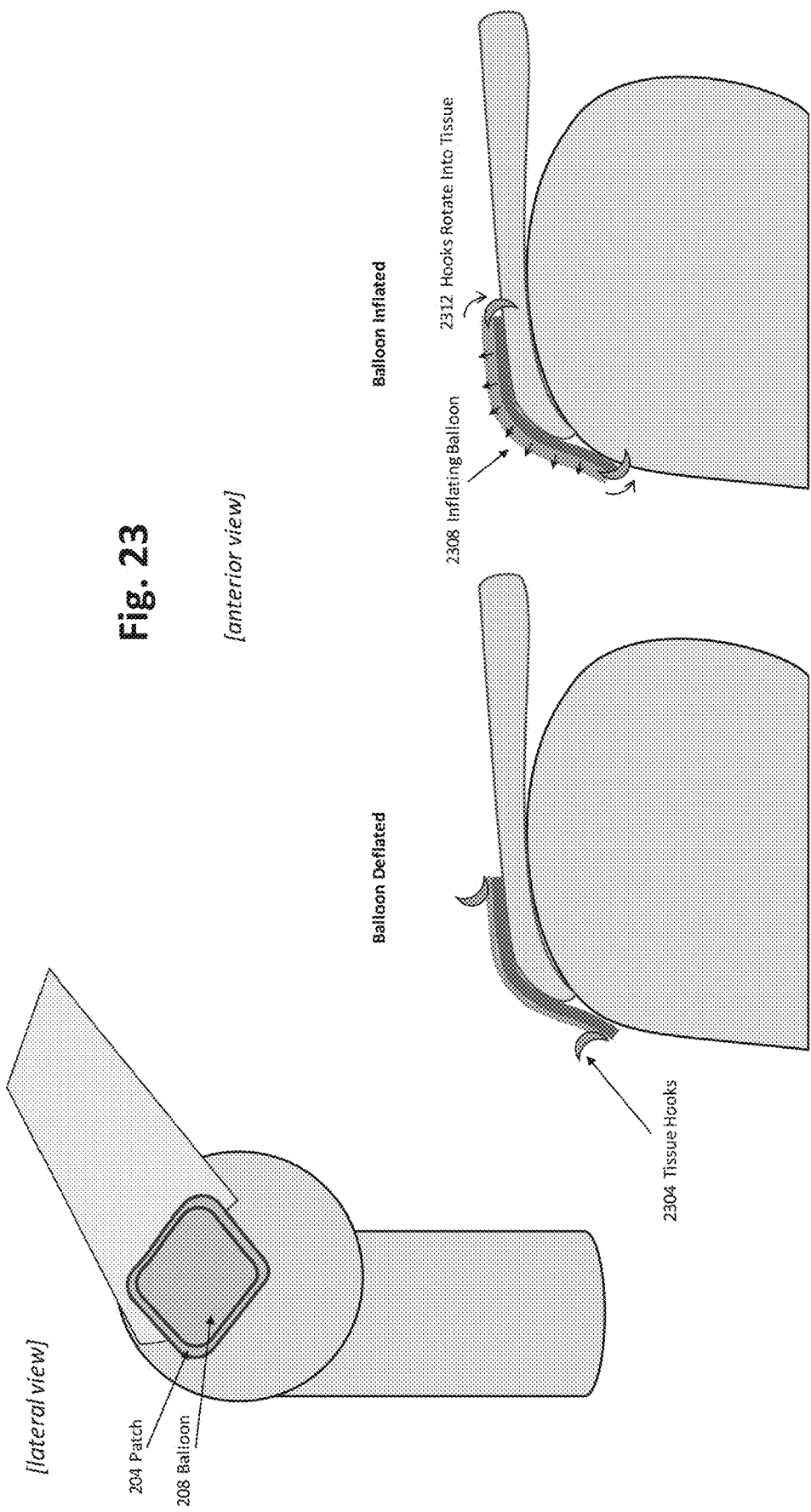
FIG. 23 schematically shows three anterior views of a suture free implant technique, according to illustrative embodiments.

FIG. 23 schematically shows a suture-free (theoretically, sutures could be used as supplemental fixation) implant fixation technique. As shown in this embodiment, the balloon 208 has tissue "hooks" 2304 molded/formed into the balloon material itself. In the delivered deflated state, the hooks 2304 are inactive, interacting with nothing. As the balloon fills with fluid, such as saline 2308, the hooks rotate downward to engage with tissue 2312 (both tendon and possible bone), anchoring the balloon 208 (and with it, the patch 204) to the repair site. The medial hooks 2304 shown in FIG. 23 are on the medial edge of the implant. Not visible are hooks around the periphery of the balloon 208, including the anterior and posterior borders of the balloon 208.

FIGS. 24-30 schematically show other configurations of suture in the assembled implant 100, and how they may exist after the implantation procedure is complete 120. Some figures have descriptive text summarizing various embodiments. In these or other embodiments, sutures that tie down the medial edge of the implant (originating from the tissue below) can be cut for simplicity (Concept 1.1, FIG. 24) or passed over the top of the implant for additional security (Concept 1.2, FIG. 25). FIG. 24 shows lateral knotless anchors 1804, the knots from the repair 2404, knots tied during the patch/balloon procedure 2408, "X" sutures encouraged to stay in the "X" pattern because of the fill profile 2412, tails 2416, and up-down sutures may bulge slightly outward because of the fill profile. FIG. 25 shows an additional "IXI" suture from the medial sutures.

FIG. 26 (Concept 2.1) shows how an embodiment with no included sutures over the top of the implant, so the operative suture tails would likely be passed over (not cut) and secured laterally. In FIG. 27 (Concept 3.1), the "X" suture is shown as an "infinity" loop, but may require a knot somewhere 2704. Additionally, the sutures interlock each other, as well as with the grommet 2708. In FIG. 28 (Concept 3.2), the "X" suture is also shown as an "infinity" loop and the medial tails are laterally secured. In FIG. 29 (Concept 4.1), the sutures are formed in an "IXI" pattern, the medial tails are cut, and the lateral loops may be adequate for tensioning the lateral edge of the implant when they tighten around the tabs. FIG. 29 shows the suture is looped around and through the grommet 2904. In FIG. 30 (Concept 4.2), the sutures are formed in an "IXI" pattern, and the medial tails are laterally secured.

Figure 31:
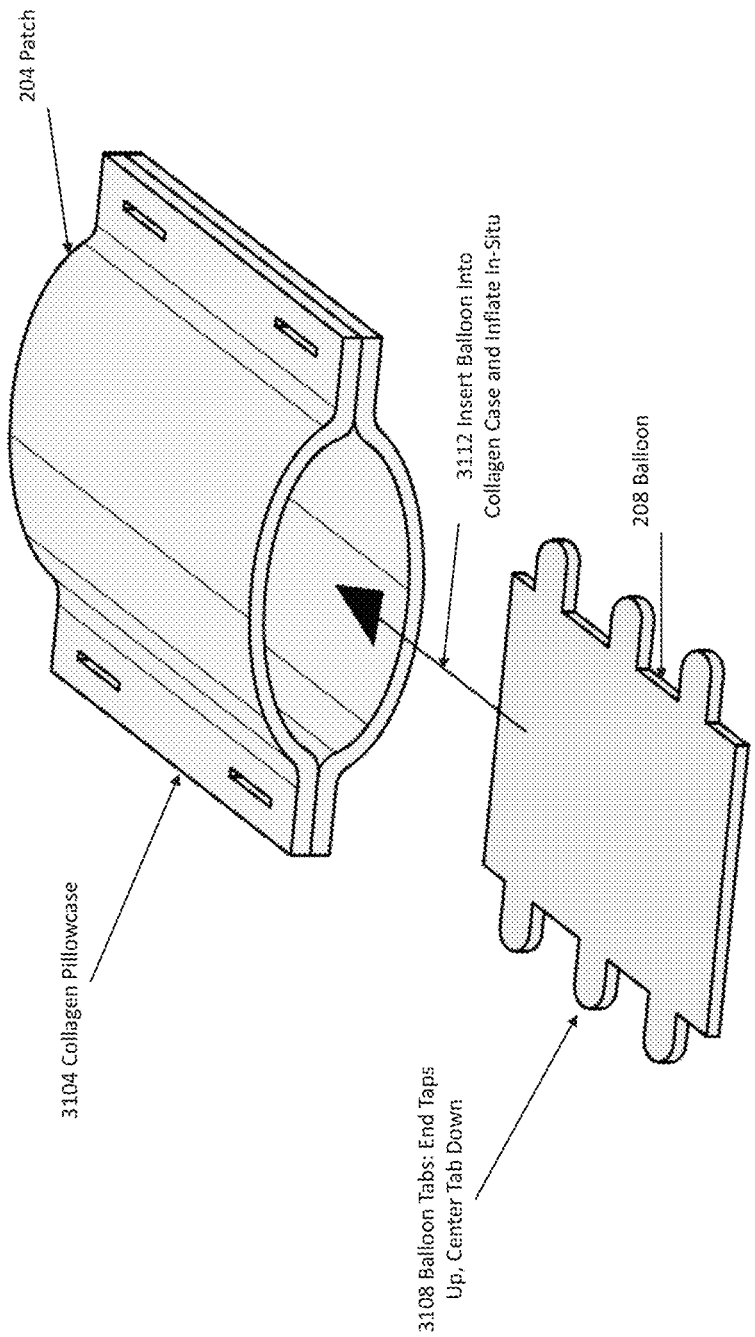
FIG. 31 schematically shows a form factor where the balloon is designed to fit into a collagen pillowcase, according to illustrative embodiments.

The versatility of the balloon 208 and patch 204 design allows for a variety of form factors beyond the noted configurations, enhancing its adaptability to specific medical needs. For example, FIG. 31 illustrates a unique form factor where the balloon 208 is designed to fit into a bore or internal space formed by collagen sheets/patches (essentially formed as a single, unitary patch 204), creatively termed a "collagen pillowcase" 3104 in the drawings. In this arrangement, the balloon 208 finds itself snugly encapsulated on two or three sides within this specially designed void. The Balloon 208 may include three tabs on each of the medial and lateral sides, with 2 tabs bent upward and one tab bent downward 3108. The balloon 208 is inserted into a collagen case, assembled, and inflated in-situ 3112. Such a design may provide a secure and stable environment for the balloon 208, optimizing its functionality and therapeutic efficacy by ensuring it remains precisely positioned within the treatment area.

Some embodiments take the idea of encapsulation even further by surrounding the balloon 208 entirely on all four sides, creating a fully enclosed space within the collagen structure. This solution leaves only a minimal opening necessary for the saline or inflation channel, ensuring that the balloon 208 is both protected and effectively integrated into the surrounding tissue. The introduction of tabs 3108 on the balloon 208, as depicted, offers additional structural benefits and aids in the secure placement and potential adjustability of the implant 100 within the body. Such design considerations highlight the potential for customization and flexibility in addressing a range of surgical requirements and patient-specific needs.

Beyond the described configurations, various embodiments can be implemented with other form factors, indicating a rich field of innovation within implant design. The examples provided are merely illustrative of the broad spectrum of possibilities, underscoring the potential for future advancements in medical technology. Various embodiment is designed with the intention of improving patient outcomes through targeted delivery, structural support, and integration with biological tissues.

Figure 32:
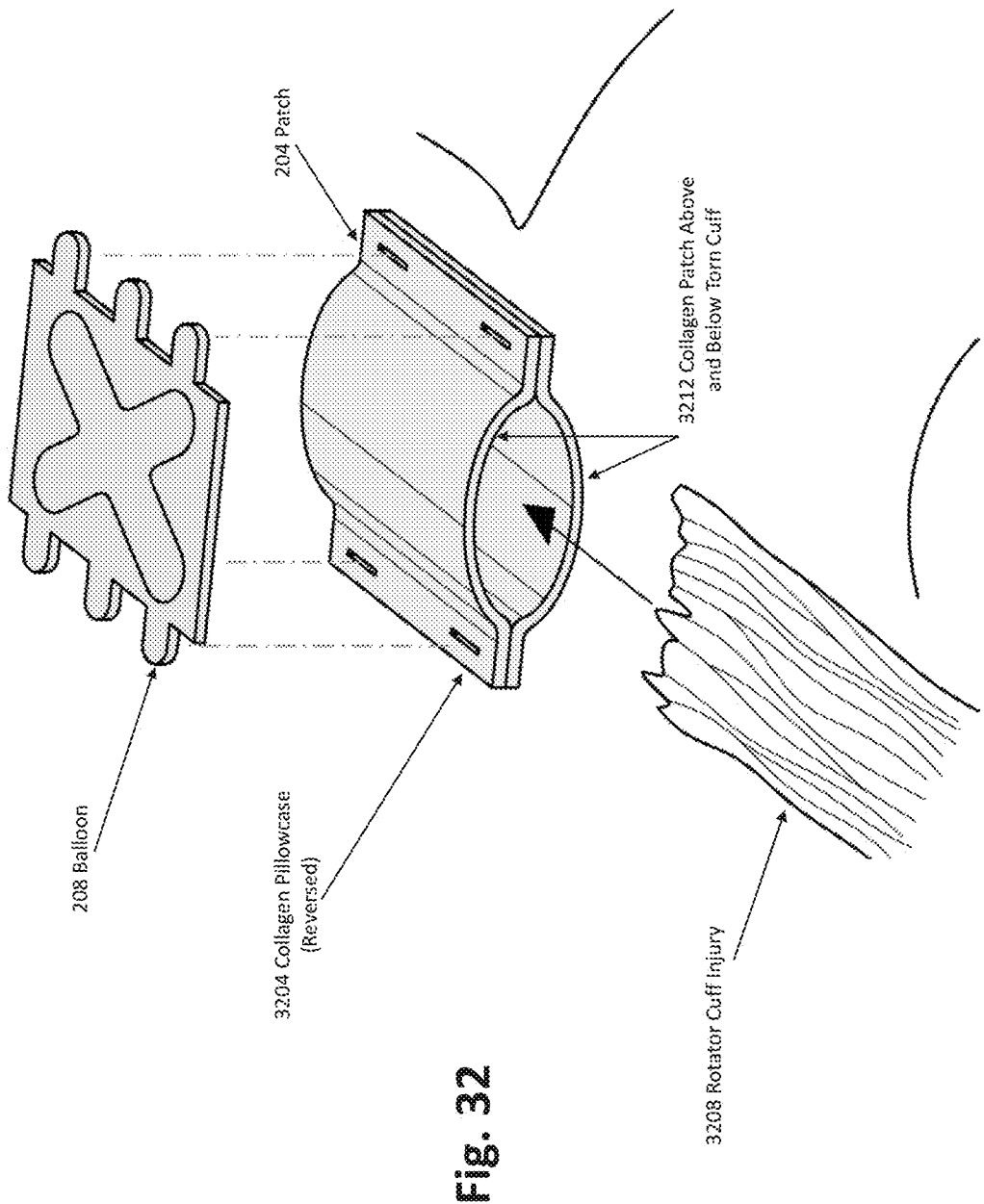
FIG. 32 schematically shows a strategically positioned damaged cuff within a void created by the patch, and the balloon situated above this patch, according to illustrative embodiments.

FIG. 32 expands on the design introduced in FIG. 31, presenting an implementation where the torn or otherwise damaged cuff 3204 is strategically positioned within the void created by the patch 204, and the balloon 208 situated above this patch layer. This configuration thus sandwiches the torn cuff 3208 between two collagen-rich layers-one below and one above 3212. Such an arrangement is specifically engineered to enhance the healing process by ensuring that the damaged cuff 3208 is enveloped in a collagen-dense environment. This embodiment not only promotes effective tissue regeneration by providing essential support to the injured area, but also improves the conditions for a faster and more robust healing process. The design underscores a thoughtful approach to post-surgical recovery, aiming to maximize the therapeutic benefits and improve patient outcomes by leveraging the natural healing properties of collagen in a structured and targeted manner.

While the primary focus above has been on rotator cuff repair, the underlying principles and benefits of the described systems and methods have broader implications for orthopedic surgery. Specifically, similar challenges and requirements exist in the repair of other critical anatomical structures, such as the anterior cruciate ligament (ACL) in the knee, the Achilles tendon at the back of the ankle, and the flexor tendons in the hand, which are essential for a wide range of motions and activities. The adaptability of the techniques to these areas suggests a versatile and transformative potential across various tendon repair procedures. In fact, many long tendons in the body such as these may benefit from a balloon-patch combination implant, where the balloons 208 can provide a malleable tubular structure, wrapped in patch material 204 to encourage tendon regrowth.

Accordingly, various embodiments can be customized to support and enhance the natural process of various tendon regeneration types. The implant leverages a malleable tubular structure provided by the balloon 208, which can be precisely positioned and adjusted to conform to the unique contours and requirements of the repair site. This balloon 208 is then coupled to the specially designed patch material 204, which acts to encourage and facilitate the growth of new tendon tissue. The combination of these two components creates an environment conducive to healing, offering both structural support and biological stimulation to the damaged tendon.

Potential applications of this balloon-patch combination implant extend even further. Long tendons throughout the body, characterized by their critical load-bearing functions and susceptibility to injury, may benefit from this approach. The design considerations of the balloon and patch materials can be tailored to the specific mechanical and biological needs of each repair scenario, offering a customizable and versatile tool in the surgeon's arsenal. This adaptability, coupled with the potential for enhanced healing and recovery, positions the balloon-patch combination implant as a useful advancement in the field of orthopedic surgery, which may provide improved outcomes for patients suffering from a wide range of tendon injuries.

Yet other embodiments, beyond the balloon-patch combination implant in tendon repair, may involve procedures involving the removal of cysts or tumors beneath superficial skin layers, such as on the face, where this implant could significantly enhance the healing process. For example, after the surgical excision of pathological tissue, the void left behind often poses a challenge for effective and aesthetically pleasing tissue regeneration. The balloon 208 component of the implant offers a solution by filling the space previously occupied by the tumor or cyst, thereby maintaining the natural contour of the area and preventing tissue collapse or indentation that often occurs post-surgery.

Furthermore, the integration of a patch 204 on the subdermal side of the balloon 208 adds another layer of support for tissue reconstruction at the surgical site. This patch material 204, designed to encourage tissue ingrowth, can facilitate the regrowth of healthy skin and subcutaneous tissues, potentially improving the cosmetic and functional outcomes of such surgeries. The application of the balloon-patch combination in this context not only aids in maintaining the structural integrity of the surgical area but also promotes a more natural healing process. This approach could become important for post-surgical recovery, especially in sensitive areas where the appearance and preservation of normal anatomy are paramount, offering patients a more effective post-surgical healing process.

Illustrative embodiments therefore relate to a combination implant constructed of both a patch 204 and a balloon 208, using the features of each and realizing some new benefits as well. As suggested above, this combination in various embodiments may be considered to form the repair matrix 120.

The patch 204 component (i.e., scaffold) of the implant provides the mechanical and biological functionality as described above. By incorporating a balloon 208 component attached (superior) to the patch 204, the resulting combination offers additional protection to the (augmented) soft tissue repair. The balloon 208 component, rather than existing in the subacromial space, may be intimate with the repair site, preferably moving with it through range of motion. This produces a protective environment for the repair, with improved clinical results in many instances to a patch implant alone.

In addition to offering additional protection, the balloon 208 also helps to keep the patch 204 and tendon tissue compressed (often somewhat evenly) across the area of the repair. Without various embodiments, surgeons typically spend significant time arranging the sutures and anchors to spread out the compressive load across the repair site. The supplemental compression generated by the presence of the balloon 208 can be seen as beneficial for the success of the repair.

Also as noted, the balloon 208 also can function in the delivery of the implant 100 to the repair site. The balloon-patch combination implant (i.e., the repair matrix 120) enables a patch 204 unfurling technique: using balloon 208 inflation. This combination device preferably simplifies the procedure (in device complexity and/or surgeon requirements) by utilizing the already necessary inflation step to prepare the implant 100 for positioning over the repair site.

Those skilled in the art may use different fluids, components, biphasic material, etc. within the expandable interior of the balloon 208. For example, use of air as a filling material/fluid for the balloon 208, as opposed to saline, presents a viable alternative with potential advantages in the context of medical implants. Theoretically, air can offer the same mechanical support and stabilization benefits as saline while facilitating a more streamlined preparation and delivery process for the implant. This simplification could result in shorter surgical times and possibly reduce the risk of complications associated with the implantation procedure. Moreover, using air might also decrease the overall weight of the installed implant 120, which could enhance patient comfort and recovery outcomes.

The balloon 208 can be used as a drug eluting device in some embodiments. For example, the balloon 208 may be filled with a saline solution containing a variety of therapeutic agents. These agents can include anti-inflammatory medications, antibiotics, cortisone, and other drugs tailored to the patient's specific post-operative needs. The integration of these drugs into the saline volume of the balloon 208 allows for a unique method of drug delivery directly to the site of surgery, such as the shoulder, where targeted treatment can be most beneficial.

Over time, as the material of the balloon 208 begins to degrade, a controlled release of the contained drugs into the surrounding tissue is triggered. The balloon 208 is configured so that the degradation process occurs at a rate that supports optimal healing, preferably ensuring that the release of medication aligns with the critical phases of the patient's recovery. The slow and steady leakage of the drugs from the balloon 208 creates a time-released delivery system that can significantly enhance post-operative recovery by continuously providing therapeutic benefits directly at the site of need.

This method of localized, time-released drug delivery presents several benefits over traditional systemic drug administration. By concentrating the medication directly where it is most needed, lower overall doses may be required, potentially reducing the risk of systemic side effects, and improving patient outcomes. Furthermore, this approach can simplify post-operative care routines, reducing the need for oral or intravenous medication, enhancing patient compliance.

Rather than use saline for inflation, some embodiments fill the balloon 208 with a liquid or slurry-like collagen as the filling material to enhance post-operative recovery. As the balloon 208 wall undergoes degradation over time, the collagen gradually seeps out into the adjacent shoulder tissue. This process preferably is designed to coincide with critical healing phases, where the supplemental collagen can significantly bolster tissue regeneration and repair. The introduction of collagen directly to the injury site serves not only to promote faster healing but also to potentially improve the overall strength and functionality of the healed tissue, offering a promising strategy for improved patient outcomes in shoulder surgeries.

Some embodiments configure the balloon 208 with a specific design variation featuring a dual-thickness balloon wall: a thinner material on the bottom face and a thicker material on the top. This design ensures that the degradation of the balloon 208 wall commences from the bottom, facilitating an earlier release of collagen directly onto the healing rotator cuff tendon. Such targeted delivery may aim to concentrate the therapeutic benefits of collagen precisely where it is most needed, potentially accelerating the repair process and enhancing the quality of tendon recovery. This embodiment underscores a careful consideration of material properties and anatomical needs, optimizing the healing environment for the rotator cuff post-surgery.

Expanding on the concept of targeted therapeutic delivery, another embodiment may incorporate "pores" on the bottom surface of the balloon 208. Initially sealed at the time of implantation, these pores may be configured to dissolve at a faster rate than the surrounding balloon 208 material. This ensures that the collagen is released in a focused manner to the area of healing tissue below, after the pores open. Such a method further refines the precision of collagen delivery, ensuring that the regenerative benefits are concentrated directly on the damaged tissue. This embodiment exemplifies the potential for advanced material engineering to enhance post-operative healing by ensuring that critical support is provided where and when it is needed.

In another embodiment, the system may utilize at least a partially hydrogel filled balloon 208. When saturated with fluid (e.g., saline), the hydrogel should help to maintain some structural integrity of the balloon volume and its ability to maintain its function through the healing period. This could be coupled with a plurality of micropores in at least a portion of the balloon membrane to encourage fluid inflow to the hydrogel within the balloon 208.

Whether containing hydrogel or not, the interior of the balloon 208 may be super-salinated when left in position at the repair site. A higher concentration of salt within the volume of the balloon 208 should encourage osmotic movement of fluid from the surrounding tissue envelope to the interior of the balloon 208. This is facilitated by the noted plurality of micropores in the membrane of the balloon 208, and/or by having a water-permeable balloon membrane. By establishing an osmotic gradient as described, the volume of the balloon 208 is expected to be maintained for a longer period of time.

In fact, these or other embodiments of the balloon interior may be configured with one or more internal chambers. Those chambers may be fluidly isolated, or, in some embodiments, fluidly connected. One of these chambers would be dedicated to containing saline, leveraging its mechanical benefits to support the structural integrity of the balloon 208 and the surrounding tissue. The other chamber(s) may be specifically designed to hold the therapeutic agents, such as drugs or collagen. These therapeutic chambers could be constructed to degrade at a more accelerated pace compared to the saline-containing chamber. This design allows for a sequential release strategy, where the mechanical support from the saline is maintained while the therapeutic substances are precisely delivered to the healing tissues at an optimized time. This technique not only improves the therapeutic efficacy of the balloon implant but also ensures a sustained support structure throughout the healing process.

In some embodiments, one or more sensors may be associated with one or both the balloon 208/expandable member and/or the patch 204 and configured to collect data, such as patient data, procedure data, or data relating to the implant. One or more of these sensors may be additively printed into or onto the balloon material, and/or laminated onto the film on a balloon 208. Some embodiments integrate pressure sensors within the balloon's structure to monitor its internal pressure in real-time, offering valuable insights into the behavior of the implant post-surgery. A strain gauge, for example, may contain typical strain gauge materials. This data can inform both the patient and surgeon about the load the implant is experiencing and facilitate long-term monitoring of its condition. Such information can help assess the success of the surgical intervention and ensure the implant's functionality aligns with the healing process.

Similarly, strain sensors can be strategically placed either at the base of the patch 204, in direct contact with the healing tissue, or within the implant itself 100, such as in the space between the balloon 208 and the patch 204. These sensors are designed to gather detailed information about the mechanical behavior of the repair site and the tendon's recovery progress. By monitoring how the repaired tendon regains its normal function, these sensors provide feedback on the effectiveness of the treatment and the patient's rehabilitation process, enabling more personalized and informed post-operative care.

In one embodiment, sensors may be associated with a power source and a wireless transmitter or transceiver. The sensors may be configured to transmit data continuously, at regular intervals, or at specific time(s) of the day. This data therefore can relate to device and/or patient data (or other type of data). In one embodiment, sensors may be 3D printed into the balloon 208, the patch 204, or an integrated balloon and patch.

In one embodiment, the implant 100 or installed implant 120 may include a processing device, memory, an optical or radio frequency (RF) receiver or transmitter (or transceiver), and a power source. The processing device may execute one or more stored programs in the memory and/or download stored programs through the receiver. In one embodiment, the processing device may receive commands to provide data, obtain the data from the one or more sensors, and transmit the data to another processor. The other processor may be either within the same patient as the implant or elsewhere. For example, the processor may receive a request to provide pressure data on volume areas 224. The balloon 208 may include several independently inflatable chambers or include one or more small balloons 4604 as shown in FIG. 46. Each chamber or small balloon 4604 may have an associated pressure sensor configured to transmit a current pressure value to the processor, when requested. The processor may receive the pressure sensor value(s) and transmit the pressure value(s) in response to the request. In this way, a physician may observe proper healing progress of the installed implant 120 and receive an indication the balloon 208 and/or patch 204 is being dissolved properly.

In another embodiment, the installed implant 120 may have one or more temperature sensors and provide current temperature readings for specific repair locations of the installed implant 120. For example, high temperature readings above a known threshold may inform a physician of an infection or developing infection in the repair area that needs to be treated.

Similar embodiments may implement some sensors as bioresorbable sensors (e.g., temperature sensors). Many other types and combinations of sensors (e.g., oxygen sensors, PH sensors, motion sensors) and data associated with the implant 100 or installed implant 120 and not specifically disclosed herein are contemplated by the present application.

Rather than using conventional sutures, some embodiments may use barbed sutures (see FIG. 23) to secure the system to the anatomy. These sutures, which are readily available on the market or can be custom-designed, feature barbs that effectively prevent migration, ensuring the implant and the tissue it is attached to remain in place. This capability to restrict movement in one or multiple directions enhances the stability of the installed implant 120, facilitating optimal healing and integration with the underlying tissue.

Figure 33:
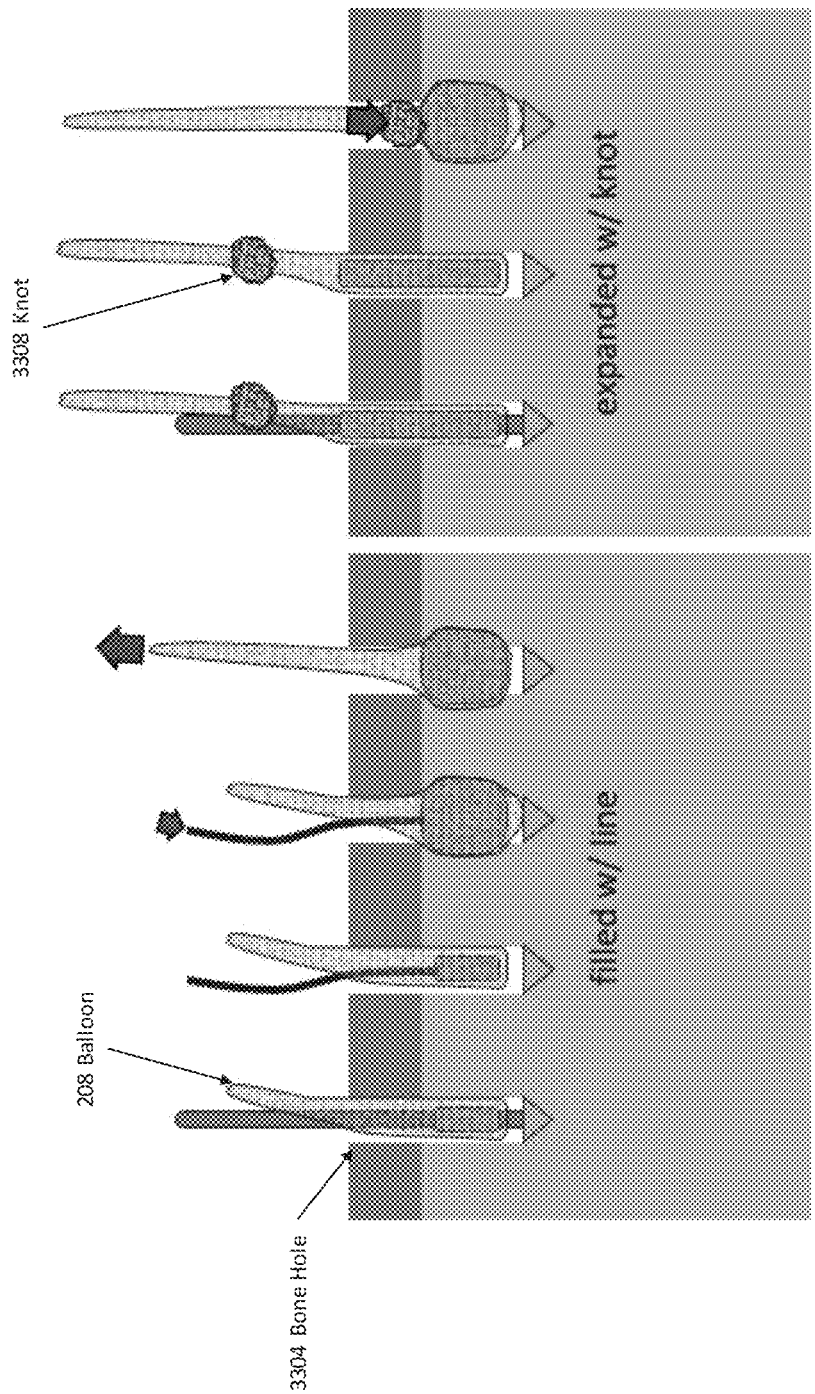
FIG. 33 schematically shows a balloon within a bone hole that cannot come back out of the hole into which it was inserted, according to illustrative embodiments.

Suture anchors (such as for labral and rotator cuff repair) are generally preferred to be smaller in diameter and with less disruption to bone (e.g., also requiring a shallower bone hole). Illustrative embodiments insert and inflate a balloon 208 within a bone hole 3304 so that it cannot come back out of the hole into which it was inserted. This represents the basis for another anchor construct. FIG. 33 schematically shows several examples of this embodiment.

The balloon 208 can be surrounded by a textile layer, such as the terminal end of a suture that extends from the bone hole 3304 and is available for incorporation into a soft tissue repair. The textile may also act as a protective layer, insulating the balloon membrane from the surrounding subcortical bone.

The balloon 208 could be inserted to the bone hole 3304 in a deflated state, followed by an inflation step using a filling system such as a catheter or tube-like structure.

Alternatively, the balloon 208 could arrive at the bone hole 3304 already filled but in a narrow but elongated configuration to enable insertion into the depth of the bone hole 3304. This elongated balloon 208 could be surrounded by a textile which is expanded within the bone hole 3304, preventing pullout of the construct. This expansion could be enabled by advancing a knot 3308 (or other constricting feature) down into the bone hole 3304 along the textile length, forcing the balloon 208 to change from a narrow-elongated shape to a wider and shorter shape. Being a compliant and deformable construct, the balloon 208 with textile would expand into the bone hole 3304, occupying all available voids to maximize the anchor fixation.

Similarly, the knot 3308 (or other constricting feature) could be located distal to the elongated balloon 208, and when pulled, would reshape the balloon 208 into a wider and shorter shape, achieving said fixation.

There could be one or multiple balloons 208 in this concept, possibly in-line. There could be a toroidal or cylindrical shape to one or more of the balloons 208. For the embodiments with an aperture within the body of the balloon 208, the textile, in addition to encapsulating the balloon 208, could also pass through the aperture (or apertures) to further control the balloon's expansion and associated fixation. Moreover, rather than being an inflatable balloon 208, some embodiments may have an expanding material that expands when within the bone hole 3304 (e.g., a time inflation based on material choice, temperature, moisture exposure, etc.).

Figure 34:
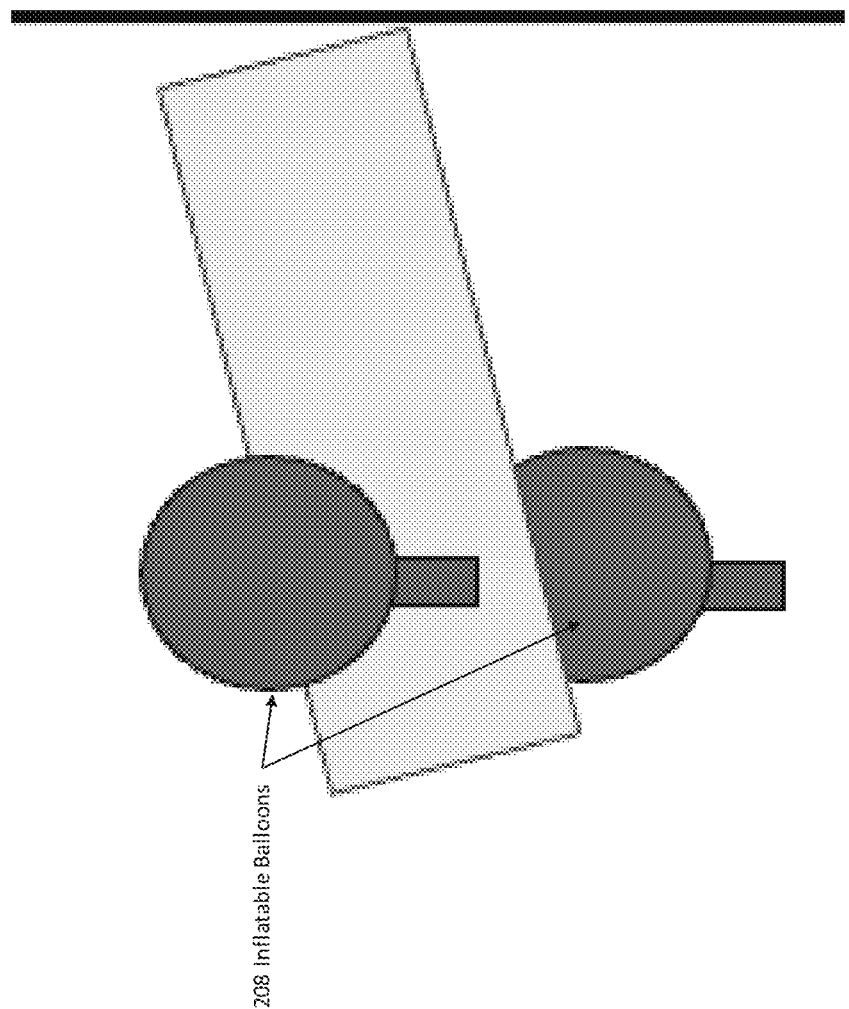
FIG. 34 schematically shows a include a plurality of inflatable balloons configured to expand above and below a target tissue or patch augment, according to illustrative embodiments.

Another embodiment, shown in FIG. 34, may include a plurality of inflatable balloons 208 configured to expand above and below a target tissue or patch augment, in order to control its position within a repair.

Figure 35:
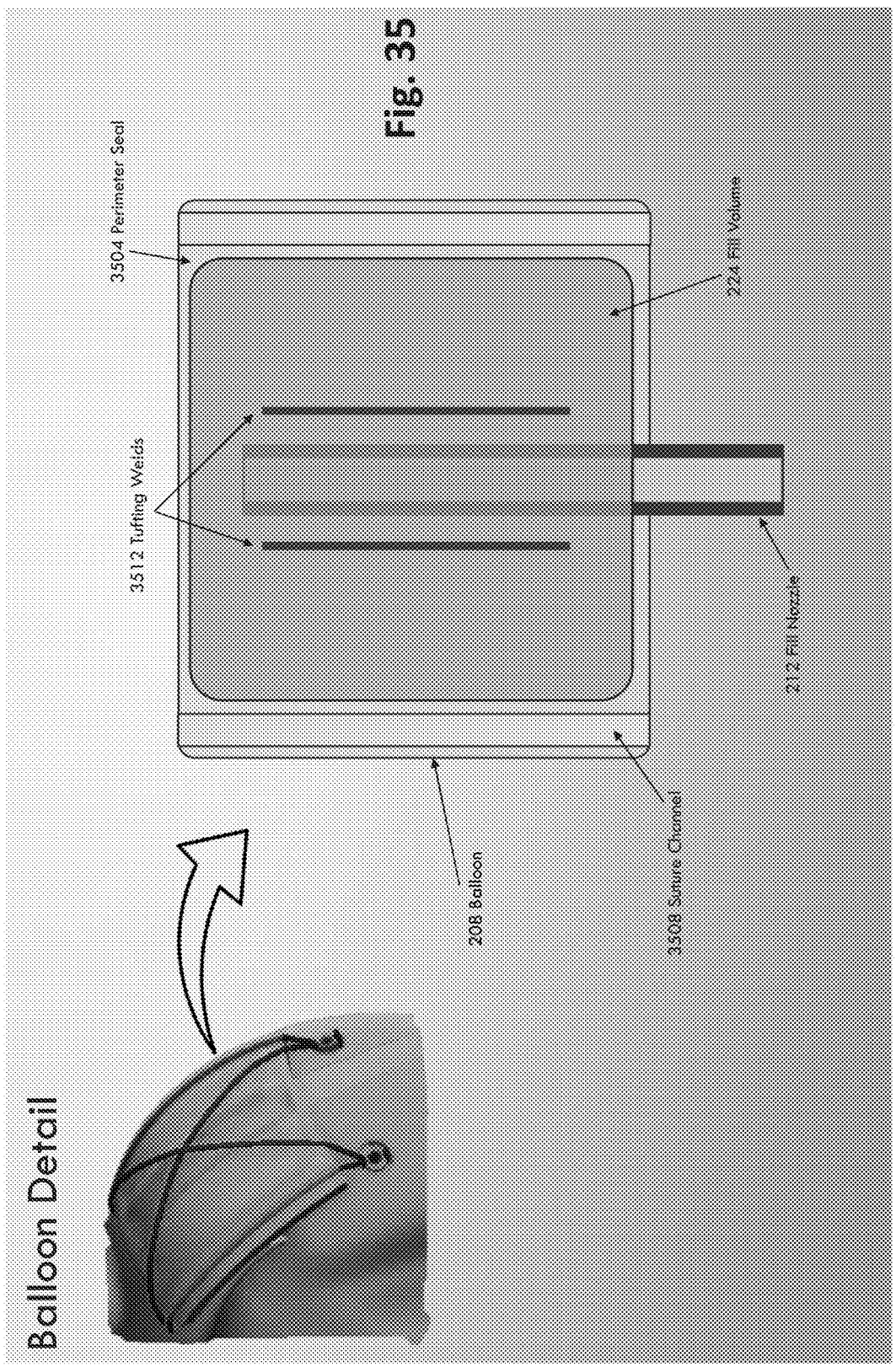
FIG. 35 schematically shows details of a balloon, according to illustrative embodiments.

FIG. 35 schematically shows details of a balloon 208 of a preferred embodiment. In the illustrated embodiment, outer edges of the balloon form a perimeter seal 3504. The perimeter seal 3504 areas do not inflate and are always in a flat state. The fill volume 224 is filled with saline, air, etc. as previously described. Preferably, the balloon 208 is of a square or rectangular shape and the installed implant 120 is less than 10 mm thick when fully inflated.

Illustrative embodiments use tufting techniques to maintain a desired uniformity in the expandable member thickness. Specifically, in this context, tufting often refers to the technique where specific points on the balloon are connected or tethered to maintain a consistent structure when the balloon is inflated or deflated. Similar to tufting in pillows or mattresses, where certain areas are secured to maintain an even surface, tufting in a balloon ensures that the thickness of the balloon material remains generally uniform during expansion and contraction. This uniformity helps achieve more predictable and reliable performance in medical procedures, such as dilating vessels or deploying stents, where consistent pressure distribution is essential.

By controlling the shape and thickness of the balloon, tufting helps prevent irregular bulging or uneven expansion, which can lead to unwanted stress on tissues or cause procedural complications. This design feature allows the balloon to expand in a more controlled manner, ensuring that it conforms to the anatomy and provides a more effective, safe, and precise intervention during surgeries or therapeutic applications.

The embodiment shown in FIG. 35 has tufting welds 3512 directly and permanently connect the top side of the balloon 208, and to the bottom side of the balloon 208. This effectively divides up the fill volume 224 into multiple sections and limits a maximum filled thickness of the balloon 208 to achieve a lower profile for the installed implant 120. A given balloon 208 may include any number or length of tufting welds 3512 and tufting welds 3512 may be linear as shown or non-linear or identical or different. The balloon 208 is filled through a fill nozzle 212 coupled to a valve within the fill volume 224. The valve allows fill material to enter the fill volume 224 while preventing backflow through the fill nozzle 212 out of the balloon 208. Other embodiments may use other types of valves, such as a stopper, flapper valve, plunger valve, or an elastomeric gasket with an openable aperture that is normally closed.

The balloon 208 may have one or more integral suture channels 3508 with opposed open ends configured to pass or contain a suture. Suture channels 3508 are tunnels formed through the thickness of a member, such as the balloon 208, which, as noted, allows sutures to pass therethrough. Specifically, the component (e.g., the balloon 208 or the entire repair matrix) forming at least one of the suture channels 3508 is considered to have top and bottom surfaces/faces (typically generally flat/planar, particularly when deflated) that each have a relatively large area, and a thickness/width with a length that is much smaller than the length or width of either of the top or bottom faces. As shown in the figures, the majority of the length of the suture channels 3508 extend generally parallel with, or in a direction along, the top and bottom faces of the component. The majority of the length does not extend normal to these faces. This is considered to mean that the suture channels 3508 extend along the "thickness" of the component to at least one edge of the component. However, one or both ends of the suture channel 3508 can terminate at one of the noted faces despite the fact that the majority extends through the thickness in the manner shown. Moreover, in preferred embodiments, the suture channels 3508 are generally straight, although they can have some contour.

In the preferred embodiment, there may be two suture channels oriented on the anterior and posterior sides of the balloon 208 that connect through the balloon 208 from the medial side/edge through the lateral side/edge, as shown in FIG. 35. In one embodiment, the suture channels 3508 may provide partial or complete tunnels through the entire length of the balloon. In one embodiment, a suture channel 3508 may extend at least halfway across the longest dimension of the balloon 208. In that case, the suture channel 3508 may have a first end at one edge of the balloon (e.g., the lateral or medial edge) and another end through one surface of the balloon 208. For those that extend the entire length, the suture channels 3508 may have one end at the medial edge of the balloon 208 and another end at the lateral edge of the balloon 208.

The balloon 208 may include any number of suture channels 3508, and suture channels 3508 may extend fully or partially across the balloon 208 in any direction or combination of directions (e.g., with respect to the balloon 208 illustration of FIG. 35, horizontally, vertically, diagonally, in a zig-zag pattern, in a curved pattern, or in any other shape or combination of shapes). Preferably, the suture channels 3508 are generally parallel with the longitudinal axis formed by the balloon and/or the overall repair matrix 120. This longitudinal axis may be defined by the long dimension of the balloon 208, and/or extend between the medial and lateral ends/edges of the balloon 208. Alternatively, they may be generally perpendicular.

Some embodiments may form one or more of the suture channels 3508 in a location other than completely in the balloon 208. For example, the repair matrix 120 may have a suture channel 3508 in the space between the balloon 208 and the patch 204, or through the patch 204. Some embodiments may have one suture channel 3508 through the balloon 208 and another through other parts of the repair matrix 120.

In one embodiment, at least one suture channel 3508 is configured to completely encapsulate a suture across the repair matrix 120. Therefore, in this embodiment there would be no openings in the suture channel 3508 along the length of the repair matrix 120. Instead, the suture channel may extend between and terminate at the lateral and medial edges of the balloon 208.

Advantageously, the balloon 208 including tufting welds 3512 and multiple fill volume 224 areas makes use of dynamic compression. This allows the filling solution material to travel to where it needs to through all ranges of motion throughout the healing process, which ensures more consistent downward force contact between the integrated biologic layer (patch 204) and the underlying tissue to be healed.

Figure 36:
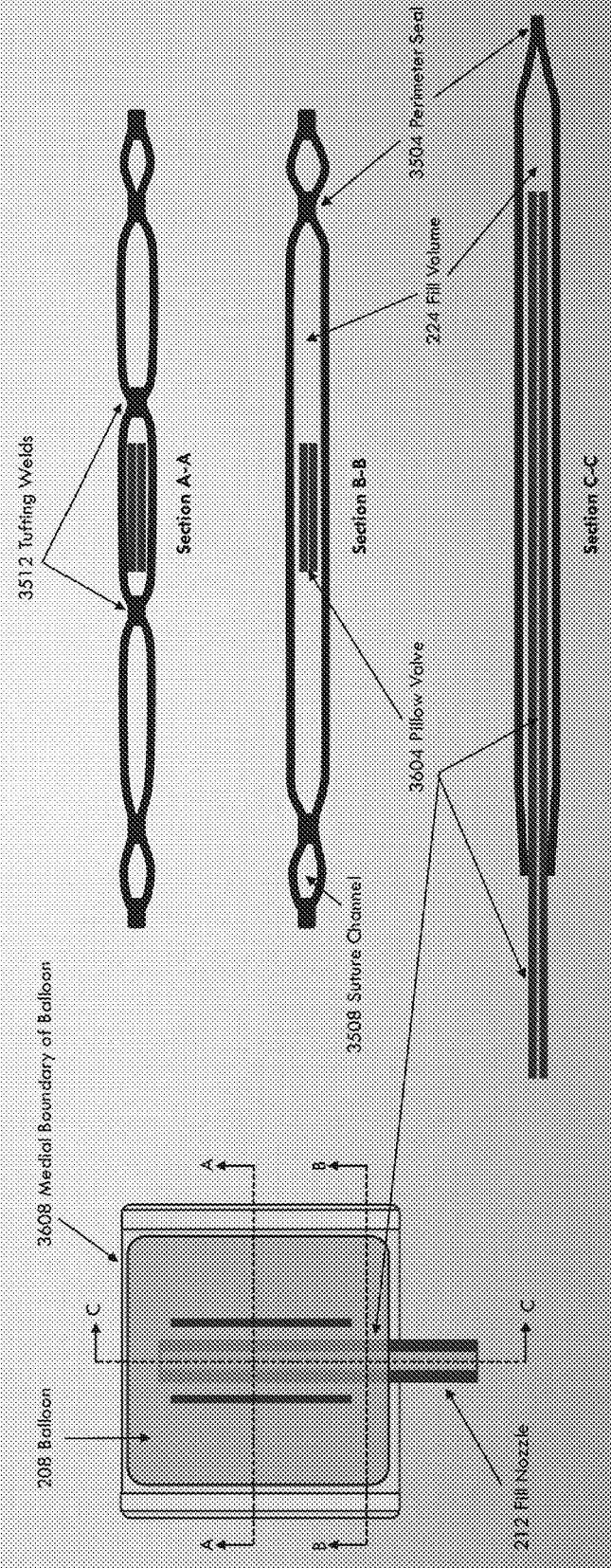
FIG. 36 schematically shows a pillow valve configuration for the balloon, according to illustrative embodiments.

FIG. 36 schematically shows a valve configuration for the balloon 208. Section A-A shows two tufting welds 3512 dividing the balloon 208 into three approximately equal-width sections for most of a length of the balloon 208. Section B-B shows no tufting welds 3512 at that point in the balloon 208, resulting in one fill volume 224 area. Section C-C shows a lengthwise profile through a center of a pillow valve 3604.

Specifically, as known by those in the art, a pillow valve inside illustrative embodiments of the balloon 208 functions a specialized one-way valve system designed to control the flow of fluid-such as air or liquid-into and out of the balloon. It may have a soft, flexible structure that conforms to the interior shape of the balloon when not in use, resembling a "pillow" that minimizes obstruction and provides a uniform surface when the balloon is deflated.

Typically made from biocompatible materials like silicone, polyurethane, and/or the material of the balloon 208, the pillow valve relies on a pressure differential mechanism: it opens under external pressure, allowing inflating fluid to enter the balloon, and then seals tightly (as a result of internal balloon pressure) to prevent backflow when the external pressure is removed. The valve is securely integral or bonded to the interior surface of the balloon, ensuring a reliable seal and maintaining proper function throughout multiple inflation and deflation cycles. This design is particularly advantageous in illustrative embodiments where precise control over balloon inflation and deflation is critical for patient safety and procedural efficacy.

Some embodiments may have an unbiased, floppy pillow valve when not in use. Other embodiments may bias the pillow valve closed before inflation, but openable when subjected to a certain amount of external pressure.

Unlike a traditional one-dimensional (1D) seal, such as those found in flapper valves or check valves, where a valve member presses against a discrete valve seat to create a point or line seal, a pillow valve creates a more robust two-dimensional (2D) seal. Such a 2D seal can be flat, undulating/wavy, etc. This involves an area-against-area contact (i.e., a sealing area or region), where the soft, conformable surface of the valve covers a larger area of the balloon's inner surface to form a seal. The 2D seal of the pillow valve should provide good sealing capabilities. In addition, the pillow valve's 2D sealing mechanism distributes the sealing pressure over a broader area, enhancing leak prevention and overall durability in dynamic and high-pressure environments typical of medical procedures.

The fluid fill path, which permits fluid to enter and exit the balloon interior, is generally orthogonal to the direction of movement of the sealing area of the pillow valve. For example, fluid may enter the balloon in a generally linear manner along what may be considered a temporary fluid conduit. This fluid conduit collapses when the pressure in the balloon interior exceeds that of the exterior of the balloon 208. Fluid pressure through this temporary conduit also may, in some embodiments, open the valve. Either way, this collapsing may be in a direction that is generally orthogonal to the direction of the fill fluid through this temporary conduit.

In one embodiment, the balloon 208 may include an integral pillow valve 3604. The pillow valve 3604 extends from the fill nozzle 212 most of the toward the medial boundary of the balloon 3608. Also shown in FIG. 36 are two suture channels 3508, disposed on the left and right sides of the balloon 208.

Figure 37:
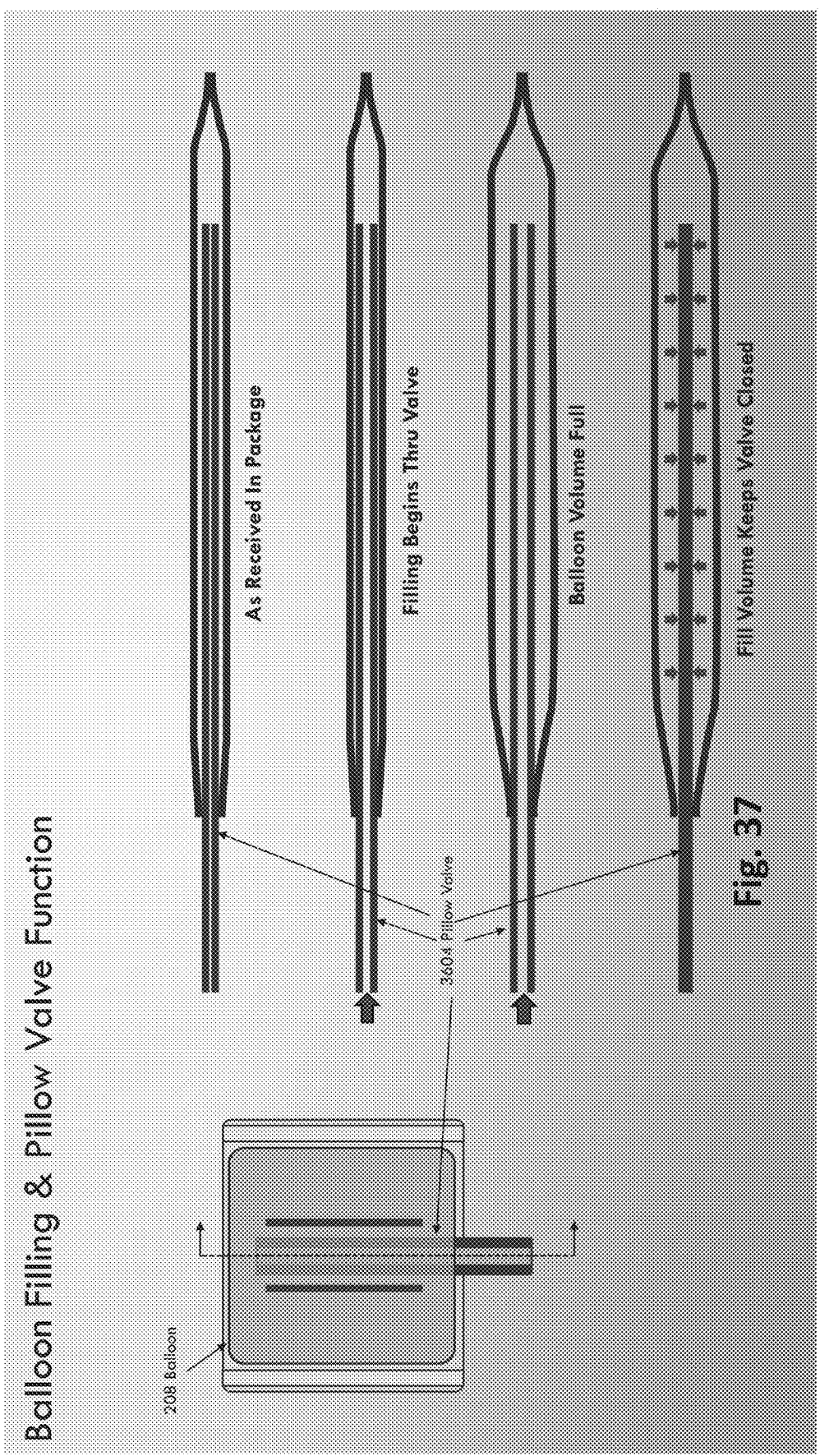
FIG. 37 schematically shows balloon filling and pillow valve function, according to illustrative embodiments.

FIG. 37 schematically shows balloon filling and pillow valve function. FIG. 37 illustrates the pillow valve 3604 operation and various states of filling. The pillow valve 3604 behaves similar to the behavior of a valve for a mylar party balloon, able to receive a fill material (e.g., saline, air, etc.) when received in a package. The pillow valve 3604 slightly expands as filling begins until the balloon 208 volume is full (i.e., fully inflated). In the fully inflated configuration, pressure from the outside surfaces of the balloon 208 exerted on the fill material cause the pillow valve 3604 to shut and remain closed. This serves a backfill prevention function while keeping the balloon 208 fully inflated. As such, the valve is free of a valve member, diaphragm, or similar parts.

Figure 38:
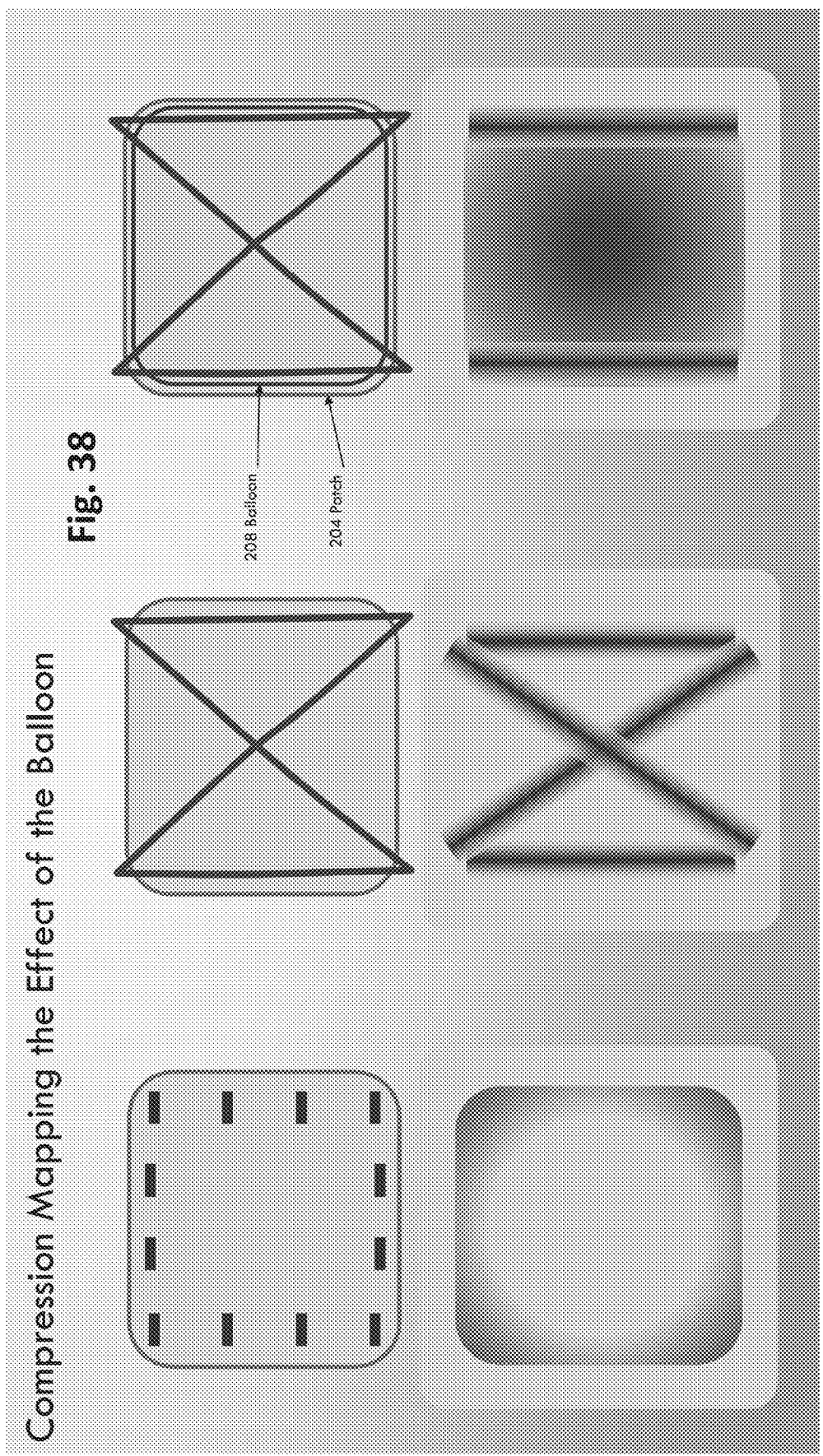
FIG. 38 schematically shows compression mapping the effect of a balloon, according to illustrative embodiments.

FIG. 38 schematically shows compression mapping the effect of a balloon 208 with various suture and balloon 208 configurations. The upper three images illustrate the method of suture attachment while the bottom three images illustrate a pressure map corresponding to the attachment means directly above. In the left set of images sutures are only applied around the periphery (no balloon 208). This results in a pressure map where the greatest pressure is around the boundary and decreases toward the center. In the center set of images, an "X" suture pattern is applied, along with left and right side suturing (no balloon 208). In this case, the areas of high pressure correspond directly to the sutures, with pressure voids between the sutures. In the right set of images, however, the same suture pattern is used as with the center set of images, but the balloon 208 is installed below the sutures. The corresponding pressure map shows strong but more diffused vertical pressure lines that correspond to the left and right side sutures, and a more uniform central rectangular pressure map that corresponds to the "X" pattern. This beneficially distributes compression more evenly over the area of the installed implant 120. Stated another way, this figure shows the beneficial pressure applied by the balloon 208 as it urges the patch 204 toward the tissue being repaired. The balloon 208 preferably is configured to provide a clinically sufficient pressure when inflated (i.e., neither too high nor too low), although the physician's skill also should be taken into account when making that pressure.

Figure 39:
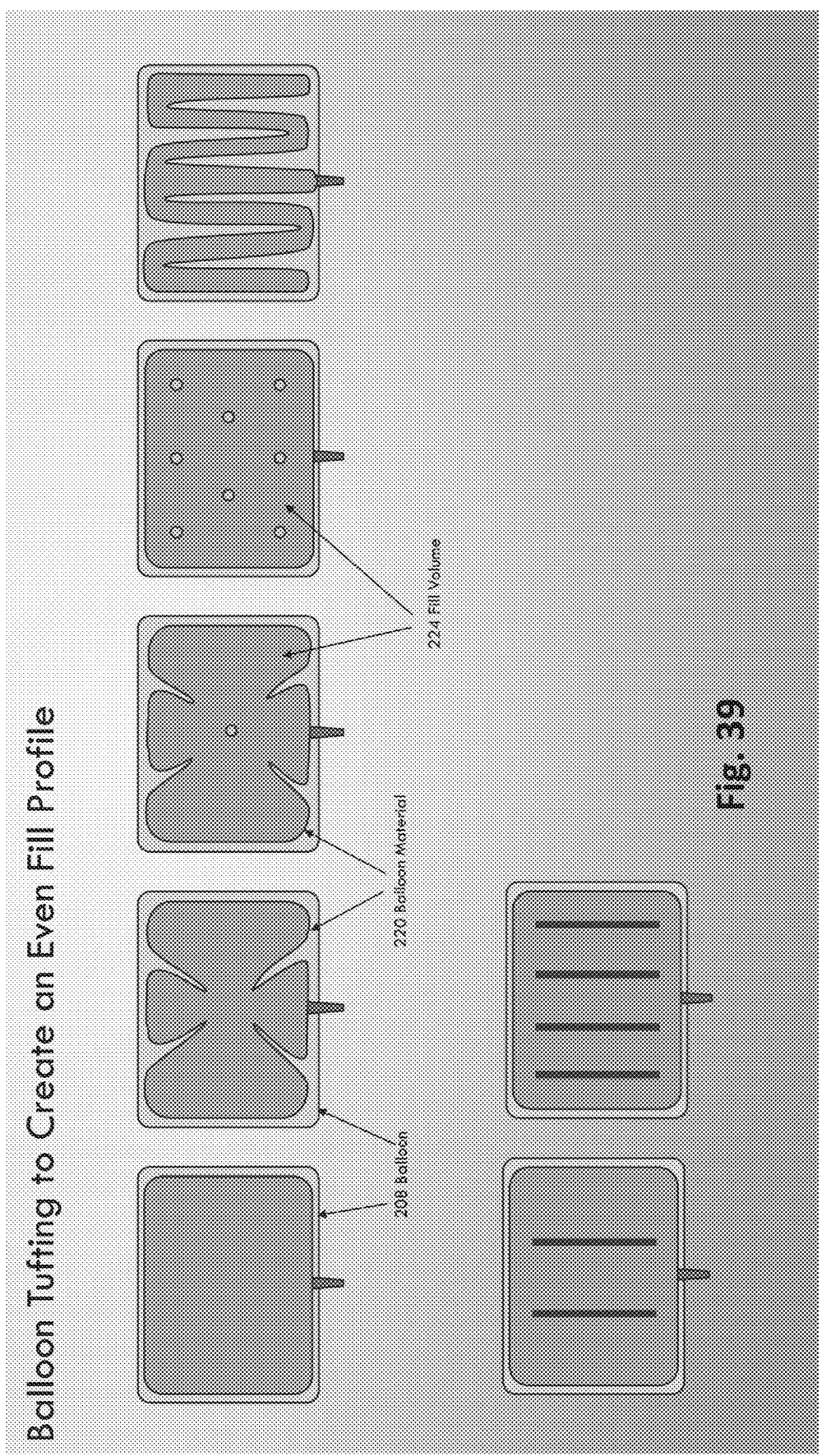
FIG. 39 schematically shows balloon tufting to create an even fill profile, according to illustrative embodiments.

FIG. 39 schematically shows balloon tufting examples to create a more even or distributed fill profile. "Tufting" is where the top and bottom layers of the balloon 208 are connected by spot welds, lines, or any shapes to prevent the fill volume 224 from becoming spherical. This technique is used in inflatable air mattresses and upholstery. Tufting beneficially contributes to a lower profile for the installed implant 120 by "pulling in" the upper surface of the balloon material 220. For example, the fourth embodiment from the top left (8 "point tufts") would have a lower profile than the untufted embodiment at the top left because there is nothing to restrain the center height of the untufted balloon 208.

Figure 40:
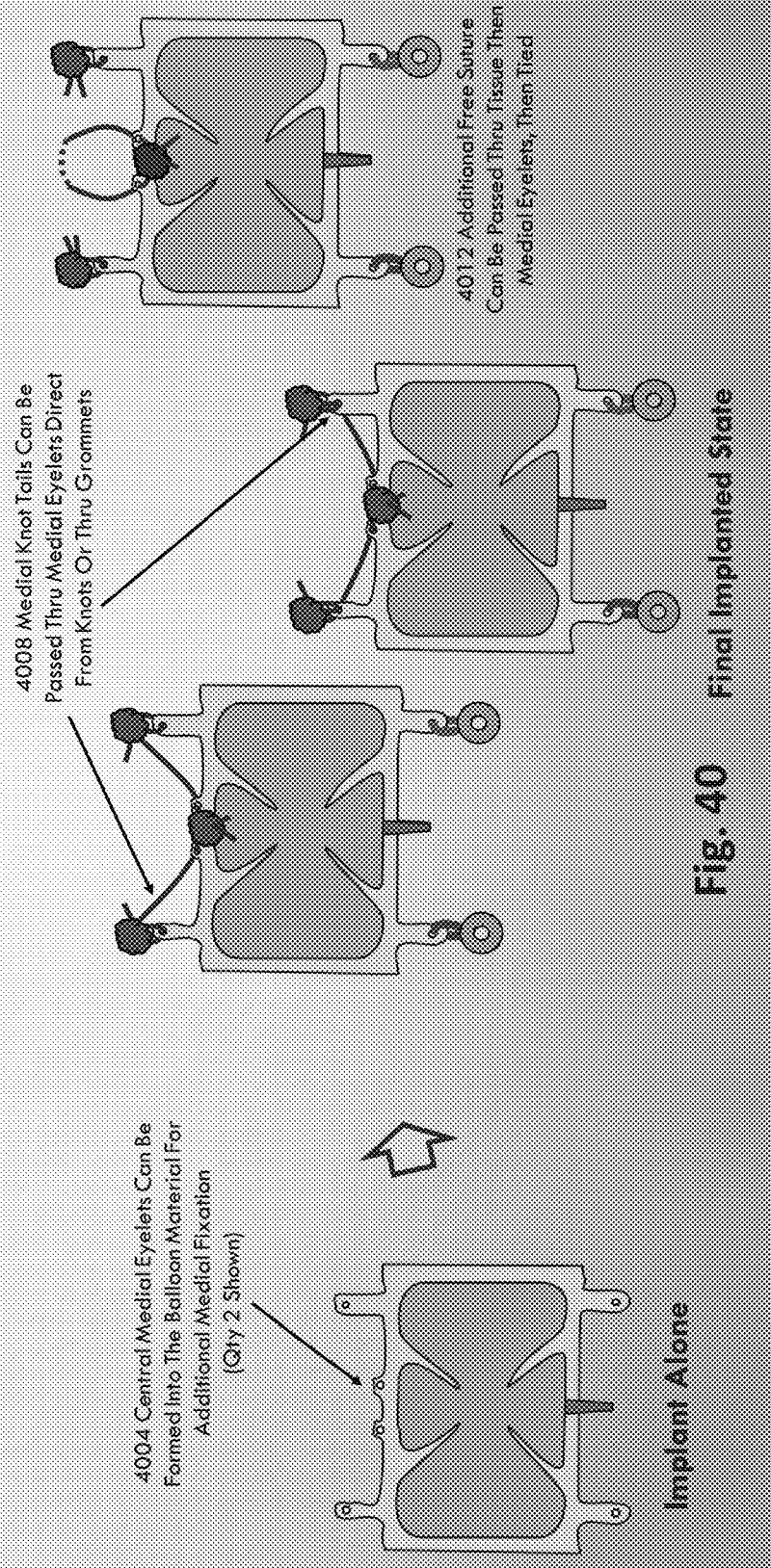
FIG. 40 schematically shows an original grommet balloon with no patch and optional medial eyelets, according to illustrative embodiments.

FIG. 40 schematically shows an exemplary balloon that may be ready to receive a patch; in other words, this balloon has no patch 204 yet and thus, is not a complete repair matrix 120. As such, this embodiment has a receiving area/region on its side that will face the tissue under repair when implanted. This receiving area couples/interfaces with the patch 204 when the patch 204 is added.

This example also may have optional medial eyelets 4004 on the medial edge of the balloon 208 for additional security. The medial edge is where the implant will see the greatest loading after implantation (in shear, from the underside of the Acromion). The additional eyelets (2 shown, but could be 1, 2, 3, or more) accept sutures, which are tied to the tendon below. Shown at right are three possible suture configurations for utilization of the additional medial eyelets. At 4008, the medial knot tails can be passed through the medial eyelets directly from knots or through grommets. At 4012, additional free suture can be passed through tissue, then medial eyelets, then tied.

The patch 204 is not shown in the FIG. 40-44 embodiments, but in some embodiments may be present. This is meant to imply that the balloon 208 alone may be viable as an installed implant 120 and/or ready to receive and secure (in some embodiments) the patch 204. Among other ways, the patch 204 may be secured to the balloon in any of the above-described techniques, which include bonding, mechanical fastening, interlocking, or encapsulation. Some embodiments of the repair matrix 120, however, may simply have the balloon 208 abutting the patch 204 but not attached. Those skilled in the art, caregivers, or others may select the preferred relationship between the two components 204 and 208.

The patch 204 may add additional thickness or bulk that may be undesirable, and/or the balloon 208 may act as a drug eluting device by including one or more volume areas 224 that contain drugs to facilitate healing and repair.

Figure 41:
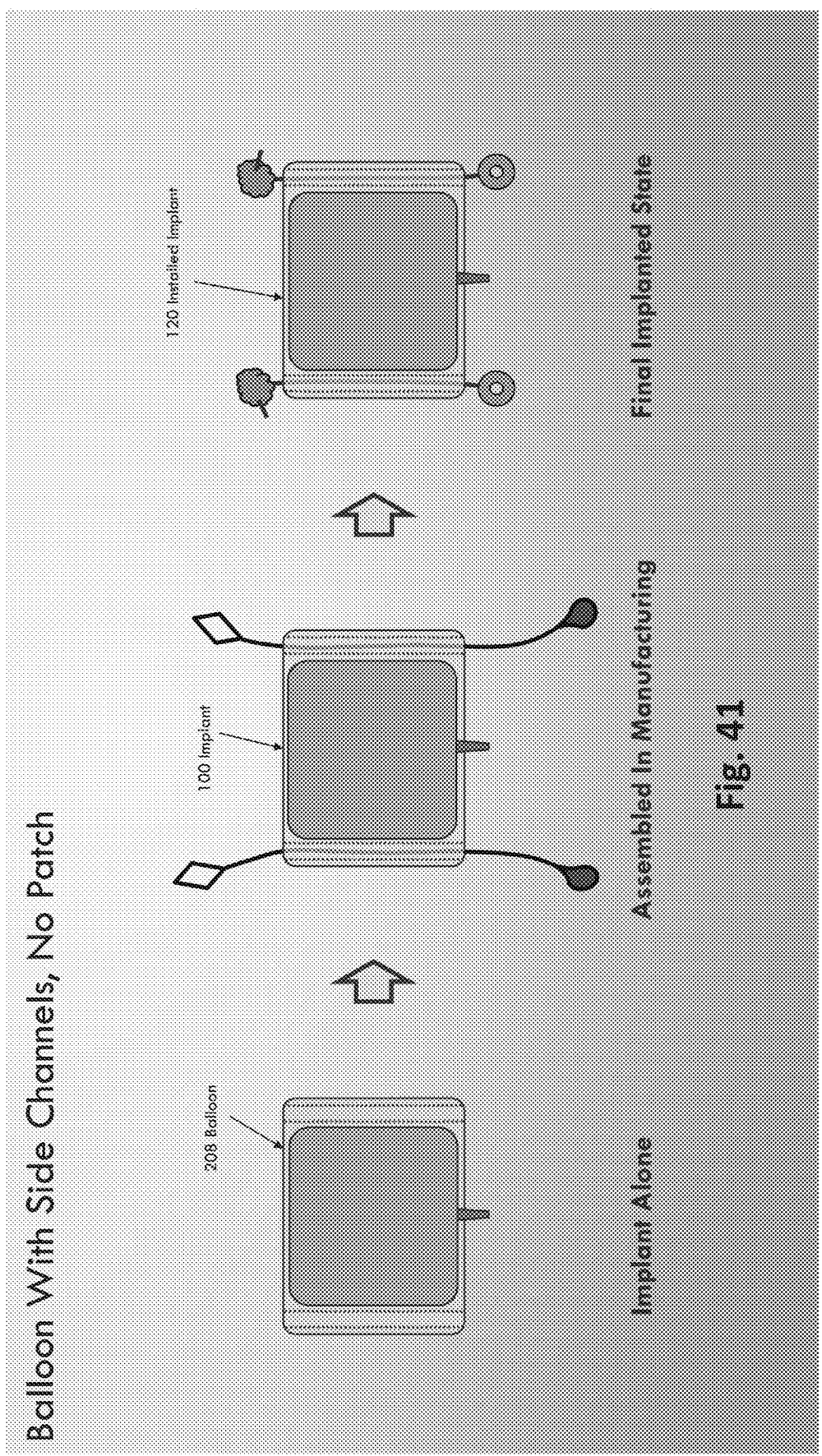
FIG. 41 schematically shows a balloon with side channels and no patch, according to illustrative embodiments.

FIG. 41 schematically shows a balloon 208 with side channels and no patch 204, according to illustrative embodiments. FIGS. 41-44 show the implant 100 alone, the implant as assembled in manufacturing, and in a final implanted state (installed implant 120). Side channels can be added to the balloon 208 during manufacturing. These could be used to load suture through for a simple procedure and proper implant fixation.

Figure 42:
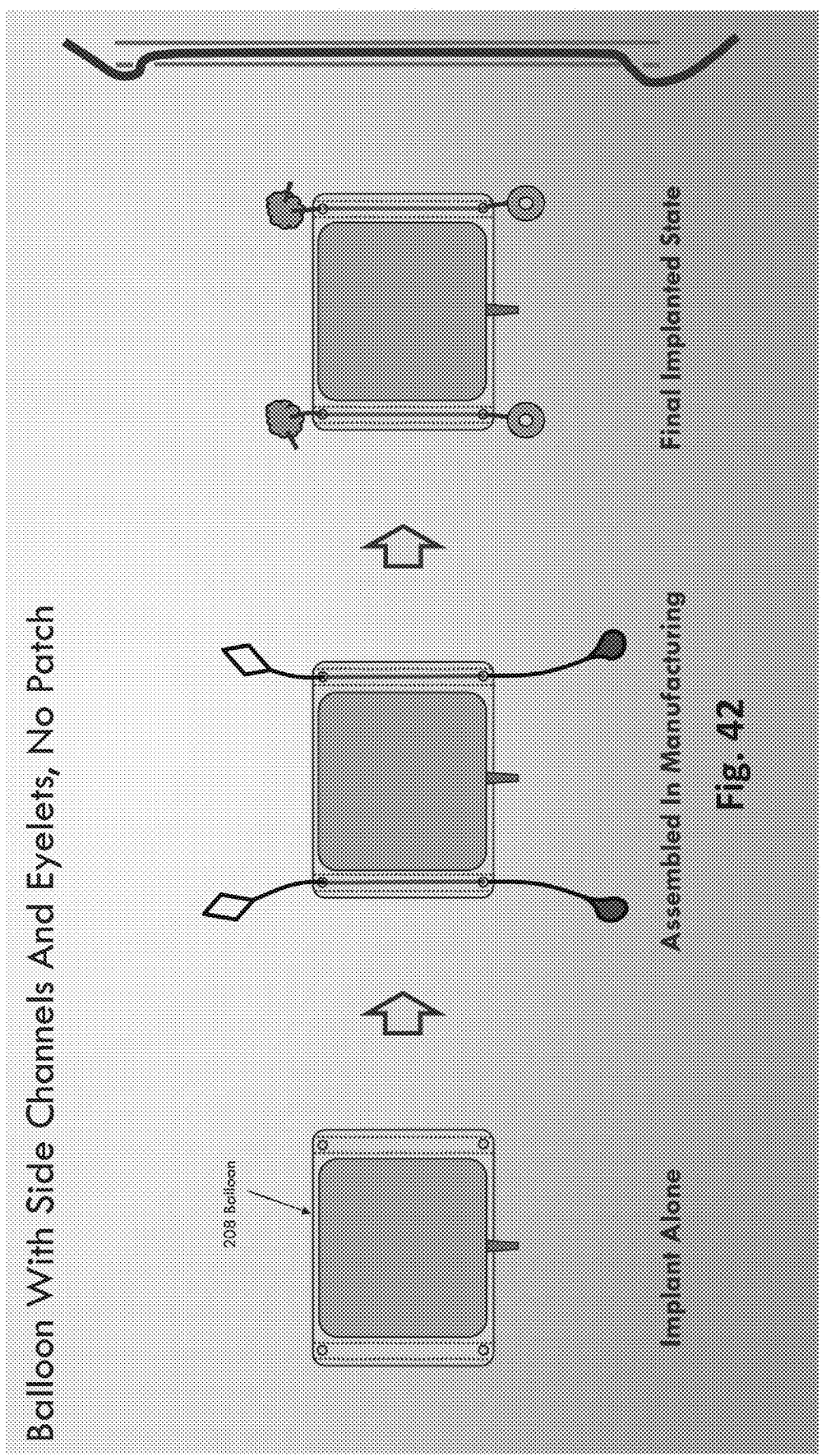
FIG. 42 schematically shows a balloon with side channels and eyelets with no patch, according to illustrative embodiments.

FIG. 42 schematically shows a balloon 208 with side channels and eyelets with no patch 204, according to illustrative embodiments. In this embodiment, there are four eyelets in the corners, at the ends of both side channels. The threader wire (and then suture) would be routed through the channels and up through the eyelets (see cross section at right), which would result in additional frictional retention of the balloon 208 on the spanned sutures. This would help keep the implanted balloon 208 from sliding along the sutures during post operative range of motion.

Figure 43:
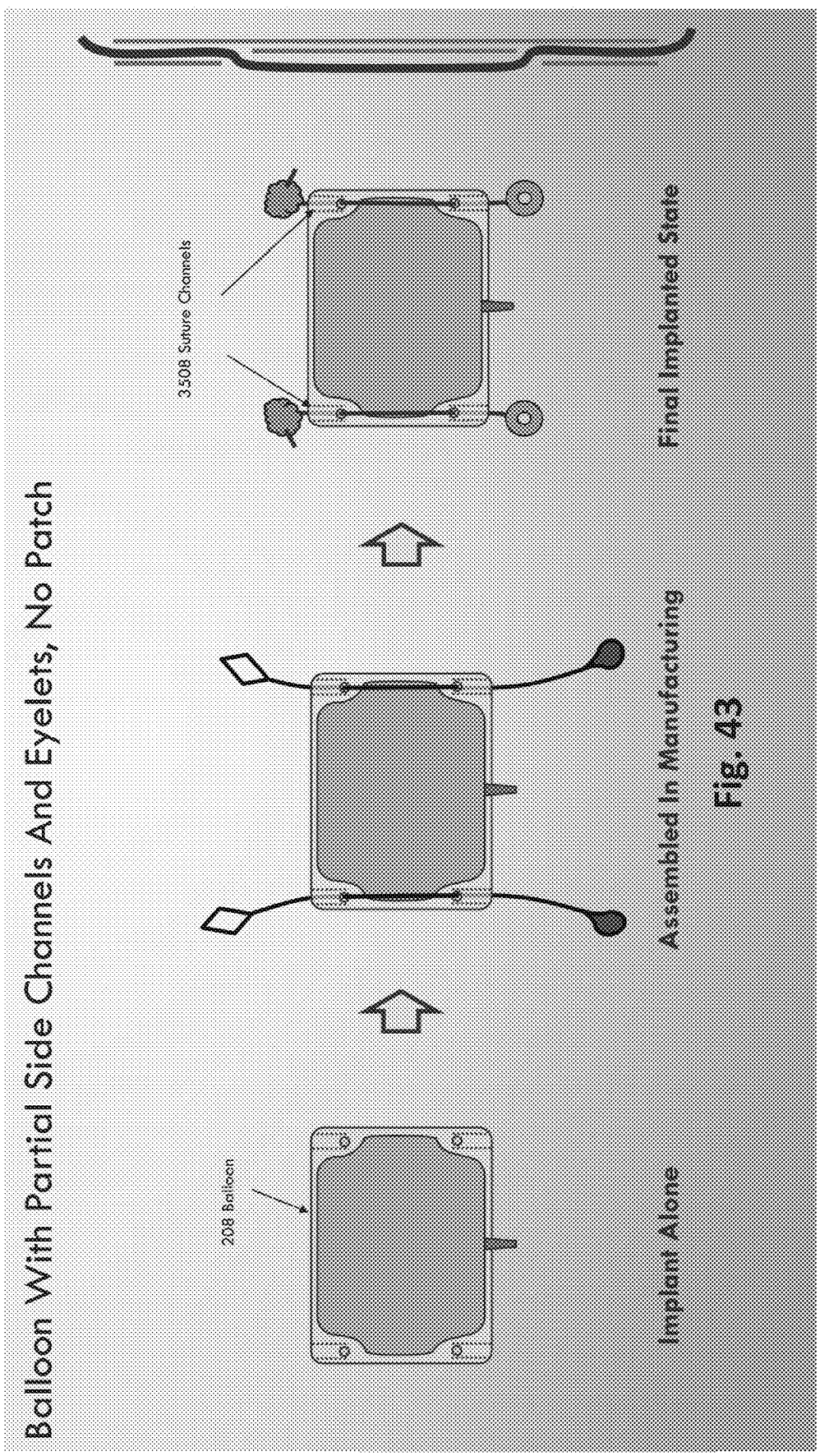
FIG. 43 schematically shows a balloon with partial side channels and eyelets with no patch, according to illustrative embodiments.

FIG. 43 schematically shows a balloon 208 with partial side channels and eyelets with no patch 204, according to illustrative embodiments. This embodiment includes partial channels at the corners, ending in central eyelets. Again, the resulting suture pathway helps to retain the implant in position on the sutures.

This figure also shows an embodiment where the suture effectively extends across the expandable member 208 and yet, may pass in and out of the inner space between the large-area top and bottom surfaces. As such, these eyelets may be considered to form suture channels 3508 extending across the balloon (between the ends/edges of the expandable member 208) even though the sutures are not entirely within the volume of the expandable member 208. This embodiment therefore forms a discontinuous suture channel 3508, which may expose the suture to the top and/or bottom balloon surfaces. In fact, similar discontinuous (or continuous) suture channel embodiments may not extend fully to the edges of the balloon 208.

Figure 44:
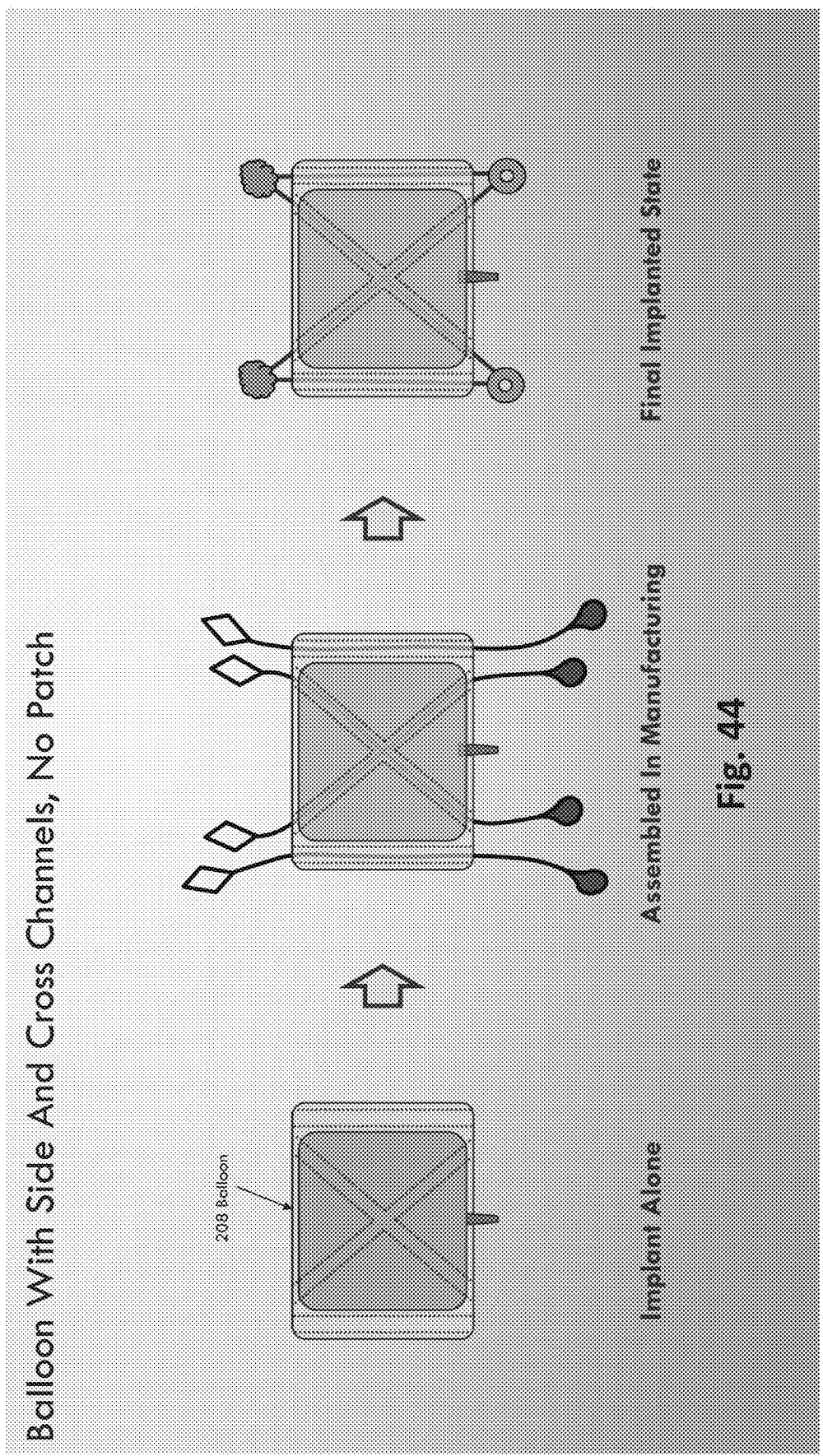
FIG. 44 schematically shows a balloon with side and cross channels and no patch, according to illustrative embodiments.

FIG. 44 schematically shows a balloon 208 with side and cross channels and no patch 204, according to illustrative embodiments. In this embodiment, the channels could not only be up the sides, but also across the patch in an "X" shape-resulting in the standard |X| pattern of spanned sutures.

FIG. 45 schematically shows filling the balloon 208 with hydrogel, according to illustrative embodiments. FIG. 45 illustrates an alternate simplified balloon fill method. In this embodiment, there is no need for a fill line during insertion. At 4504, an empty balloon 208 is secured over the repair. The implant 100 (possibly including or not including patch 204) can be secured in place over the cuff repair with sutures at the corners and spanned over the top (not shown). Then, a needle with hydrogel can enter the repair area (from any portal), enter the balloon 208, and fill it with hydrogel 4508. If there is a target port to be found, a surgeon will need to bring the tip of the needle to the port for filling. This fill method could work with saline or air as well.

The balloon 208 may be sealed by a small o-ring port that closes off after a needle is withdrawn (similar to a basketball fill valve), a one-way flap allowing needle penetration but preventing hydrogel from escaping, a pillow valve 3604 as shown and described herein, or no seal is needed (i.e., the hydrogel does not leave the small puncture hole after the needle is withdrawn).

FIG. 46 schematically shows balloon strips to be loaded and inflated on sutures, according to illustrative embodiments. At 4604, small balloons 208 with lengthwise through holes can be used and may be squared/flat or tubular. The small balloon augments would be very simple to incorporate into the repair procedure, adding very minimal time and complexity. The result would be a double row repair with more spread-out tissue compression.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A method of repairing tissue of a patient, the method comprising:
   securing at least one suture to at least one initial point of the patient;
   coupling the at least one suture to a repair matrix comprising a scaffold portion and an expandable portion, the scaffold portion configured to integrate over time with the tissue being repaired;
   expanding the expandable portion to urge the repair matrix against patient tissue, expanding the expandable portion further producing a securing surface; and
   securing the at least one suture to at least one additional point of the patient,
   the at least one suture traversing the securing surface of the repair matrix between the at least one initial point and at least one additional point to secure the repair matrix to the patient,
   wherein the expandable portion is configured to degrade within the patient, further wherein the scaffold portion is configured to integrate with the tissue faster than the expandable portion degrades within the patient.

2. The method of claim 1 wherein expanding causes the repair matrix to change shape toward a flatter configuration or a three-dimensional configuration.

3. The method of claim 1 wherein the at least one suture forms an X-pattern across the securing surface.

4. The method of claim 1 wherein securing the at least one suture to at least one additional point comprises securing the at least one suture to the one additional point with an anchor.

5. The method of claim 1 wherein expanding the expandable portion comprises directing a fluid through a tube and into the expanding portion.

6. The method of claim 1 wherein the expandable portion comprises an inflatable balloon.

7. The method of claim 1 wherein the scaffold portion comprises a collagen patch.

8. The method of claim 1 wherein the scaffold portion and expandable portion are integrated together.

9. The method of claim 1 wherein the scaffold portion and expandable portion are mechanically coupled together.

10. The method of claim 1 further comprising ejecting the repair matrix from an inserter, the repair matrix expanding after ejected.

\* \* \* \* \*